United States Patent [19]

Shanklin, Jr.

[11] Patent Number: 4,593,102

[45] Date of Patent: Jun. 3, 1986

[54] N-[(AMINO)ALKYL]-1-PYRROLIDINE, 1-PIPERIDINE AND 1-HOMOPIPERIDINECARBOXAMIDES (AND THIOCARBOXAMIDES) WITH SULFUR LINKED SUBSTITUTION IN THE 2, 3 OR 4-POSITION

[75] Inventor: James R. Shanklin, Jr., Richmond, Va.

[73] Assignee: A. H. Robins Company, Inc., Richmond, Va.

[21] Appl. No.: 750,156

[22] Filed: Jul. 1, 1985

Related U.S. Application Data

[63] Continuation-in-part of Ser. No. 598,582, Apr. 10, 1984, abandoned.

[51] Int. Cl.$^4$ ............................................. C07D 211/46
[52] U.S. Cl. ................................. 546/216; 260/239 B; 260/239 BF; 544/130; 544/365; 546/186; 546/188; 546/190; 546/193; 546/194; 546/205; 546/206; 546/208; 546/226; 548/538
[58] Field of Search ............... 546/216, 226, 205, 206, 546/208, 186, 188, 190, 193, 194; 548/538; 544/130, 365; 260/239 B, 239 BF

[56] References Cited

U.S. PATENT DOCUMENTS 4,374,990  2/1983  Weber .............................. 544/365

Primary Examiner—Paul R. Michl

[57] ABSTRACT

Novel pyrrolidine, piperidine and homopiperidinecarboxamide and thiocarboxamide compounds having the formula:

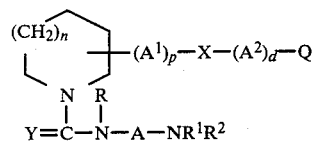

wherein X is —S—, —S(O)— or —S(O)$_2$—; A is a loweralkalene chain and A$^1$ and A$^2$ are alkalene chains when p and d are one; R, R$^1$ and R$^2$ are hydrogen, loweralkyl, phenyl cycloalkyl or phenylalkyl and R$^1$ and R$^2$ may form a heterocyclic residue with the adjacent nitrogen atom; Q is a selected aromatic radical, and the pharmaceutically acceptable acid addition salts useful as cardiac antiarrhythmia agents are disclosed.

Novel chemical intermediates, unsubstituted on pyrrolidine, piperidine and homopiperidine nitrogen but with —(A$^2$)$_p$—X—(A$^2$)$_d$—Q side chain are also disclosed.

38 Claims, No Drawings

N-[(AMINO)ALKYL]-1-PYRROLIDINE, 1-PIPERIDINE AND 1-HOMOPIPERIDINECARBOXAMIDES (AND THIOCARBOXAMIDES) WITH SULFUR LINKED SUBSTITUTION IN THE 2, 3 OR 4-POSITION

REFERENCE TO PARENT APPLICATIONS

This application is a continuation-in-part of U.S. application Ser. No. 598,582 filed on Apr. 10, 1984, abandoned.

BACKGROUND OF THE INVENTION

1. Field of the Invention

The present invention relates to novel N-[(amino)alkyl]-1-pyrrolidine, 1-piperidine and 1-homopiperidinecarboxamides (and thiocarboxamides) substituted in the 2 or 3 pyrrolidine or 2, 3 or 4-piperidine and homopiperidine positions with radicals having thio, sulfinyl or sulfonyl containing linkages, their acid addition salts and hydrates, pharmaceutical methods and compositions associated therewith, and novel intermediates. The carboxamides and thiocarboxamides are useful in controlling cardiac arrhythmias in animals.

2. Information Disclosure Statement

A search of the prior art did not reveal the antiarrhythmia agents of Formula I of the present invention and the compounds are believed to be novel.

Antiarrhythmia agents having the general formula:

$$Ar-B-alk^1-N-\underset{\underset{X}{\overset{\overset{X}{\|}}{C}}}{\overset{R^1}{|}}-N-alk^2-N\underset{R^4}{\overset{R^3}{\diagup}}$$

are disclosed in copending U.S. application Ser. No. 345,452 filed Feb. 3, 1982. In that application, Ar is selected from naphthyl, 2,3-dihydro-1H-inden-4(or 5)yl, 2-furanyl or phenyl; $R^1$ and $R^2$ are selected from hydrogen, loweralkyl, cycloalkyl, phenyl or substituted phenyl, or phenyl-loweralkyl, X is oxygen or sulfur; B is thio, sulfinyl or sulfonyl; $R^3$ and $R^4$ are selected from hydrogen, loweralkyl, phenyl and phenyl-loweralkyl, and $R^3$ and $R^4$ may form a heterocyclic residue; $alk^1$ and $alk^2$ are straight or branched chain alkalenes (1–8 C), and pharmaceutical salts. In all of the above, phenyl may be substituted by conventional radicals. These compounds are relevant in that some might be regarded as open chain analogs of the carboxamides of the present invention.

The 1-unsubstituted pyrrolidines, piperidines and homopiperidines of Formula II, the chemical intermediates of the present invention which have the same 2, 3 or 4 positioned radicals containing thio, sulfinyl or sulfonyl linkages as those in Formula I were not found in a literature search and are believed to be novel.

The preparation of certain starting materials employed in making the novel chemical intermediates of Formula II has been reported by Kostyanovsky, R. G., et al. in Tetrahedron 30, 39–45 (1974) who prepared the L-form of 1-tosyl-2-tosyloxymethylpiperidine from L-prolinole with p-toluenesulfonyl chloride in pyridine.

$$\underset{\underset{H}{\overset{|}{N}}}{\bigcirc}\diagdown CH_2OH \xrightarrow{T_sCl} \underset{\underset{T_s}{\overset{|}{N}}}{\bigcirc}\diagdown CH_2OT_s$$

Similarly, (R)(+)-1-tosyl-2-tosyloxymethylpiperidine was prepared by Aketa, K., et al. in Chem. Pharm. Bull 24(4) 621–631 (1976) from R(+)-2-hydroxymethyl-1-tosylpiperidine and tosyl chloride in pyridine.

Methods of preparing the starting hexahydro-1H-azepin-3-ol and 4-ols, the equivalent of 3 and 4-hydroxyhomopiperidines which are precursors to the homopiperidine compounds of the invention have been disclosed in the prior art (CA 64, 17567a and CA 53, 8160g respectively).

OBJECTS AND SUMMARY OF THE INVENTION

The present invention is concerned with novel 1-pyrrolidinyl, 1-piperidinyl and 1-homopiperidinyl carboxamides (and thiocarboxamides) having the following structure:

Formula I $$\underset{\underset{\underset{Y=C-N-A-NR^1R^2}{\overset{|}{R}}}{\overset{|}{N}}}{\overset{(CH_2)_n}{\bigcirc}}-(A^1)_p-X-(A^2)_d-Q$$

wherein;

n is selected from zero, one or two;

Y is selected from oxygen or sulfur;

A, $A^1$ and $A^2$ are selected from straight or branched chain alkalenes having 1 to 8 carbon atoms and p and d are selected from zero or one with the proviso that when the $-(A^1)_p-X-(A^2)_d-Q$ radical is the 2-position, p is at least one;

X is selected from $-S-$, $-S(O)-$ or $-S(O)_2-$;

R, $R^1$ and $R^2$ are selected from hydrogen, loweralkyl (1–8 carbons), phenyl, cycloalkyl (1–9 carbons) or phenylalkyl (7–14 carbons) and may be the same or different, and $R^1$ and $R^2$ taken together with the adjacent nitrogen atom may form a heterocyclic residue selected from the group consisting of:

(a) 1-pyrrolidino,
(b) 1-piperidino,
(c) 4-morpholino,
(d) 1-piperazino,
(e) a heterocycle of (a) to (d) substituted by a methyl, ethyl, phenyl or phenylloweralkyl,
(f) 2,6-(loweralkyl)$_2$-piperidino,
(g) 4-hydroxy-4-phenylpiperidino,
(h) 4-cyano-4-phenylpiperidino, or
(i) 4-phenyl-1,2,3,6-tetrahydropyridino;

Q is selected from the group consisting of:

(1) 1 or 2-naphthyl,
(2) 2,3-dihydro-1H-inden-4-yl or 2,4-dihydro-1H-inden-5-yl,
(3) biphenyl,
(4) phenyl

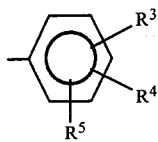

wherein $R^3$ is selected from fluorine, chlorine, bromine iodine, loweralkyl (1–8 carbons), loweralkoxy (1–8 carbons), trifluoromethyl, hydroxy, cyano or nitro; $R^4$ is selected from hydrogen, fluorine, chlorine, bromine, iodine, methyl, ethyl, isopropyl, methoxy, ethoxy and nitro, and $R^5$ is selected from hydrogen, methyl, ethyl, methoxy, ethoxy, methylthio and phenylthio,

wherein $R^6$ is selected from $-NR^7R^8$, $-C(O)NR^7R^8$, $-(CH_2)_bNR^7R^8$, $-B-(CH_2)_bNR^7R^8$ or $-B-(CH_2)_bOR^7$ wherein B is selected from $-O-$, $-S-$, $-S(O)-$ or $-S(O)_2-$, b is 2 or 3 and $R^7$ and $R^8$ are selected from hydrogen, loweralkyl (1–8 carbons), and may be the same or different,

wherein $R^9$ is selected from $-SR^{10}$, $-S(O)R^{10}$ and $-S(O_2)R^{10}$ wherein $R^{10}$ is selected from loweralkyl (1–8 carbons) and phenyl with the proviso that X must be $-S(O)_2-$, or

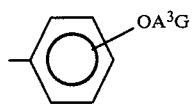

wherein $A^3$ is selected from straight or branched chain alkylenes (2–8 carbons) and G is selected from loweralkoxy (1–8 carbons) or $-NR^{11}R^{12}$ wherein $R^{11}$ and $R^{12}$ are selected from hydrogen, loweralkyl (1–8 carbons), phenyl and phenyl loweralkyl (7–14 carbons) and may be the same or different, and the pharmaceutically acceptable acid addition salts and hydrates thereof.

The invention is also concerned with novel chemical intermediates, a pyrrolidine, piperidine or homopiperidine derivative having the following structure:

Formula II

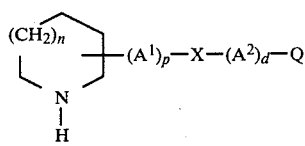

wherein $A^1$, $A^2$, X, n, p, d and Q have the values assigned under Formula I above and the acid addition salts thereof.

In the further definition of symbols in the formulas hereof and where they appear elsewhere throughout this specification and claims, the terms have the following significance:

The term "loweralkyl" as used herein includes straight and branched chain radicals of up to eight carbons inclusive and is exemplified by such groups as methyl, ethyl, propyl, isopropyl, butyl, sec-butyl, tert-butyl, amyl, isoamyl, hexyl, heptyl and octyl radicals and the like. The term "loweralkoxy" has the formula "O-loweralkyl."

The term "cycloalkyl" as used herein includes primarily cyclic alkyl radicals containing 3 to 9 carbon atoms inclusive and includes such groups as cyclopropyl, cyclobutyl, cyclopentyl, cyclohexyl, methylcyclohexyl, cycloheptyl and the like.

The term "halogen" when referred to herein includes fluorine, chlorine, bromine and iodine, preferably fluorine, chlorine and bromine.

The term "straight or branched chain alkylene" as used herein refers to connecting hydrocarbon groups represented by such as methylene ($-CH_2-$), ethylene ($-CH_2-CH_2-$), propylene ($-CH_2CH_2CH_2-$), and the like, and by such as

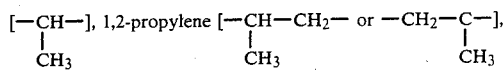

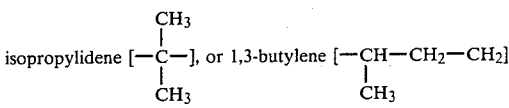

and the like.

The term "heterocyclic residue" as used herein refers to 1-pyrrolidinyl, 1-piperidinyl, 1-piperazinyl, 4-hydroxy- or 4-cyanopiperidin-1-yl, 4-morpholinyl or any of the foregoing heterocycles substituted by methyl, ethyl, phenyl, or phenylloweralkyl and 4-phenyl-1,2,3,6-tetrahydropyridinyl.

"Pharmaceutically acceptable acid addition salts" are those salts formed by the pyrrolidine, piperidine and homopiperidine carboxamides of Formula I with any acid which is physiologically compatible in warm-blooded animals, such as salts being formed by either strong or weak acids. Representative of suitable strong acids are hydrochloric, sulfuric and phosphoric acids. Representative of weak acids are fumaric, maleic, succinic, tartaric, oxalic, citric, cyclohexamic and the like.

The compounds of the present invention act to correct ouabain-induced and coronary-occlusion-induced cardiac arrhythmias in animals as described more fully hereinbelow under "Pharmacology."

The method of treating cardiac arrhythmias in living animals comprises administering the 1-pyrrolidine, 1-piperidine and 1-homopiperidinecarboxamides of Formula I to a living animal body for cardiac arrhythmic effect in an effective amount to control arrhythmia as set forth hereinbelow under "Pharmaceutical Compositions and Administration."

It is therefore an object of the present invention to provide novel N-(aminoalkyl)-1-pyrrolidine, 1-piperidine and 1-homopiperidinecarboxamides and thiocarboxamides having ring substitution with radicals possessing thio, sulfinyl or sulfonyl linkage (Formula I) which have utility in controlling cardiac arrhythmias in living animals and methods of preparation therefor.

Another object is to provide chemical intermediates the 1-unsubstituted pyrrolidines, piperidines and homopiperidines having ring substitution with radicals possessing thio, sulfinyl or sulfonyl linkage (Formula II) which are the precursors of the compounds of Formula I and methods of preparation therefor.

Additional objects will become apparent to one skilled in the art and still others will become apparent hereinafter.

DETAILED DESCRIPTION OF THE INVENTION

The novel compounds of Formula I were obtained from the novel chemical intermediates of Formula II by one of two general methods A or B, or both, with certain limitations as illustrated by chemical formulas and equations in Charts A and B respectively.

Method A (See Chart A). This process for preparation of the compounds of Formula I wherein R is always H and $R^1$ and $R^2$ cannot be H comprises reacting compounds of the following (a), (b), and (c) in sequence:

(a) a compound selected from the group having the formula:

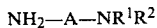

wherein A, $R^1$ and $R^2$ are as described under Formula I, with the proviso that $R^1$ and $R^2$ are not hydrogen.

(b) an imidazole selected from

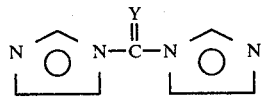

(Y is oxygen or sulfur)

and, (c) a compound selected from the group having the formula:

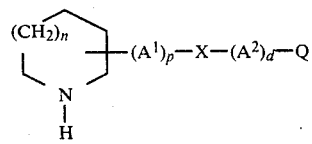

wherein n, $A^1$, $A^2$, p, d, X and Q are as defined under Formula I to give a compound of the group having the formula:

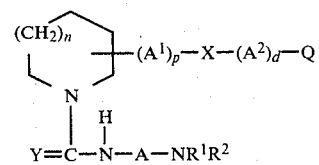

Ia wherein n, A, $A^1$, $A^2$, p, d, X, Q, Y, $R^1$ and $R^2$ have the same values as the starting materials and as defined under Formula I, with the proviso that $R^1$ and $R^2$ are not hydrogen.

Generally, in Method A, an amine of the formula: $NH_2-A-NR^1R^2$ wherein $R^1$ and $R^2$ are other than hydrogen is reacted with 1,1'-carbonyl (or thiocarbonyl) diimidazole at room temperature, preferably in an inert solvent; for example, tetrahydrofuran. Usually about 1 to 1.5 hr is sufficient time to complete the reaction after which a compound of Formula II is added, usually in a suitable solvent such as tetrahydrofuran. The mixture is refluxed until reaction is complete, usually in about 16 hr. Solvent is evaporated usually in vacuo from the mixture and the residue is dissolved in a suitable solvent as methylene chloride and the solution is washed with water and dried. Compounds of Formula Ia are either isolated as the free base by evaporating or crystallizing or as an acid addition salt by reaction with the desired acid using conventional means crystallizing and recrystallizing the salt from a suitable solvent, usually mixtures of diethyl ether with methylene chloride or methanol.

CHART A*
COMPOUND PREPARATION USING DIIMIDAZOLES

React a and b followed by c.

(a) $NH_2-A-NR^1R^2$ ($R^1$ and $R^2$ not H)

(b) 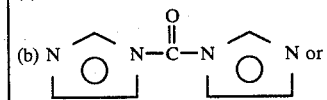 N or

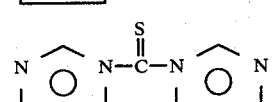

(c) 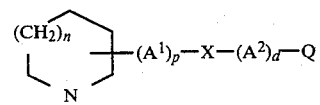

(X=S, —S(O)— or —S(O)$_2$—)

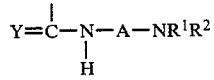

II

↓

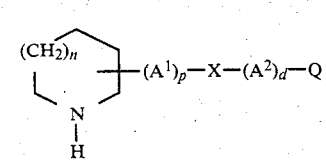

Ia

Footnote Chart A*
Y, A, $A^1$, $A^2$, $R^1$, $R^2$, X, n, p, d, and Q are selected from values assigned under Formula I, except $R^1$ and $R^2$ cannot be hydrogen and R is always hydrogen. Formula Ia is encompassed by Formula I.

Method B (See Chart B). This process for preparation of compounds of Formula I, with the proviso that when $R^2$ is hydrogen, R and $R^1$ must be identical radicals comprises reacting compounds of the following (a), (b), and (c) in sequence:

(a) a compound selected from the group of the formula:

II

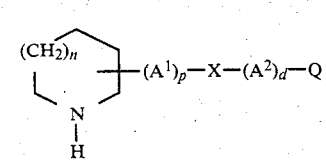

wherein $A^1$, $A^2$, X, n, p, d and Q have the values defined under Formula I,

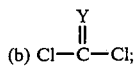

Y is oxygen or sulfur, (c) RNHANR$^1$R$^2$ wherein A, R, R$^1$ and R$^2$ are as defined under Formula I except when R$^2$ is hydrogen, R and R$^1$ must be identical radicals to give a compound of the group having the formula:

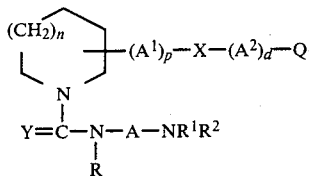

Ib wherein Y, A, A$^1$, A$^2$, R, R$^1$, R$^2$, X, n, p, d and Q have the same values as the starting materials and as defined under Formula I with the proviso that when R$^2$ is hydrogen, R and R$^1$ must be identical radicals.

Generally in Method B, a compound of Formula II is reacted with phosgene or thiophosgene in excess organic base such as triethylamine in an organic solvent such as methylene chloride at room temperature. The mixture is then washed with water and dried and the solvent removed under reduced pressure. The residue is dissolved in a suitable solvent such as tetrahydrofuran and an excess of an amine having the formula RNHANR$^1$R$^2$ wherein when R$^2$ is hydrogen, R and R$^1$ must be the same radical is added and the mixture is refluxed for several hours. The solvent is removed under reduced pressure and the residue dissolved in a solvent such as methylene chloride. The solution is extracted with water and dried and then the solvent is removed under reduced pressure to give the free base. The free base may be converted to an acid addition salt with a suitable acid and further purified by selection of a suitable solvent.

CHART B*
COMPOUND PREPARATION USING PHOSGENES

React a and b followed by c.

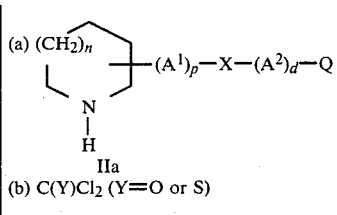

(b) C(Y)Cl$_2$ (Y=O or S)

(c) RNHANR$^1$R$^2$

-continued
CHART B*
COMPOUND PREPARATION USING PHOSGENES

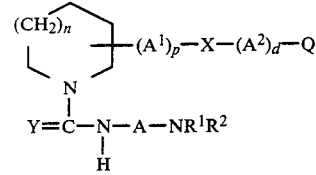

I$_b$

Footnote Chart B*
Y, A, A$^1$, A$^2$, R, R$^1$, R$^2$, X, n, p, d, and Q are selected from values assigned under Formula I, except when R$^2$ is hydrogen, R and R$^1$ must be identical radicals. Formula I$_b$ is encompassed by Formula I.

Collectively, the methods employed for preparing the chemical intermediates of Formula II in the broadest sense is comprised of the following steps:

Broad Step I. A compound of the formula:

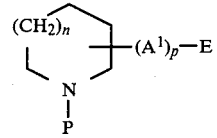

wherein A$^1$, n and p are as defined under Formula I; P is a protecting group selected from benzyl, diphenylmethyl, an arylsulfonyl or an alkylsulfonyl; E is selected from halo or —O—S(O)$_2$—W wherein W is selected from loweralkyl, aryl; e.g., phenyl, 4-methylphenyl or 4-bromophenyl with the following provisos: (1) when P is benzyl or diphenylmethyl, the —(A$^1$)$_p$—E radical is never in the 2-pyrrolidinyl position or the 2 or 3-piperidinyl or homopiperidinyl position, and (2) when P is alkylsulfonyl or arylsulfonyl and the —(A$^1$)$_p$—E radical is in the 2-position, p is always at least one is reacted with a metal sulfide of the formula:

Q—(A$^2$)$_d$S$^-$M$^+$ wherein Q is defined under Formula I with the proviso that Q does not contain an amido component, and additionally, when P is alkylsulfonyl or arylsulfonyl, Q does not contain an amido or cyano component and contains only those oxygen linkages desired to be hydrolyzed by hydrobromic acid in a later step to hydroxyphenyl to obtain a compound of the formula:

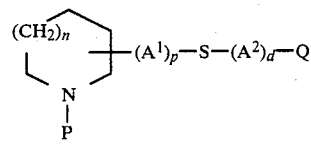

wherein P, n, A$^2$, p, A$^2$, d and Q have the starting values, and additionally, Q may have been converted to hydroxyphenyl.

Broad Step II. A compound of Step I wherein P is

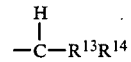

is reacted with phenylchloroformate to obtain a compound of the formula:

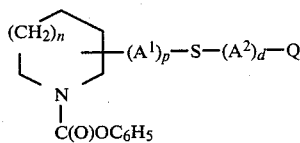

wherein the n, $A^2$, p, $A^2$ and Q are unchanged by the reaction.

Broad Step III. A compound formed in Steps I or II is hydrolyzed to remove the protecting group to give a compound of the formula:

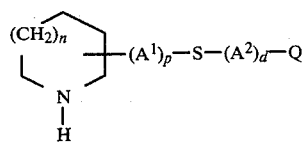

wherein n, $A^1$, p, $A^2$, d and Q have the starting values with the proviso that when the starting Q radical is a loweralkoxy phenyl and hydrobromic acid or conc. sulfuric acid are the hydrolyzing agents the Q radical becomes a hydroxyphenyl.

Broad Step IV. A compound obtained in Step III is optionally oxidized with an appropriate amount of sodium perborate and appropriate conditions of temperature to give a compound of the formula:

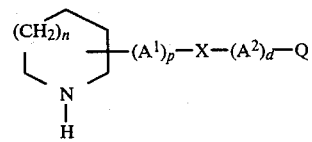

wherein $A^1$, $A^2$, p, d, Q and n have the starting values and X is —S(O)— or —S(O)$_2$—.

Alternately, the sulfide compounds obtained in Steps I or II may be oxidized to a sulfone prior to conducting Steps II or III, respectively.

Broad Step V. When required, hydrolyzing a compound of Formula II wherein Q is cyanophenyl with an acid to give a compound of Formula II wherein Q is a phenyl radical substituted by aminocarbonyl.

Broad Step VI. When required, reacting a compound prepared in Step V with a loweralkylamine to give a compound of Formula II wherein Q is a phenyl radical substituted by mono or diloweralkylaminocarbonyl.

Broad Step VII. When required, reacting a compound of Formula II wherein Q is a hydroxyphenyl radical with an alkali metal salt of a loweralkylanol to give a compound of Formula II wherein Q is phenyl having at least 1 alkoxy substituent not excluding other radicals and may have up to 3 alkoxy substituents.

For purposes of illustrating process requirements, limitations, preferred embodiments and novel features, the general process described above for preparing the intermediates of Formula II is preferably divided based on the method of protecting the heterocyclic nitrogen as follows in Intermediate Process 1 (Chart 1) and Intermediate Process 2 (Chart 2).

Intermediate Process 1 Description (Chart 1)

This process may be used to prepare intermediates of Formula II wherein piperidine is substituted in the 4-position or pyrrolidine is substituted in the 3-position. The process utilizes a benzyl or diarylmethane blocking group initially on pyrrolidine, piperidine or homopiperidine nitrogen during construction of the side chain; i.e. the —(A$^1$)$_p$—X(A$^2$)$_d$—Q radical wherein X is initially a sulfide or sulfonyl linkage. Placement of radicals in the 2 or 3 position of the piperidine or homopiperidine by this method may be hindered by rearrangement reactions. The benzyl group is replaced by a carboxylic acid phenyl ester group by reaction with phenylchloroformate. The carboxylic acid phenyl ester group is removed by hydrolysis with a hot concentrated acid such as hydrobromic acid or sulfuric acid or with an aqueous alkalimetal base, illustratively, 2 Normal sodium hydroxide. Hydrobromic acid is preferred when the side chain is not sensitive to acid hydrolysis and base hydrolysis must be used when Q is phenyl substituted by an alkoxy radical or cyano radical or an —OA$^3$G radical as defined under Formula I. Specifically, Intermediate Process 1 is comprised of the following steps:

Step 1. A compound of the formula

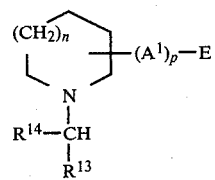

wherein n, $A^1$ and p are as defined under Formula I, $R^{13}$ is phenyl or substituted phenyl, $R^{14}$ is hydrogen, phenyl or substituted phenyl and E is selected from halogen or —O—S(O)$_2$—W and W is selected from loweralkylsulfonyl or phenyl and substituted phenyl, preferably 4-methylphenyl with the proviso that —(A$^1$)$_p$—E is never in the 2-pyrrolidinyl or 2 or 3 piperidinyl or 2 or 3-homopiperidinyl position is reacted with a metal sulfide of the formula:

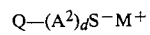

Q—(A$^2$)$_d$S$^-$M$^+$ wherein M is an alkali-metal ion and $A^2$, d and Q are as defined in under Formula I, except Q is never phenyl substituted by amido, to give a compound of the formula:

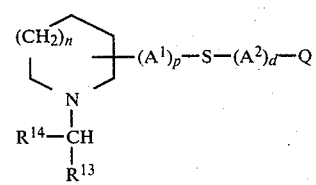

wherein n, $A^1$, p, $A^2$, d, Q, $R^{13}$ and $R^{14}$ are the same as for the starting materials and optionally oxidizing the compound with hot excess sodium perborate under acidic conditions to give a compound of the formula:

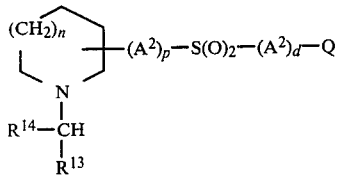

wherein n, $A^1$, p, $A^2$, d, Q, $R^{13}$ and $R^{14}$ are as defined before oxidation.

Step 2. A sulfide or sulfone compound prepared in Step 1 is reacted with phenyl chloroformate to give a compound of the formula:

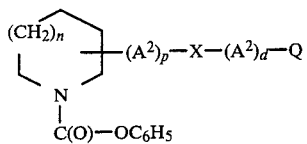

wherein n, $A^1$, p, $A^2$, d and Q are as defined in the foregoing steps and X is —S— or —S(O)$_2$—.

Step 3. A compound prepared in Step 2 is hydrolyzed, preferably with hot hydrobromic acid when the remainder of the molecule is stable to the acid or preferably with alkali metal base when Q contains a substituent such as an oxygen linked radical on phenyl or a cyano radical on phenyl to give a compound of the formula:

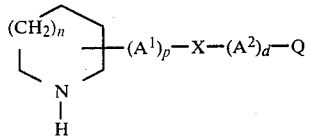

wherein n, $A^1$, p, $A^2$, d and Q are as defined in the foregoing steps and X is —S— or —S(O)$_2$—.

Step 4. Optionally oxidizing a compound prepared in step 3 wherein X is —S— with sodium perborate under acidic conditions to give a compound of the formula:

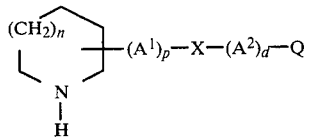

wherein X is —S(O) or —S(O)$_2$— and n, $A^1$, p, $A^2$, d and Q are as defined in the foregoing steps.

CHART 1
(Intermediate Process 1)
PROCESS FOR PREPARING 3-SUBSTITUTED PYRROLIDINE AND
4-SUBSTITUTED PIPERIDINE AND HOMOPIPERIDINE CHEMICAL
INTERMEDIATES USING BENZYL OR DIPHENYL METHANE BLOCKED
HETEROCYCLIC NITROGEN

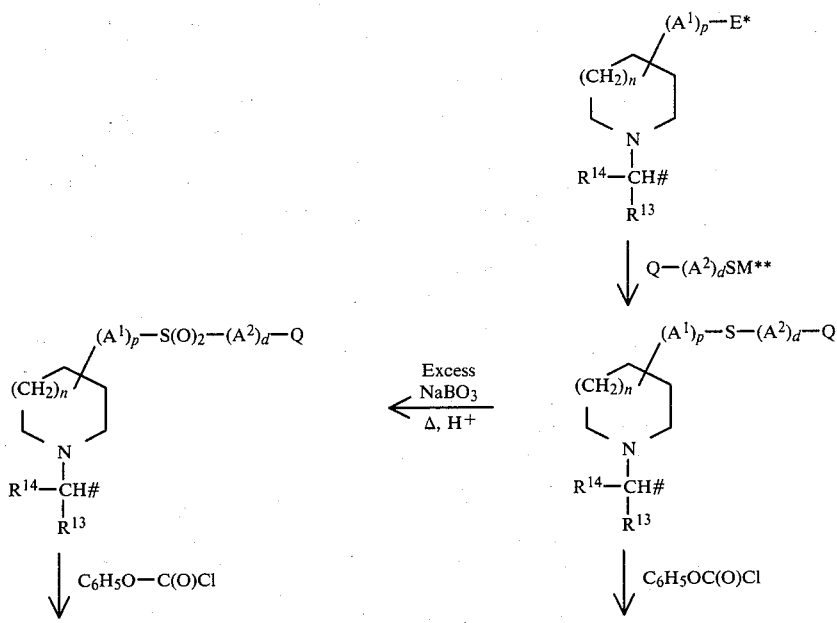

-continued
CHART 1
(Intermediate Process 1)
PROCESS FOR PREPARING 3-SUBSTITUTED PYRROLIDINE AND
4-SUBSTITUTED PIPERIDINE AND HOMOPIPERIDINE CHEMICAL
INTERMEDIATES USING BENZYL OR DIPHENYL METHANE BLOCKED
HETEROCYCLIC NITROGEN

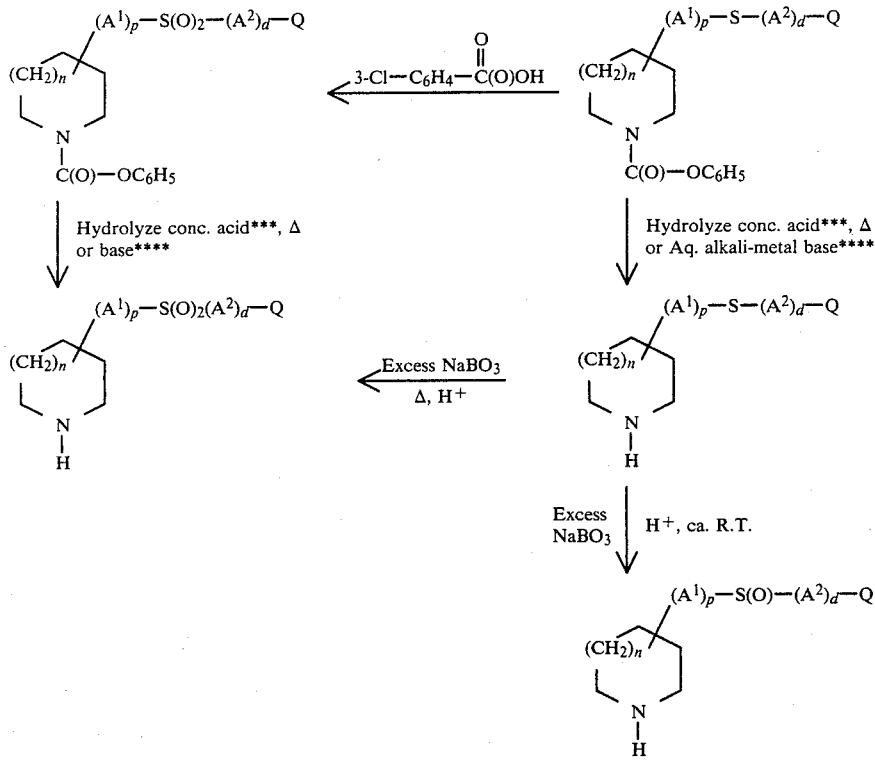

Footnotes to Chart 1
$R^{13}$ = phenyl or substituted phenyl.
$R^{14}$ = H, phenyl or substituted phenyl.
*E selected from halo or —O—S(O)$_2$—W wherein W is selected from loweralkyl, phenyl or methylphenyl with the proviso that —(A$^1$)$_p$E is never in the 2 position of pyrrolidine or the 2 or 3 position of piperidine and homopiperidine
**M = alkali-metal.
***Illustratively 48% HBr or 80% H$_2$SO$_4$.
****Use of alkali-metal base is required when Q is phenyl substituted by loweralkoxy or —OA$^3$G radicals because of instability in hot acid.

Starting compounds shown in Chart I wherein E is —OS(O)$_2$W are prepared by reacting the precursor hydroxyl compound with an alkyl or arylsulfonyl halide.

Intermediate Process 2 (Chart 2). This process may be used to prepare intermediates of Formula II wherein piperidine or homopiperidine is substituted in the 2, 3 or 4 position and pyrrolidine is substituted in the 2 or 3 position and when the substitution is in the 2-position of either piperidine, pyrrolidine or homopiperidine, an alkaline chain of at least one methylene must be present between the heterocyclic and the sulfur on the side chain. Blocking groups—alkylsulfonyl or arylsulfonyl radicals—are used to protect the pyrrolidine, piperidine or homopiperidine nitrogen during construction of the side chain; i.e., the —(A$^1$)$_p$—X—(A$^2$)$_d$—Q radical wherein X is sulfide or sulfonyl linkage. After the side chain has been constructed, the blocking group is removed by hydrolysis with hot concentrated hydrobromic acid to free the heterocyclic nitrogen. Generally, the molecule should otherwise be stable against hot concentrated hydrobromic acid, except when it is desirable to prepare hydroxyphenyl radicals from loweralkoxy phenyl radicals in the same step and, if desired, later reconverted back to loweralkoxy as explained below.

Radicals on phenyl such as cyano and amido cannot be used in this step without degradation. Other more complex oxygen linked radicals on phenyl such as —O—CH$_2$CH$_2$—O—loweralkyl are also subject to degradation and are therefore added after hydrobromic acid hydrolysis of compounds containing phenyl chloride radicals as explained below. Specifically, Intermediate Process 2 is comprised of the following steps:

Step 1. A compound of the formula:

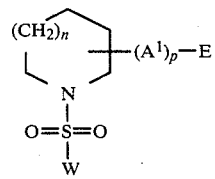

wherein A$^1$, p and n are as defined under Formula I, with the proviso as stated, when the —(A$^1$)$_p$—E radical is in the 2-position, —(A$^1$)$_p$ is at least a methylene link, and E is halo or —O—S—(O)$_2$—W and W is selected from loweralkyl, phenyl or aryl; e.g., phenyl substituted by non-interfering radicals is reacted with a compound of the formula:

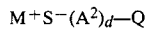

wherein M is an alkali metal and $A^2$ and d are defined under Formula I, and

Q is selected from the group consisting of
(1) 1 or 2-naphthyl,
(2) 2,3-dihydro-1H-inden-4-yl or 2,3-dihydro-1H-inden-5-yl,
(3) biphenyl
(4) phenyl,

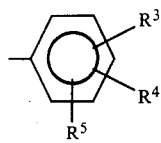 (5)

wherein $R^3$ is selected from fluorine, chlorine, bromine, iodine, loweralkyl (1–8 carbons), loweralkoxy (1–8 carbons), trifluoromethyl or nitro; $R^4$ is selected from hydrogen, fluorine, bromine, iodine, methyl, ethyl, isopropyl, loweralkoxy, or nitro and $R^5$ is selected from hydrogen, methyl, ethyl, methylthio, loweralkoxy or phenylthio,

 (6)

wherein $R^6$ is selected from $-NR^7R^8$, $-B-(CH_2)_bNR^7R^8$ wherein B is selected from $-S-$, $-S(O)-$ or $-S(O)_2-$, b is 2 or 3 and $R^7$ and $R^8$ are selected from hydrogen or loweralkyl (1–8 carbons), and may be the same or different,

 (7)

wherein $R^9$ is selected from $-SR^{10}$ and $-S(O)_2R^{10}$ wherein $R^{10}$ is selected from loweralkyl (1–8 carbons) and phenyl with the proviso that X must be $-S(O)_2-$ to give a compound of the formula:

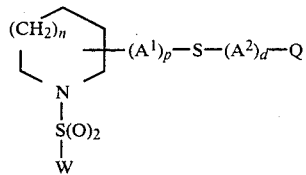

wherein W, $A^1$, $A^2$, n, p, d and Q have the starting values.

Step 2. Optionally oxidizing the compound with metachloroperoxybenzoic acid or hydrogen peroxide in acetic acid to give a compound of the formula:

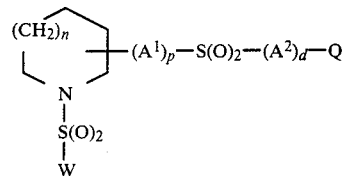

wherein W, $A^1$, $A^2$, n, p, d and Q are the same as for the unoxidized compound.

Step 3. Subjecting a compound obtained in Step 1 or 2 to the hydrolyzing action of hot hydrobromic acid, preferably 48% hydrobromic acid in excess phenol to obtain a compound of the formula:

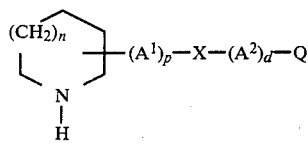

wherein $A^1$, $A^2$, n, p, d and Q have the same values as in Step 2, except loweralkoxy radicals when present have converted to hydroxy and X is $-S-$ or $-S(O)_2-$.

Step 4. Oxidizing a compound obtained in Step 3 wherein X is $-S-$ with sodium perborate to obtain a compound of the formula:

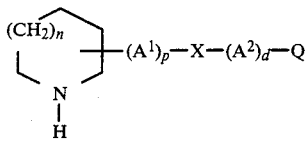

wherein X is $-S(O)$ or $-S(O)_2$ and $A^1$, $A^2$, n, p, d, and Q have the same values as in Step 2.

Step V. Same as Broad Step V above.
Step VI. Same as Broad Step VI above.
Step VII. Same as Broad Step VII above.

The preferred starting compounds in Intermediate Process 2 are the diarylsulfonated compounds which may be prepared by the method reported by Kostyanovsky above.

As mentioned above, the prior art discloses methods of preparing hydroxyhomopiperidines which are used to prepare the intermediates of Formula II. In addition, intermediates of Formula II wherein the hetercycle is a homopiperidine substituted in the four position by an $-(A^1)_p-X-(A^2)_d-Q$ radical wherein X is $-S-$ and Q is non-interfering may be prepared by a series of reactions finding basis in a communication from Sasatoni, S. et al, to Tetrahedron Letters, Vol. 24 (No. 43) pp 4711–4712 (1983) on conversion of oximes to secondary amines. The following reaction scheme represents the synthetic route by which the present compounds may be obtained as represented by $-(A^1)_p-X-(A^2)_d-Q=-S-$phenyl in the 4-position:

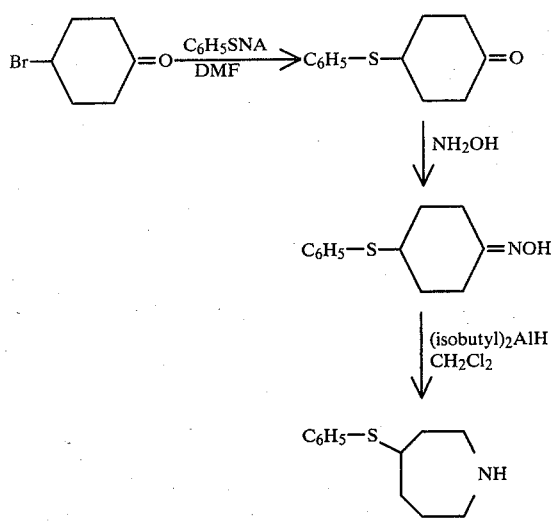

The compounds may then be oxidized to give a sulfinyl and sulfonyl linkages with sodium perborate as in Chart 2.

in a mixture of a suitable solvent for the free base; e.g., generally methylene chloride and an aqueous solution of an alkali metal base and evaporating off the solvent usually in vacuo.

Starting compounds shown in Chart 2 wherein E is —OS(O)$_2$W are prepared by reacting the corresponding hydroxyl compound with an alkane or benzene sulfonyl halide in pyridine to form the esters. When a long reaction time is employed and the starting piperidine is a hydroxymethylpiperidine, it was found that the corresponding chloromethyl compound results which compounds are also a suitable starting material.

Compounds of Formula II, wherein Q is —phenyl—$R^6$ and $R^6$ is —C(O)NR$^7$R$^8$ and $R^7$ and $R^8$ are hydrogen are prepared by first hydrolyzing the corresponding Formula II compound wherein Q is —phenyl—CN with an acid.

Compounds of Formula II, wherein Q is —phenyl—$R^6$ and $R^6$ is —C(O)NR$^7$R$^8$ and $R^7$ and/or $R^8$ are loweralkyl are prepared by heating the amide prepared above; i.e., $R^6$=—C$_6$H$_5$C(O)NH$_2$ with an excess of the alkyl amine overnight at 100° C. in a closed bomb.

CHART 2
PROCESS FOR PREPARING CHEMICAL INTERMEDIATES USING
PHENYL SULFONYL BLOCKING

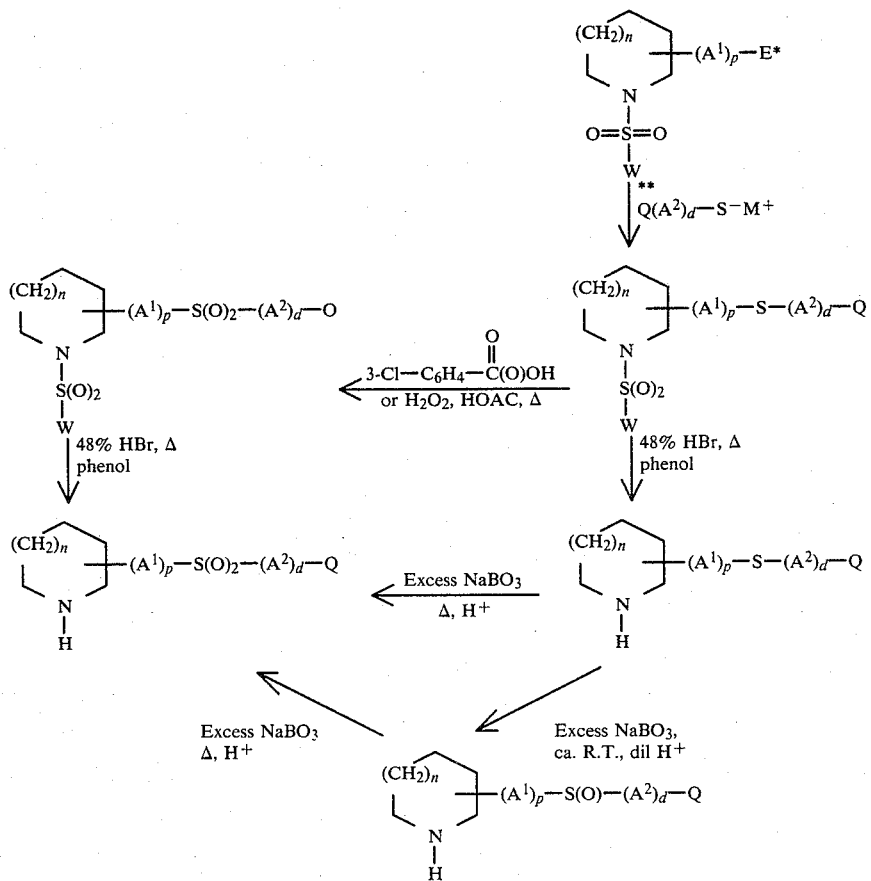

Footnotes Chart 2
E* is halo or —O—S(O)$_2$—W.
W is alkyl, phenyl or substituted phenyl.
**Q is as defined in Step 1 of Intermediate Process 2.

The free base of an acid addition salt of either Formula I or II may be regenerated by partitioning the salt

Discussion of Considerations in Foregoing Processes for Preparation of Intermediates wherein Q is Phenyl Substituted by Radicals Having Oxygen Ether Linkages, e.g., Q=$(CH_3O)_{1-3}C_6H_{4-2-4}$ or $GA_3OC_6H_4$—

Limitations and considerations in construction of —$(A^1)_p$—X—$(A^2)_d$—Q radicals containing oxygen ether linkage are as follows:

(1) Strong acid alternately used in Intermediate process 1 and hydrobromic acid used in Intermediate Process 2 is destructive to oxygen ether linkage. A phenyl ether radical will convert to a hydroxyphenyl radical which is sometimes desirable, thus providing means of obtaining compounds of Formula II wherein hydroxyphenyl is the Q substituent, a possibility under Formula I definition or as an intermediate leading to the starting ether or to another ether linked compound. See below.

(2) —$(A^2)_p$—X—$(A^2)_d$—Q radicals in the 2-pyrrolidinyl position or the 2 or 3-piperidinyl and homopiperidinyl position can only be prepared by Intermediate Process 2 which is, as stated above, destructive to oxygen linkages resulting in hydroxyphenyl radicals. Thus, there is no direct route to phenyl ether radicals in these heterocyclic positions.

(3) 2, 4, and 6-halophenyl—(Q) radicals in compounds of Formula II can be converted to the ethers with an appropriate alkali-metal oxide of an alcohol. However, compounds of Formula II wherein Q has a 3- or 5-halo substitution on phenyl is unreactive to the oxide and conversion does not occur.

Thus, to prepare 3-[$(A^1)_p$—X—$(A^2)_d$]pyrrolidines or 4-[$(A^1)_p$—X—$(A^2)_d$—Q]piperidines and homopiperidines wherein Q is phenyl substituted by an ether component; for example, $(CH_3O)_{1-3}$—$C_6H_4$—, Intermediate Process 1 may be used wherein the metal sulfide starting material: Q—$(A^2)_d$—S⁻M⁺ has, for example, a corresponding Q value of $(CH_3O)_{1-3}$—$C_6H_{2-4}$ wherein —$OCH_3$ radicals may be in any one of the phenyl positions and a base is used to remove the heterocyclic nitrogen protecting group. See Chart 1. On the other hand, if a strong acid is used to remove the protecting group, hydroxyphenyl Q values will result.

To prepare 2-[$(A^1)_p$—X—$(A^2)_d$—Q]pyrrolidines or 2- or 3-[$(A^1)_p$—X—$(A^2)_d$—Q]piperidines and homopiperidines wherein X=Q is phenyl substituted by an ether component; for example, $(CH_3O)_{1-3}$—$C_6H_4$—, Intermediate Process 2 may be used starting with the corresponding phenyl halides as Q value in Q—$(A^2)_d$—S⁻M⁺. See Chart 2. The resulting halophenyl derivative is then converted to the ether by reacting with an appropriate alkoxide or alkali metal salt of an alcohol. If the 3-phenyl position does contain a halo radical, it will remain. Alternately, this procedure may be used also to prepare 3-[$(A^1)_p$—X—$(A^2)_d$-pyrrolidines and 4-[$(A^1)_p$—X—$(A^2)_d$—Q]piperidines and homopiperidines wherein 2, 4, 5 and 6-phenyl halide substituents are converted to an ether component. The $GA_3O$— values on Q in the 2, 4, 5 and 6-phenyl positions are similarly introduced.

To prepare 2-[$(A^1)_p$—X—$(A^2)_d$—Q]pyrrolidines or 2- or 3-[$(A^1)_p$—X—$(A^2)_d$—Q]piperidines and homopiperidines wherein X=$SO_2$ and Q is phenyl substituted in the 3 (or 5) position by an oxygen ether component, Intermediate Process 2 may be used starting with Q value in Q—$(A^2)_d$—S⁻M⁺ of phenyl ether; for example, 3-$OCH_3$—$C_6H_4$— which is hydrolyzed to a Q value of 3-OH—$C_6H_4$— during removal of the protecting group. Illustratively, the 3-OH—$C_6H_4$— radical is then converted back to a 3-$CH_3O$—$C_6H_4$ radical by first protecting the heterocyclic nitrogen, reacting with an alkali metal base and methyl iodide and again removing the protecting group.

The equation outlined in Chart 3 represents the preparation of the 3-hydroxy phenyl compound as would occur in Intermediate Process 2 and conversion to 3-methoxy phenyl. The $GA_3O$— values on Q in the 3-phenyl position may be similarly introduced.

Preparation of intermediates containing oxygen ether linkages are described in Intermediates 5, 18, 22, 23, 24 and 29.

CHART 3

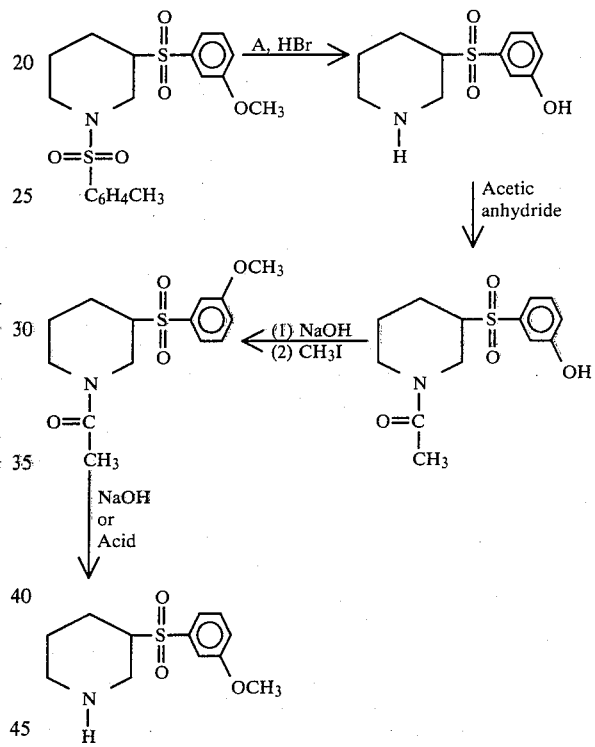

The following preparations 1-51 serve to illustrate the preparation of starting materials used to prepare the chemical intermediates of Formula II.

PREPARATION 1

1-Benzyl-3-(phenylthio)pyrrolidone

A solution of 55 g (0.5 mole) of thiophenol in 50 ml of dimethylsulfoxide was added dropwise with stirring to 250 ml of dimethylsulfoxide containing 21.5 g (0.55 mole) of sodamide. After stirring the mixture at 40° C. for 1 hr, 120 g (0.05 mole) of 3-bromo-1-benzyl-pyrrolidine (slightly exothermic) was added dropwise. The solution was stirred at 60° C. for 1 hr, diluted with 500 ml of water and extracted with isopropyl ether. The ether phase was dried over sodium sulfate and concentrated, and the residue distilled, b.p. 170°-170° C./5 mm. to give 98 g (73%) of product.

Analysis: Calculated for $C_{17}H_{19}NS$: C, 75.79; H, 7.01; N, 5.20; Found: C, 75.58; H, 7.11; N, 5.08

PREPARATION 2

3-[(4-Chlorophenyl)thio]-1-(phenylmethyl)pyrrolidine maleate (and free base)

To a solution of 45.84 g (0.259 mole) of 1-benzyl-3-pyrrolidinol and 29.3 g (0.29 mole) of triethylamine in 400 ml of benzene (cooled by an ice bath) was added a solution of 30.94 g (0.27 mole) of mesyl chloride in benzene. The solution was then stirred at room temperature for 1.5 hr. Isopropyl ether was added and the precipitate which formed was filtered off and discarded. Solvent was evaporated from the filtrate to give a yellow, viscous oil. A solution of this oil in 100 ml of dimethylformamide was added to a solution of 0.35 mole of sodium-p-chlorothiophenoxide prepared from p-chlorothiophenol and sodium hydride in 2 liters of dimethylformamide. The mixture was stirred at 60°–70° C. under nitrogen atmosphere for 18 hr. The solvent was removed in vacuo and the residue was dissolved in methylene chloride. The methylene chloride solution was extracted in sequence with several portions of dilute aqueous sodium hydroxide, several portions of dilute aqueous sulfuric acid and lastly, with one portion of dilute aqueous sodium hydroxide. The methylene chloride phase was then dried over magnesium sulfate and the solvent was removed in vacuo to give an oil, the free base of the title compound. The free base was dissolved in methanol and reacted with a methanol solution of maleic acid and the salt precipitated with diethyl ether. The maleate salt was separated by filtration and recrystallized from methanol-diethyl ether to give 81.47 g (74.9%) of crystalline solid, m.p. 140°–141° C.

Analysis: Calculated for $C_{21}H_{22}NO_4SCl$: C, 60.07; H, 5.28; N, 3.34; Found: C, 59.73; H, 5.25; N, 3.35

PREPARATION 3

3-[(4-Chlorophenyl)sulfonyl]-1-(phenylmethyl)pyrrolidine maleate (and free base)

A mixture of 12.88 g (0.0425 mole) of 3-[(4-chlorophenyl)thio]-1-(phenylmethyl)pyrrolidine maleate and 27 g (0.175 mole) of sodium perborate in 500 ml of 2M sulfuric acid was refluxed for 17 hr. The reaction mixture was poured over ice and the solution made basic with 50% sodium hydroxide solution. The resulting solution was extracted with several portions of methylene chloride. The methylene chloride phase was dried over magnesium sulfate and the solvent was removed in vacuo to give an oil, the free base of the title compound. The maleate salt was prepared and recrystallized from methanol-diethyl ether as in Preparation 2 to give 13.77 g (70.6%) of the product as a white crystalline solid, m.p. 154.5°–155° C.

Analysis: Calculated for $C_{21}H_{22}NO_6SCl$: C, 55.81; H, 4.91; N, 3.10; Found: C, 55.57; H, 4.90; N, 3.08

PREPARATION 4

1-(Phenylmethyl)-3-(phenylsulfonyl)pyrrolidine maleate (and free base)

A solution of 31.8 g (0.085 mole) of 1-benzyl-3-(phenylthio)pyrrolidine and 78 g (0.506 mole) of sodium perborate in 1 liter of 2M sulfuric acid was refluxed for 10 hr and then stirred at room temperature for 6 hr. The mixture was made basic with 50% sodium hydroxide solution and extracted with methylene chloride. The methylene chloride phase was dried over magnesium sulfate and concentrated to give an oil residue, the free base of the title compound. The maleate salts was prepared and recrystallized from methanol-diethyl ether as in Preparation 2 to give 25.5 g (72%) of white crystalline product, m.p. 151°–152° C.

Analysis: Calculated for $C_{21}H_{23}NO_6S$: C, 60.42; H, 5.55; N, 3.36; Found: C, 60.14; H, 5.57; N, 3.38

PREPARATION 5

3-[(4-Methylphenyl)thio]-1-(phenylmethyl)pyrrolidine oxalate (and free base)

To a solution of 76.56 g (0.43 mole) of N-benzyl-3-pyrrolidinol and excess triethylamine in benzene was added a solution of 50.57 g (0.44 mole) of mesyl chloride in benzene and the mixture was stirred at room temperature for about 2 hr. The volume of the solution was approximately 1 liter. Isopropyl ether (500 ml) was added and the mixture stirred for 0.5 hr. The white solid which precipitated was collected and discarded. Solvent was removed in vacuo from the filtrate to give an oil. To a solution of the oil in 800 ml of dimethylformamide was added a solution of 0.544 mole of sodium p-methylthiophenoxide in dimethylformamide and the mixture was held at 60° C. overnight. Solvent was removed from the mixture in vacuo and the residue was partitioned between methylene chloride and dilute aqueous sodium hydroxide. The methylene chloride phase was dried over magnesium sulfate and the solvent removed in vacuo to give an oil, the free base of the title compound. The free base was reacted with oxalic acid, and the salt was crystallized and recrystallized using methanol-diethyl ether solvent pair as in Preparation 2 to give 87.64 g (54.64%) of the white crystalline oxalate, m.p. 141°–144° C. (with decomp.).

Analysis: Calculated for $C_{20}H_{23}NO_4S$: C, 64.32; H, 6.21; N, 3.75; Found: C, 63.86; H, 6.23; N, 3.86

PREPARATION 6

3-[(3,4-Dichlorophenyl)thio]-1-(phenylmethyl)pyrrolidine maleate (and free base)

To a solution of 55.40 g (0.313 mole) of N-benzyl-3-pyrrolidinol and excess triethylamine in 800 ml of benzene was added 37.83 g (0.33 mole) of methanesulfonyl chloride in 200 ml of benzene and the mixture was stirred for 2 hr at room temperature. Isopropyl ether (700 ml) was added and the mixture was stirred at room temperature for 0.5 hr. The white solid which precipitated was collected by filtration and discarded. Solvent was evaporated in vacuo from the filtrate to give an oil residue. To a solution of the oil in 600 ml of dimethylformamide was added a solution of 0.38 mole of sodium 3,4-dichlorothiophenoxide in dimethylformamide and the mixture was stirred overnight at 80° C. The dimethylformamide was removed in vacuo and the residue was partitioned between methylene chloride and dilute aqueous sodium hydroxide. The methylene chloride phase was dried over magnesium sulfate and the solvent removed in vacuo to give the free base of the title compound. The free base was converted to the maleate salt and recrystallized as in Preparation 2 to give 11.82 g (78%) white crystalline solid, m.p. 122°–123° C.

Analysis: Calculated for $C_{21}H_{21}NO_4SCl_2$: C, 55.51; H, 4.66; N, 3.08; Found: C, 55.57; H, 4.74; N, 3.31

PREPARATION 7

3-[(4-Methylphenyl)sulfonyl]-1-pyrrolidinecarboxylic acid phenyl ester

Preparation of Solution of 3-[(4-methylphenyl)thio]-1-pyrrolidine carboxylic acid phenyl ester: A solution of 37.6 g (0.133 mole) of 3-[(4-methylphenyl)thio]-1-(phenylmethyl)pyrrolidine (free base) and 26.1 g (0.167 mole) of phenyl chloroformate in 500 ml of methylene chloride was stirred at room temperature for 4 hr. The solution was extracted with dilute sodium hydroxide and the aqueous layer was discarded. The methylene chloride phase was dried over magnesium sulfate and the solvent removed in vacuo to give an oil residue. The oil was dissolved in ether, and excess triethylamine was added. The white precipitate was filtered off and discarded. The filtrate was extracted with dilute sulfuric acid and the ether phase was dried over magnesium sulfate, the acid layer having been discarded. The solvent was removed in vacuo to give an oil residue.

Preparation of Title Compound: One half of the oil residue prepared above comprised essentially of 3-[(4-methylphenyl)thio]-1-pyrrolidine carboxylic acid phenyl ester was dissolved in 500 ml of methylene chloride and to this solution was added a two-fold excess of metachloroperoxybenzoic acid. The solution was stirred overnight at room temperature after which excess sodium sulfite was added. The mixture was stirred at room temperature for about 1 hr and extracted with dilute aqueous sodium hydroxide, and the methylene chloride phase was dried over magnesium sulfate and the solvent removed in vacuo. The residue was recrystallized from methylene chloride-diethyl ether to give 14.41 g (62.86%) of the sulfonyl title compound as white crystals, m.p. 142°–144° C.

Analysis: Calculated for $C_{18}H_{19}NO_4S$: C, 62.59; H, 5.54; N, 4.06; Found: C, 62.59; H, 5.56; N, 4.05

PREPARATION 8

3-[(3,4-Dichlorophenyl)sulfonyl]-2-pyrrolidine carboxylic acid phenyl ester

A solution of 38.76 g (0.115 mole) of 3-[(3,4-dichlorophenyl)thio]-1-(phenylmethyl)pyrrolidine and 20.5 g (0.131 mole) of phenyl chloroformate in 500 ml of methylene chloride was stirred at room temperature for 2 hours. To the reaction mixture was added 65 g of 80% (0.302 mole) metachloroperoxybenzoic acid and the mixture was stirred at room temperature overnight. Water and an excess of sodium bisulfite were added and the mixture was stirred for several hours. The phases were separated and the methylene chloride layer was extracted with dilute aqueous sodium hydroxide and the aqueous layer discarded. Solvent was removed in vacuo to give an oil. The oil crystallized from a mixture of diethyl ether and hexane to give 35.26 (76.6%) white crystals, m.p. 110°–112° C.

Analysis: Calculated for $C_{17}H_{15}NO_4SCl_2$: C, 51.01; H, 3.78; N, 3.50; Found: C, 51.37; H, 3.84; N, 3.62

PREPARATION 9

3-(Phenylsulfonyl)-1-pyrrolidinecarboxylic acid phenyl ester

A solution of 95.23 g (0.354 mole) of 1-benzyl-3-(phenylthio)pyrrolidine and 64 g (0.409 mole) of phenyl chloroformate in methylene chloride was stirred at room temperature for several hours. Excess isopropyl ether was added and the precipitate which formed was filtered off and discarded. The filtrate was dried over magnesium sulfate and the solvent was removed in vacuo. The residue was dissolved in methylene chloride and 175 g of 80% (0.814 mole) m-chloroperoxybenzoic acid was added. The solution was stirred overnight at room temperature. An aqueous solution of sodium bisulfite was added and the mixture was stirred for several hours and the phases separated. The methylene chloride phase was extracted with dilute aqueous sulfuric acid followed with dilute aqueous sodium hydroxide, the aqueous phases being discarded. The methylene chloride phase was dried over magnesium sulfate and the solvent removed in vacuo to give an oil residue. The oil crystallized from a mixture of methylene chloride and diethyl ether to give 89.26 g (76.2%) white crystals, m.p. 84°–85° C.

Analysis: Calculated for $C_{17}H_{17}NO_4S$: C, 61.62; H, 5.17; N, 4.23; Found: C, 61.64; H, 5.21; N, 4.26

PREPARATION 10

1-[(4-Methylphenyl)sulfonyl]-3-piperidinol ester with 4-methylbenzenesulfonic acid A solution of 73.5 g (0.728 mole) of 3-hydroxypiperidine and 350 g (1.84 mole) of p-toluenesulfonyl chloride in 1 liter of pyridine was stirred at room temperature for 17.5 hr. The solution was quenched in 1 liter of water. The aqueous mixture was extracted with several portions of methylene chloride. The aqueous layer was discarded. The combined methylene chloride phases were extracted with several portions of 1M aqueous sulfuric acid followed with several portions of 1M aqueous sodium hydroxide. The methylene chloride phase was dried over magnesium sulfate and the solvent removed in vacuo to give an oil. The oil was crystallized from diethyl ethermethylene chloride to give a yellow solid, m.p. 132°–133° C.

Analysis: Calculated for $C_{19}H_{23}NO_5S_2$: C, 55.73; H, 5.66; N, 3.42; Found: C, 55.79; H, 5.69; N, 3.38

PREPARATION 11

1-[(4-Methylphenyl)sulfonyl]-4-piperidinol ester with 4-methylbenzenesulfonic acid Following the procedure of Preparation 10 and substituting 4-hydroxypiperidine for 3-hydroxypiperidine, the title compound was obtained in 73.3% yield, m.p. 140.5°–141° C.

Analysis: Calculated for $C_{19}H_{23}NO_5S_2$: C, 55.73; H, 5.66; N, 3.42; Found: C, 55.60; H, 5.64; N, 3.39

PREPARATION 12

3-[(4-Chlorophenyl)thio]-1-[(4-methylphenyl)sulfonyl]-piperidine

A solution of the sodium salt of p-chlorothiophenol in 300 ml of dimethylformamide was prepared by the slow addition of 40.5 g (0.28 mole) of p-chlorothiophenol in dimethylformamide to a mixture of 12.0 g (0.25 mole) of sodium hydride (50% oil dispersion washed with petroleum ether and dried in a stream of nitrogen) in dimethylformamide. After completion of the addition, the solution was stirred for an additional 0.5 hr at room temperature under nitrogen atmosphere. To the foregoing solution was added, all at once in solid form, 94.02 g (0.226 mole) of 1-[(4-methylphenyl)sulfonyl]-3-piperidinol ester with 4-methylbenzenesulfonic acid. The reaction mixture was allowed to stir overnight at 100° C. The mixture was cooled to room temperature and diluted with 3 liters of water and made alkaline with aqueous sodium hydroxide. The mixture was extracted with methylene chloride and the aqueous layer discarded. The methylene chloride phase was back extracted with 10% aqueous sodium hydroxide and the aqueous layer discarded. The methylene chloride phase was dried over magnesium sulfate, filtered and methylene chloride removed in vacuo to give an oil with crystallized upon trituration with isopropyl ether. A 5 g portion of the crystalline residue was recrystallized from methylene chloride-petroleum ether to give 2.9 g (40% yield based on aliquot token) of white crystals, m.p. 71°–73.5° C.

Analysis: Calculated for $C_{18}H_{20}ClNO_2S_2$: C, 56.61; H, 5.28; N, 3.67; Found: C 56.59; H, 5.32; N, 3.69

PREPARATION 13

4-[(4-Chlorophenyl)thio]-1-[(4-methylphenyl)sulfonyl]-piperidine

To a stirred suspension of 0.0238 mole of sodium hydride in 150 ml of dimethylformamide under nitrogen atmosphere at 25° C. was added 5.0 g (0.0347 mole) of p-chlorothiophenol in solid form. After 1 hr, 6.2 g (0.0152 mole) of 1-[(4-methylphenyl)sulfonyl]-4-piperidinol ester with 4-methylphenylbenzenesulfonic acid was added and the solution was stirred at 110° C. for 16 hr. The reaction mixture was quenched in 1 liter of water. The resulting milky mixture was extracted with methylene chloride and the aqueous layer discarded. The methylene chloride phase was extracted with several portions of 1M sodium hydroxide and dried over magnesium sulfate. The solvent was removed in vacuo to give a liquid. White crystalline product, 4.42 g (76.3%), m.p. 112°–113.8° C. was obtained using ether and hexane to recrystallize.

Analysis: Calculated for $C_{18}H_{20}ClNO_2S_2$: C, 56.61; H, 5.28; N, 3.67; Found: C, 56.82; H, 5.36; N, 3.62

PREPARATION 14

3-[(3-Chlorophenyl)thio]-1-[(4-methylphenyl)sulfonyl]-piperidine

A solution of 131.72 g (0.322 mole) of 1-[(4-methylpheyl)sulfonyl]-3-piperidinol ester with 4-methylbenzenesulfonic acid, 49.75 g (0.345 mole) of m-chlorothiophenol and 123.0 g (1.17 mole) of sodium carbonate in 1.5 liter of dimethylformamide was stirred at 80° C. for 24 hr. Two liters of dilute aqueous sodium hydroxide was added and the mixture was extracted with methylene chloride. The methylene chloride phase was extracted with dilute aqueous sodium hydroxide and dried over magnesium sulfate. The solvent was removed in vacuo to give 122 g of an oil, the title product, which NMR showed to be largely 80%.

PREPARATION 15

3-[(3-methylphenyl)thio]-1-[(4-methylphenyl)sulfonyl]-piperidine

A solution of 116.10 g (0.284 mole) of 1-[(4-methylphenyl)sulfonyl]-3-piperidinol ester with 4-methylbenzenesulfonic acid, 60 g (0.48 mole) of p-methylthiophenol and 34 g (0.32 mole) of sodium carbonate in 1 liter of dimethylformamide was stirred at about 80° for 16 hr. The solvent was removed in vacuo and the residue was partitioned between methylene chloride and 1M aqueous sodium hydroxide. The methylene chloride phase was dried over magnesium sulfate and the solvent again removed in vacuo to give an oil confirmed to be the title product by NMR and mass spectrometry.

PREPARATION 16

3-[(3-Fluorophenyl)thio]-1-[(4-methylphenyl)sulfonyl]-piperidine

A solution of 82.2 g (0.20 mol) of 1-[(4-methylphenyl)sulfonyl]-3-piperidinol ester with 4-methylbenzenesulfonic acid, 34.92 g (0.273 mole) of p-fluorothiophenol and 25.5 g (0.241 mole) of sodium carbonate in 1 liter of dimethylformamide was stirred at 60°–80° C. for about 16 hr. The solvent was removed in vacuo and the residue was partitioned between methylene chloride and dilute aqueous sodium hydroxide. The methylene chloride phase was dried over magnesium sulfate and the solvent again removed in vacuo to give an oil which was shown by NMR to contain the product with an impurity.

PREPARATION 17

4-[(4-Chlorophenyl)sulfonyl]-1-[(4-methylphenyl)sulfonyl]piperidine

To a solution of 10.1 g (0.0265 mole) of 4-[(4-chlorophenyl)thio](4-methylphenyl)sulfonyl]piperidine in 150 ml of methylene chloride (cooled to 0° C. in an ice bath) was added a solution of 10.46 g (0.061 mole) of m-chloroperoxybenzoic acid in 150 ml of methylene chloride. The mixture was stirred at room temperature for 45 minutes. A saturated solution of sodium sulfite was added and the solution was stirred for an additional 10 minutes. The phases were separated and the aqueous phase discarded. The methylene chloride phase was extracted with several portions of dilute sodium hydroxide and dried over magnesium sulfate. The volume of the methylene chloride phase was reduced to about 200 ml and the solution placed in a freezer overnight. White crystalline solid, m.p. 263°–264° C. in amount of 5.84 g (53.4%) was obtained.

Analysis: Calculated for $C_{18}H_{20}ClNO_4S_2$: C, 52.23; H, 4.87; N, 3.38; Found: C, 52.26; H, 4.81; N, 3.30

PREPARATION 18

3-[(4-Chlorophenyl)sulfonyl]-1-[(4-methylphenyl)sulfonyl]piperidine

A mixture of 37.96 g (0.10 mole) of 3-[(4-chlorophenyl)thio]-1-[(4-methylphenyl)sulfonyl]piperidine, 300 ml of glacial acetic acid, and 61.8 g of 30% hydrogen peroxide (0.6 mole) was stirred overnight at 90° C. The reaction mixture was cooled to room temperature and diluted with ice water. The diluted mixture was made alkaline with 50% aqueous sodium hydroxide and extracted with methylene chloride. The aqueous phase was discarded. The methylene chloride phase was washed with sodium sulfite to remove traces of peroxide. The methylene chloride solution was dried over magnesium sulfate, filtered and the solvent removed in vacuo to give a yellowish white solid. Recrystallization of an aliquot of the solid from methylene chloridehexanes gave the product, m.p. 186°–187° C. in 57.2% overall yield.

Analysis: Calculated for $C_{18}H_{20}ClNO_4S_2$: C, 52.23; H, 4.87; N, 3.38; Found: C, 52.24; H, 4.88; N, 3.35

PREPARATION 19

3-[(3-Chlorophenyl)sulfonyl]-1-[(4-methylphenyl)sulfonyl]piperidine

A solution of 41.9 g (0.11 mole) of 3-[(3-chlorophenyl)thio]-1-[(4-methylphenyl)sulfonyl]piperidine and a 30% aqueous solution (0.432 mole) of hydrogen peroxide in 1 liter of acetic acid was refluxed for 17 hr. An additional 30% solution (0.1 mole) of hydrogen peroxide was added and refluxing was continued for an additional hour. The reaction mixture was quenched in water to give a precipitate which was collected and recrystallized from methylene chloride-hexane to give 19.49 g (42.7%) white crystalline solid, m.p. 282°–283.5° C.

Analysis: Calculated for $C_{18}H_{20}NO_4S_2Cl$: C, 52.23; H, 4.87; N, 3.38; Found: C, 52.07; H, 4.88; N, 3.51

PREPARATION 20

1-[(4-Methylphenyl)sulfonyl]-3-(phenylsulfonyl)piperidine

Preparation of 3-phenylthio-1-[(4-methylphenyl)sulfonyl]piperidine

A mixture of 1-[(4-methylphenyl)sulfonyl]-3-piperidinol ester with 4-methylbenzenesulfonic acid, excess thiophenol and excess sodium carbonate in dimethylformamide was heated at 90° C. overnight. A large excess of dilute aqueous sodium hydroxide was added. The solution was extracted with methylene chloride. The methylene chloride phase was extracted with dilute aqueous sodium hydroxide, dried over magnesium sulfate and the solvent evaporated in vacuo to give an oil which was shown by mass spectrometry and NMR to be largely 3-phenylthio-1-[(4-methylphenyl)sulfonyl]piperidine Conversion of the sulfide to sulfonyl The oil obtained above was dissolved in three equivalents of 30% hydrogen peroxide in 400 ml of acetic acid and heated at 80° C. for 18 hr. An excess of sodium sulfite was added and the mixture was stirred at room temperature for 1 hr. Water was added and a gummy solid precipitated. The solid was recrystallized from a mixture of methylene chloride-diethyl ether-hexane to give the title compound as white crystals, m.p. 158.5°–161° C.

Analysis: Calculated for $C_{18}H_{21}NO_4S_2$: C, 56.97; H, 5.58; N, 3.69; Found: C, 56.49; H, 5.55; N, 3.65

PREPARATION 21

3-[(4-Fluorophenyl)sulfonyl]-1-[(4-methylphenyl)sulfonyl]piperidine

A solution of 3-[(4-fluorophenyl)thio]-1-[(4-methylphenyl)sulfonyl]piperidine and excess meta-chloroperoxybenzoic acid in methylene chloride was stirred at room temperature overnight. An excess of sodium sulfite and water was added and the mixture was stirred for 2 hr. An excess of sodium hydroxide was added. The methylene chloride phase was extracted with several portions of dilute aqueous sodium hydroxide, dried over magnesium sulfate and the solvent removed in vacuo to give an oil. The oil was crystallized from a mixture of methylene chloride-diethylether-hexane to give white crystals, m.p. 185.5°–186.5° C.

Analysis: Calculated for $C_{18}H_{20}NO_4S_2F$: C, 54.39; H, 5.07; N, 3.52; Found: C, 53.89; H, 5.08; N, 3.45

PREPARATION 22

3-[(4-Methylphenyl)sulfonyl]-1-[(4-methylphenyl)sulfonyl]piperidine

The compound 3-[(4-methylphenyl)thio]-1-[(4-methylphenyl)sulfonyl]piperidine was oxidized and the title compound was isolated as in Preparation 21, m.p. 124°–142° C. It contained a small amount of impurity as shown by thin layer chromatography.

PREPARATION 23

1-[(4-Methylphenyl)sulfonyl]-3-piperidinemethanol Ester with 4-Methylbenzenesulfonic Acid A mixture of 98 g (0.852 mole) of 3-(hydroxymethyl)-piperidine and 380 g (2.0 mole) of p-toluenesulfonyl chloride in one liter of pyridine was stirred at room temperature overnight. Several liters of water were added and the mixture was extracted with methylene chloride. The methylene chloride phase was separated and extracted with dilute aqueous sulfuric acid and then with dilute aqueous sodium hydroxide. The methylene chloride phase was dried over magnesium sulfate and the solvent was removed in vacuo to give the title ester as an oil.

PREPARATION 24

1-[(4-Methylphenyl)sulfonyl]-3-[(phenylthio)methyl]piperidine

To a mixture of 130 g (1.23 mole) of sodium bicarbonate and 145 g (1.32 mole) of thiophenol in 1.5 liters of dimethylformamide (which had stirred at room temperature for about 1 hr) was added 1-[(4-methylphenyl)sulfonyl]-3-piperidinemethanol ester with 4-methylbenzenesulfonic acid (the oil produced in Preparation 23) in 500 ml of dimethylformamide. The mixture was stirred at 80° C. for 12 hours and then at room temperature for 48 hr. One liter of dilute sodium hydroxide was added and the mixture was stirred for 2 hr. A viscous gum formed. The gum was separated and dissolved in methylene chloride. The resulting solution was extracted with several portions of dilute aqueous sodium hydroxide. The methylene chloride phase was dried over magnesium sulfate and the solvent was removed in vacuo. The residue was recrystallized from diethyl ether-methylene chloride to give 221.4 g (72% based on starting 3-(hydroxymethyl)piperidine in Preparation 23) of white crystalline solid, m.p. 72°–75° C.

PREPARATION 25

1-[(4-Methylphenyl)sulfonyl]-3-[(phenylsulfonyl)methyl]piperidine

A solution of 144.49 g (0.40 mole) of 1-[(4-methylphenyl)sulfonyl]-3-[(phenylthio)methyl]piperidine and 114 g of 30% hydrogen peroxide (1.006 mole) in 1 liter of glacial acetic acid was refluxed for 18 hr. A saturated aqueous solution of sodium sulfite was added and the mixture was stirred for about an hour. A gummy solid was isolated and recrystallized from methylene chloride hexane to give 106.0 g (67.4%) of light tan solid, m.p. 135°–136.5° C.

Analysis: Calculated for $C_{19}H_{23}NO_4S_2$: C, 57.99; H, 5.89; N, 3.56; Found: C, 57.95; H, 5.88; N, 3.53

PREPARATION 26

1-[(4-Methylphenyl)sulfonyl]-4-(phenylthio)piperidine

To a mixture of (0.30 mole) of sodium hydride (previously washed with dry petroleum ether) in 250 ml of dimethylformamide was added slowly, with stirring under nitrogen, a solution of 38.56 g (0.35 mole) of benzenethiol in 250 ml of dimethylformamide. The solution was stirred at room temperature for 45 min. To the mixture was added 100.0 g (0.24 mole) of 1-[(4-methylphenyl)sulfonyl]-4-piperidinol ester with 4-methylbenzenesulfonic acid in one portion as a solid. The reaction mixture was stirred over night at room temperature and then diluted slowly with 2.5 liters of water. During the addition of water a solid precipitated. The solid was separated by filtration and dissolved in chloroform. The chloroform solution was extracted with 10% aqueous sodium hydroxide, dried and evaporated to remove solvent, leaving a brown oil residue which slowly crystallized to give white solid. The solid was recrystallized from methanol to give 7.90 g (79%) of white crystalline solid, m.p. 105°–108° C.

Analysis: Calculated for $C_{18}H_{21}NO_2S_2$: C, 62.22; H, 6.09; N, 4.03; Found: C, 62.24; H, 6.08; N, 4.09

PREPARATION 27

1-[(4-Methylphenyl)sulfonyl]-4-[(phenylmethyl)thio]piperidine

A solution of the sodium salt of benzyl mercaptan was prepared in 250 ml of dimethylformamide by the slow addition of a solution of 26.08 g (0.210 mole) of benzyl mercaptan in 125 ml of dimethylformamide to a 50% dispersion containing 0.16 mole of sodium hydride. To the stirred reaction mixture was added in one portion, as a solid, 50.00 g (0.122 mole) of 1-[(4-methylphenyl)sulfonyl]-4-piperidinol ester with 4-methylbenzenesulfonic acid and stirring was continued overnight at room temperature. The reaction mixture was diluted to 2 liters volume with water. The solid which precipitated slowly was separated by filtration and dissolved in chloroform. The chloroform solution was extracted with 10% aqueous sodium hydroxide, dried over magnesium sulfate, filtered and evaporated to give a solid. The solid was recrystallized from methylene chloride-hexane mixture to give the yellow solid, m.p. 153.5°–156.5° C. in 76.8% yield.

Analysis: Calculated for $C_{19}H_{23}NO_2S_2$: C, 63.12; H, 6.41; N, 3.87; Found: C, 62.98; H, 6.36; N, 3.91

PREPARATION 28

1-Phenylsulfonyl-3-piperidinol ester with benzenesulfonic acid

A mixture of 145 g (1.06 mole) of 3-hydroxypiperidine hydrochloride and 460 g benzenesulfonyl chloride in 1 liter of pyridine was stirred at 25° C. for 48 hr. The mixture was quenched in water. The aqueous solution was extracted with methylene chloride. The methylene chloride solution was extracted in sequence with dilute sodium hydroxide, dilute sulfuric acid and dilute sodium hydroxide and then evaporated in vacuo to give a brown solid. Recrystallization of this solid from methylene chloride-hexane gave the product, m.p. 111°–113° C.

Analysis: Calculated for $C_{17}H_{19}NO_5S_2$: C, 53.53; H, 5.02; N, 3.67; Found: C, 53.45; H, 5.00; N, 3.72

PREPARATION 29

4-[(2,5-Dichlorophenyl)thio]-1-[(4-methylphenyl)piperidine

The sodium salt of 2,5-dichlorobenzenethiol was prepared from 0.09 mole of sodium hydride (50% dispersion) and 22.4 g (0.125 mole) of 2,5-dichlorobenzenethiol in 250 ml of dimethylformamide under a nitrogen blanket with stirring for ¾ hr at room temperature. To the solution was added 28.63 g (0.07 mole) of 1-[(4-methylphenyl)sulfonyl]-4-piperidinol ester with 4-methylbenzenesulfonic acid in one portion as solid. The reaction mixture was stirred over the week-end at room temperature, then was diluted with water and made alkaline. The aqueous layer was extracted with chloroform. The chloroform layer was back-extracted with 10% aqueous sodium hydroxide and evaporated to give a yellow solid. Recrystallization of the solid from methylene chloride-hexane gave 4.7 g (94%) of white crystalline solid, m.p. 113°–116° C.

Analysis: Calculated for $C_{18}H_{19}Cl_2NO_2S_2$: C, 51.92; H, 4.60; N, 3.36; Found: C, 51.72; H, 4.59; N, 3.36

PREPARATION 30

1-(Phenylmethyl)-4-piperidinol ester with 4-methylbenzenesulfonic acid maleate [1:1]

A solution of 100 g (0.524 mole) of N-benzyl-4-hydroxypiperidine and 13 g (0.684 mole) of tosylchloride in 600 ml of pyridine was stirred at room temperature over night. One liter of methylene chloride and 500 ml of 0.5M aqueous sodium hydroxide were added to the reaction mixture. The reaction mixture was stirred for 10 min and the phases were separated. The methylene chloride layer was extracted with several portions of dilute sodium hydroxide, dried over magnesium sulfate and evaporated in vacuo to give an oil, the free base of the title compound. The free base was converted to the maleate salt which was recrystallized from methylene chloride-diethyl ether to give white crystalline solid, m.p. 159°–160° C.

Analysis: Calculated for $C_{23}H_{27}NO_7S$: C, 59.86; H, 5.90; N, 3.04; Found: C, 59.79; H, 5.86; N, 2.95

PREPARATION 31

4-[(2-Chlorophenyl)thio]-1-[(4-methylphenyl)sulfonyl]piperidine

Following the procedure of Preparation 26, the sodium salt of o-chlorothiophenol was prepared and reacted with 1-[(4-methylphenyl)sulfonyl]-4-piperidinol ester with 4-methylbenzenesulfonic acid. White crystalline product after recrystallization from methanol, m.p. 93° to 95° C. in 74% yield was obtained.

Analysis: Calculated for $C_{18}H_{20}Cl_2NO_2S_2$: C, 56.61; H, 5.28; N, 3.67; Found: C, 56.44; H, 5.32; N, 3.65

PREPARATION 32

1-[(4-Methylphenyl)sulfonyl]-4-[(4-methylphenyl)thio]piperidine

Following the procedure of Preparation 26, the sodium salt of p-thiocresol was prepared and reacted with 1-[(4-(methylphenyl)sulfonyl]-4-piperidinol ester with 4-methylbenzenesulfonic acid. White crystalline product after recrystallization from methanol, m.p. 97°–101° C. in 55.4% yield was obtained.

Analysis: Calculated for $C_{19}H_{23}NO_2S_2$: C, 63.12; H, 6.41; N, 3.87; Found: C, 63.11; H, 6.35; N, 3.83

PREPARATION 33

4-[(3,4-Dichlorophenyl)thio]-1-[(4-methylphenyl)sulfonyl]piperidine

To a mixture of 0.29 mole of sodium hydride in 150 ml of dimethylformamide was added slowly with stirring under nitrogen to a solution of 60.6 g (0.338 mole) of 3,4-dichlorothiophenol in 150 ml of dimethylformamide. The mixture was stirred for 20 min at room temperature and 98.16 g (0.24 mole) of 1-[(4-methylphenyl)sulfonyl]-4-piperidinol ester with 4-methylbenzenesulfonic acid was added in one portion as solid. After stirring for one hour an orange color developed in the mixture. After two additional hours stirring, the mixture was diluted to 2500 ml with water during which time gelatinous precipitate developed. The aqueous phase was made slightly alkaline with 10% sodium hydroxide and extracted with chloroform. The chloroform extract was then back extracted with 10% sodium hydroxide. After drying and evaporating the solvent, a brown solid was obtained. After recrystallization form methanol, a white solid, m.p. 79°–80° C. in 60.1% yield was obtained.

Analysis: Calculated for $C_{18}H_{19}Cl_2O_2S_2N$: C, 51.92; H, 4.60; N, 3.36; Found: C, 52.10; H, 4.61; N, 3.41

PREPARATION 34

4-[(3-Chlorophenyl)thio]-1-[(4-methylphenyl)sulfonyl]piperidine

To a suspension of 0.381 mole of sodium hydride in 400 ml of dimethylformamide under nitrogen atmosphere using dry-ice acetone cooling bath was slowly added 0.386 mole of m-chlorothiophenol in 200 ml of dimethylformamide. After evolution of hydrogen had ceased, the solution was warmed to room temperature. To the solution was added 140.2 g (0.343 mole) of 1-[(4-methylphenyl)sulfonyl]-4-piperidinol ester with 4-methylbenzenesulfonic acid in 500 ml of dimethylformamide and the mixture was stirred overnight at 90° C. The solution was quenched in 3 liters of water which precipitated a gum. The gum was collected and dissolved in methylene chloride and this solution was extracted several times with dilute sodium hydroxide. The resulting methylene chloride solution was dried over magnesium sulfate and evaporated to give an oil. This was column chromatographed (silica gel gradient elution with petroleum ether-methylene chloride) to give 73.60 g (56.2%) of oil. White solid was obtained by crystallizing from methylene chloride-hexane, m.p. 73.5°–74.5° C.

Analysis: Calculated for $C_{18}H_{20}NO_2S_2Cl$: C, 56.61; H, 5.28; N, 3.67; Found: C, 56.67; H, 5.28; N, 3.67

PREPARATION 35

4-[(4-Fluorophenyl)thio]-1-[(4-methylphenyl)sulfonyl]piperidine

To a stirred suspension of 0.152 mole of sodium hydride in 300 ml of dry dimethylformamide under nitrogen atmosphere at 25° C. was added 20 g (0.156 mole) of p-fluorothiophenol. After 1 hr, 61.90 g (0.151 mole) of 1-[(4-methylphenyl)sulfonyl]-4-piperidinol ester with 4-methylbenzenesulfonic acid was added and the solution was stirred at 93° C. for 14 hr. The mixture was made basic with sodium hydroxide and the solution was extracted with several portions of methylene chloride. The combined methylene chloride extract was extracted with 1M aqueous sodium hydroxide, dried over magnesium sulfate and evaporated in vacuo to give a liquid. On adding diethyl ether, 43.79 g (79.3%) white solid, m.p. 131°–132.5° C. was obtained.

Analysis: Calculated for $C_{18}H_{20}FNO_2S_2$: C, 59.15; H, 5.52; N, 3.83; Found: C, 59.10; H, 5.51; N, 3.81

PREPARATION 36

4-[(4-Chlorophenyl)thio]-1-(phenylmethyl)piperidine maleate [1:1]

To a suspension of 0.035 mole of sodium hydride in dimethylformamide was added 7.0 g (0.0486 mole) of p-chlorothiophenol in dimethylformamide. After evolution of hydrogen had ceased, 10.3 g (0.0299 mole) of 1-(phenylmethyl)-4-piperidinol ester with 4-methylbenzenesulfonic acid (free base) was added and the solution was stirred at room temperature for 19 hr. The solvent was removed by vacuum distillation. The residue was dissolved in methylene chloride. The solution was extracted with several portions of 1M aqueous sodium hydroxide, dried over magnesium sulfate and evaporated in vacuo to give an oil, the free base of the title compound. The oil produced 5.34 g of the solid free base when crystallized from methanol diethyl ether. The maleate salt was prepared, 6.39 g, m.p. 155°–156° C.

Analysis: Calculated for $C_{22}H_{24}NO_4SCl$: C,60.89; H,5.58; N,3.23; Found: C,60.77; H,5.56; N,3.18

PREPARATION 37

2-[[(4-Chlorophenyl)thio]methyl]-1-[(4-methylphenyl)sulfonyl]piperidine

A solution of 57.92 g (0.504 mole) of 2-hydroxymethylpiperidine and 236 g (1.24 mole) of tosylchloride in one liter of pyridine was stirred at 25° C. overnight. The mixture was quenched in water and the aqueous mixture was extracted with several portions of methylene chloride. The combined methylene chloride extract was extracted with 1M sulfuric acid solution followed by 1M aqueous sodium hydroxide, dried over magnesium sulfate and evaporated to give an oil which was shown by NMR and mass spectrometry to be 1-[(4-methylphenyl)sulfonyl]-2-piperidinemethanol ester with 4-methylbenzene sulfonic acid. A mixture of 40.78 g (0.0964 mole) of the oil, 24.60 g (0.171 mole) of p-chlorothiophenol and 25.4 g of sodium carbonate in 200 ml of dimethylformamide was stirred at 100° C. overnight and then quenched in dilute sodium hydroxide. The mixture was extracted with several portions of methylene chloride. The combined extract was extracted with several portions of 1M sodium hydroxide, dried over magnesium sulfate and evaporated in vacuo to give an oil. The oil was crystallized from ether-hexane to give 29.73 g of the solid product. On standing at room temperature, the solid melted.

Analysis: Calculated for $C_{19}H_{22}ClNO_2S_2$: C,57.63; H,5.60; N,3.54; Found: C,57.61; H,5.60; N,3.50

PREPARATION 38

2-[[(4-Chlorophenyl)thio]methyl]-1-phenylsulfonylpiperidine

A mixture of 280 g (1.94 mole) of p-chlorothiophenol and 120 ml of 50% sodium hydroxide in 1 liter of dimethylformamide was stirred for 15 min at 25° C. One mole of 2-chloromethyl-1-(phenylsulfonyl)piperidine was added and the solution was stirred at 60° C. for 65 hr. The mixture was quenched in water and the aqueous mixture was extracted with methylene chloride. The methylene chloride solution was extracted with several portions of dilute sodium hydroxide and evaporated in vacuo to give an oil. The oil was crystallized from methanol to give solid product, m.p. 78.5°–80° C.

Analysis: Calculated for $C_{18}H_{20}N_1O_2S_2Cl$: C,56.60; H,5.28; N,3.67; Found: C,56.47; H,5.36; N,3.68

PREPARATION 39

2-[[(4-Chlorophenyl)sulfonyl]methyl]-1-phenylsulfonylpiperidine

A solution of 65.33 g (0.171 mole) of 2-[[(4-chlorophenyl)thio]methyl]-1-phenylsulfonylpiperidine and 0.72 mole of hydrogen peroxide (30%) in 500 ml of glacial acetic acid was heated at 80° C. for 20 hr. Excess sodium bisulfide was added and the mixture was stirred at room temperature for 30 min. The mixture was quenched in water and the solution was extracted with methylene chloride. The methylene chloride solution was extracted with a solution of sodium bisulfite and dilute sodium hydroxide, dried over sodium sulfate and reduced in volume to about 400 ml on the rotary evaporator. One liter of hexane was added and 52.68 g (74.6%) of solid, m.p. 129°–131° C. precipitated Analysis: Calculated for $C_{18}H_{20}N_1O_4S_2Cl$: C,52.23; H,4.87; N,3.38; Found: C,52.42; H,4.85; N,3.37

PREPARATION 40

1-(Diphenylmethyl)-4-piperidinol monohydrochloride

A mixture of 49.2 g (0.487 mole) of 4-hydroxypiperidine, 98.6 g (0.488 mole) of chlorodiphenylmethane and excess sodium bicarbonate in 600 ml of acetonitrile was refluxed overnight before being quenched in 1 liter of dilute aqueous sodium hydroxide. The aqueous mixture was extracted with methylene chloride. The methylene chloride phase was dried over magnesium sulfate and evaporated in vacuo to give a tan solid. Recrystallization of the solid from methylene chloride-petroleum ether gave 63.45 g (48.9%) tan solid, m.p. 138°–139° C., the free base of the title compound. The free base was reacted with ethereal hydrogen chloride to give the hydrochloride salt which when recrystallized from methanol diethyl ether gave melting point of 249°–250.5° C.

Analysis: Calculated for $C_{18}H_{22}ClNO$: C,71.16; H,7.30; N,4.61; Found: C,70.76; H,7.31; N,4.58

PREPARATION 41

1-(Diphenylmethyl)-4-piperidinol ester with 4-methylbenzenesulfonic acid

A mixture of 57.4 g (0.215 mole) of 1-(diphenylmethyl)-4-piperidinol and 55 g (b 0.289 mole) of tosylchloride in 300 ml of pyridine was stirred at room temperature over night. The mixture was quenched in 500 ml of water. Several hundred ml of methylene chloride and 100 ml of 1M sodium hydroxide were added. The mixture was vigorously agitated. The aqueous phase was separated and extracted with methylene chloride. The methylene chloride phases were combined, dried and evaporated in vacuo to give an oil. The oil was recrystallized from methylene chloride-diethyl ether to give 44.9 g (49.6%) solid, m.p. 122°–123° C.

Analysis: Calculated for $C_{25}H_{27}NO_3S$: C,71.23; H,6.46; N,3.32; Found: C,70.97; H,6.46; N,3.28

PREPARATION 42

1-(Diphenylmethyl)-4-piperidinol ester with 4-methylbenzenesulfonic acid maleate [1:1]

A portion of the 1-(diphenylmethyl)-4-piperidinol ester with 4-methylbenzenesulfonic acid obtained in Preparation 41 was reacted with maleic acid to obtain the maleate salt, m.p. 158.5°–159.5° C.

Analysis: Calculated for $C_{29}H_{31}NO_7S$: C,64.79; H,5.81; N,2.61; Found: C,64.76; H,5.86; N,2.58

PREPARATION 43

1-(Diphenylmethyl)-4-(phenylthio)piperidine

To a stirred suspension of 0.0179 mole of sodium hydride in dimethylformamide was added 3.5 g (0.0318 mole) of thiphenol. After evolution of hydrogen had ceased, 5.5 g (0.0131 mole) of 1-(diphenylmethyl)-3-piperidinol ester with 4-methylbenzenesulfonic acid was added and the mixture was stirred at room temperature for 48 hr. The solvent was removed by vacuum distillation. The residue was dissolved in methylene chloride. The methylene chloride solution was extracted with several portions of 1M sodium hydroxide dried over magnesium sulfate and evaporated in vacuo to give an oil. The solid crystallized on mixing the oil with methyl alcohol and diethyl ether to give white crystals, m.p. 118°–119° C.

Analysis: Calculated for $C_{24}H_{25}NS$: C,80.18; H,7.01; N,3.90; Found: C,79.92; H,6.98; N,3.90

PREPARATION 44

3-Chloromethyl-1-[(4-methylphenyl)sulfonyl]piperidine

A solution of 40.77 g (0.355 mole) of 3-piperidinylmethanol and 160 g (0.842 mole) of tosylchloride in 600 ml of pyridine was stirred at 25° C. for 3 days. The reaction was quenched in 1 liter of 0.1M sodium hydroxide and the resulting mixture was extracted with several portions of methylene chloride. The combined methylene chloride extract was extracted with several portions of 1M sulfuric acid and then with several portions of 1M sodium hydroxide. The methylene chloride solution was dried over magnesium sulfate and the solvent was removed in vacuo to give a brown oil. Recrystallization from methylene chloride hexane gave 16.4 g of the product, m.p. 100°–102° C.

Analysis: Calculated for $C_{13}H_{18}NO_2SCl$: C,54.25; H,6.30; N,4.87; Found: C,54.10; H,6.31; N,4.74

PREPARATION 45

1-[(4-Methylphenyl)sulfonyl]-3-[(phenylthio)methyl]piperidine

To a suspension of 0.0808 mole of sodium hydride in 250 ml of dry dimethylformamide at room temperature and under nitrogen atmosphere was added 9.0 g (0.0818 mole) of thiophenol. After evolution of hydrogen had stopped, 14.18 g (0.0494 mole) of 3-chloromethyl-1-[(4-methylphenyl)sulfonyl]piperidine was added and the solution was stirred at 100°–110° C. for 17 hr. The solution was quenched in 500 ml of 1M sodium hydroxide and the aqueous mixture was extracted with several portions of methylene chloride. The methylene chloride solution was dried over magnesium sulfate and the solvent was removed in vacuo to give an oil which solidified on standing. Recrystallization from methylene chloride-diethyl ether-hexane gave 14.65 g (82%) of the product, m.p. 66.67° C.

Analysis: Calculated for $C_{19}H_{23}NO_2S_2$: C,63.12; H,6.41; N,3.87; Found: C,63.43; H,6.50; N, 3.93

PREPARATION 46

3-[(3-Chlorophenyl)sulfonyl]-1-phenylsulfonylpiperidine

Following the procedure of Preparation 14, 1-phenylsulfonyl-3-piperidinol ester with benzenesulfonic acid is reacted with m-chlorothiophenol and sodium carbonate to give the title compound.

PREPARATION 47

1-[(4-Methylphenyl)sulfonyl]-4-homopiperidinol Ester with 4-Methylbenzenesulfonic Acid Following the procedure of Preparation 10 and substituting 4-hydroxy-hexaydroazepine as prepared by Shiro, M., Bull. Chem. Soc. Japan 31, pp 418–22 (1958); C.A. 53, 8160 g for 3-hydroxypiperidine, the title compound is prepared.

PREPARATION 48

1-[(4-Methylphenyl)sulfonyl]-4-(phenylthio)-homopiperidine

Following the procedure of Preparation 12 and substituting 1-[(4-methylphenyl)sulfonyl]-4-homopiperidinol ester with 4-methylbenzenesulfonic acid for 1-[(4-methylphenyl)sulfonyl]-3-piperidinol ester with 4-methylbenzenesulfonic acid, the title compound is obtained.

PREPARATION 49

1-[(4-Methylphenyl)sulfonyl]-3-homopiperidinol Ester with 4-Methylbenzenesulfonic Acid Following the procedure of Preparation 10 and substituting 3-hydroxy-hexahydroazepine as prepared by Partch, R., Tetrahedron Letters No. 13, pp. 1361–1364 (1966); C.A. 64, 17567a for 3-hydroxypiperidine, the title compound is prepared.

PREPARATION 50

1-[(4-Methylphenyl)sulfonyl]-3-(phenylthio)-homopiperidine

Following the procedure of Preparation 12 and substituting 1-[(4-methylphenyl)sulfonyl]-3-homopiperidinol ester with 4-methylbenzenesulfonic acid for 1-[(4-methylphenyl)sulfonyl]-3-piperidinol ester with 4-methylbenzenesulfonic acid, the title compound is obtained.

PREPARATION 51

4-Phenylthiocyclohexanone Oxime

The title compound is prepared by reacting 4-bromocyclohexanone with the sodium salt of phenyl sulfide in dimethylformamide followed by reacting with hydroxylamine.

The following Intermediates 1–58 serve to more fully illustrate the preparation of the compounds of Formula II useful as chemical intermediates in the preparation of compounds of Formula I and the structures are illustrated in Table 1. The scope of the invention as it pertains to Formula II compounds and their utility as intermediates is not, however, limited thereto. Structures are illustrated in Table 1.

INTERMEDIATE 1

3-[(4-Chlorophenyl)thio]pyrrolidine maleate

A solution of 20.3 g (0.067 mole) of 3-[(4-chlorophenyl)thio]-1-(phenylmethyl)pyrrolidine (free base) and 14.6 g (0.094 mole) of phenyl chloroformate in 800 ml of methylene chloride was stirred at room temperature for 1.5 hr. The solvent was removed in vacuo to give an oil. The oil was dissolved in ether containing excess triethylamine and the mixture was stirred at room temperature for several hours. The solution was filtered and the solvent evaporated from the filtrate to give an oil. The oil was suspended in 300 ml of 80% sulfuric acid and the mixture heated at 60°–80° C. for 18 hr. The resulting solution was quenched in 4 liters of ice-water and the mixture extracted with methylene chloride and the methylene chloride layer was discarded. The acidic aqueous layer was made basic with 50% sodium hydroxide and extracted with methylene chloride. The methylene chloride extract was dried over magnesium sulfate and the solvent evaporated to give an oil, the free base of the title compond. The maleate salt was prepared by reacting the oil with maleic acid in methanol, precipitating with diethyl ether and recrystallizing from methanol-diethyl ether to give 2.6 g (11.8%) of white crystalline solid, m.p. 124.5°–125.5° C.

Analysis: Calculated for $C_{14}H_{16}NO_4SCl$: C,50.99; H,4.89; N,4.25; Found: C,51.00; H,4.91; N,4.40

INTERMEDIATE 2

3-[(4-Chlorophenyl)sulfinyl]pyrrolidine maleate

A solution of 12.3 g (0.0577 mole) of 3-[(4-chlorophenyl)thio]pyrrolidine (free base) and 12.3 g (0.080 mole) of sodium perborate in 400 ml of 1 molar aqueous sulfuric acid solution was stirred at room temperature for 16.5 hr. The solution was made basic with sodium hydroxide and extracted with methylene chloride. The extract was dried over magnesium sulfate and the methylene chloride was removed in vacuo to give an oil, the free base of the title compound. The maleate salt was prepared crystallizing and recrystallizing from methyl alcohol-diethyl ether to give 17.6 g (88.4%) of white crystalline solid, m.p. 133°–135° C. Analysis: Calculated for $C_{14}H_{16}NO_5SCl$: C,48.63; H,4.66; N,4.05; Found: C,48.67; H,4.67; N,4.02

INTERMEDIATE 3

3-[(4-Chlorophenyl)sulfonyl]pyrrolidine hydrochloride

A solution of 8.31 g (0.0248 mole) of 3-[(4-chlorophenyl)sulfonyl]-1-(phenylmethyl)pyrrolidine (free base) and 7.1 g (0.0455 mole) of phenyl chloroformate in 300 ml of methylene chloride was stirred at room temperature for 20 hr. The solution was extracted several times with dilute aqueous sodium hydroxide solution and the organic layer was separated and dried over magnesium sulfate. The solvent was removed in vacuo to give an oil. The oil was suspended in 300 ml of 60% sulfuric acid and the mixture poured over ice. The resulting acidic mixture was extracted with methylene chloride and the methylene chloride layer was discarded. The acidic aqueous layer was made basic with 50% sodium hydroxide solution and extracted with methylene chloride. The methylene chloride extract of the basic solution was dried over magnesium sulfate and the solvent removed in vacuo to give an oil, the free base of the title compound. The hydrochloride salt was prepared using ethereal hydrogen chloride added to a methanol solution of the free base and recrystallized from methyl alcohol-diethyl ether to give 4.11 g (58.9%) of white crystalline solid, m.p. 202°–203° C.

Analysis: Calculated for $C_{10}H_{13}NO_2SCl_2$: C, 42.56; H, 4.64; N, 4.96; Found: C, 42.53; H, 4.63; N, 5.28

INTERMEDIATE 4

3-(Phenylsulfonyl)pyrrolidine maleate

A solution of 16.77 g (0.0557 mole) of 1-(phenylmethyl)-3-(phenylsulfonyl)pyrrolidine (free base) and 12.0 g (0.076 mole) of phenyl chloroformate in 500 ml of methylene chloride was stirred at room temperature for 4 hr. The solvent was removed in vacuo to give an oil. The oil was dissolved in ether with a little methyl alcohol and methylene chloride added to clear the solution. An excess of triethylamine was added and the solution stirred for 1 hr. The mixture was filtered and the solvent removed in vacuo from the filtrate to give an oil. This oil was suspended in 300 ml of 48% hydrobromic acid and the mixture was refluxed for 14.5 hr. The reaction mixture was extracted with several portions of ether and the ether layers discarded. The solution was made basic with 50% aqueous sodium hydroxide and the basic solution was extracted with several portions of methylene chloride. The combined methylene chloride extract of the basic solution was dried over magnesium sulfate and the solvent removed in vacuo to give an oil, the free base of the title compound. The free base was converted to the maleate salt, crystallizing and recrystallizing from methyl alcohol-diethyl ether to give 10.53 g (57.8%) of crystalline solid, m.p. 146.5°–147.5° C.

Analysis: Calculated for $C_{14}H_{17}NO_6S$: C, 51.37; H, 5.23; N, 4.28; Found: C, 51.42; H, 5.25; N, 4.35

INTERMEDIATE 5

3-[(4-Methoxyphenyl)sulfonyl]pyrrolidine hydrochloride

A solution of 15.5 g (0.060 mole) of 3-[(4-chlorophenyl)sulfonyl]pyrrolidine hydrochloride and 9.0 g (0.167 mole) of sodium methoxide in 200 ml of dimethylsulfoxide was stirred at 100° C. for 2 hours. The solvent was removed in vacuo and the residue was partitioned between methylene chloride and water. The methylene chloride solution was dried over magnesium sulfate and the solvent was removed in vacuo to give an oil, the free base of the title compound. The hydrochloride salt was prepared, recrystallizing from methanol-diethyl ether to give 9.1 g (55%) of white crystalline solid, m.p. 181°–182° C.

Analysis: Calculated for $C_{11}H_{16}NO_3SCl$: C, 47.57; H, 5.81; N, 5.04; Found: C, 47.30; H, 5.83; N, 4.99

INTERMEDIATE 6

3-[(4-Methylphenyl)thio]pyrrolidine maleate

A solution of 37.6 g (0.133 mole) of 3-[(4-methylphenyl)thio]-1-(phenylmethyl)pyrrolidine (free base) and 26.1 g (0.167 mole) of phenyl chloroformate in 500 ml of methylene chloride was stirred at room temperature for 4 hr. The solution was extracted with dilute sodium hydroxide solution and the aqueous layer discarded. The methylene chloride layer was dried over magnesium sulfate and methylene chloride removed in vacuo to give an oil. The oil was dissolved in diethyl ether and excess triethylamine added to the solution. A white precipitate was removed by filtering. The ether filtrate was extracted with dilute sulfuric acid and dried over magnesium sulfate. The solvent was removed in vacuo to give an oil. A mixture of one half of the oil in 250 ml of 48% hydrobromic acid containing excess phenol was refluxed for 12 hr. The reaction mixture was poured over ice and the mixture made basic with 50% sodium hydroxide solution. The basic solution was extracted with methylene chloride. The methylene chloride extract was dried over magnesium sulfate and solvent was removed in vacuo to give 9.90 g (77.1%) of oil, the free base of the title compound. A portion of the free base was converted to the maleate salt, crystallizing and recrystallizing from methyl alcohol-diethyl ether to give white crystalline solid, m.p. 97°–98° C.

Analysis: Calculated for $C_{15}H_{19}NO_4S$: C, 58.23; H, 6.19; N, 4.53; Found: C, 57.98; H, 6.19; N, 4.56

INTERMEDIATE 7

3-[(4-Methylphenyl)sulfonyl]pyrrolidine hydrochloride

A solution of 3-[(4-methylphenyl)sulfonyl]-1-pyrrolidinecarboxylic acid phenyl ester (free base) and excess phenol in 48% hydrobromic acid was refluxed for 18 hr. The mixture was poured over ice and the reacting mixture made basic with 50% sodium hydroxide. The basic solution was extracted with methylene chloride. The extract was dried over magnesium sulfate and the methylene chloride removed in vacuo to give an oil, the free base of the title compound. The oil was dissolved in methanol and an excess of ethereal hydrogen chloride added. The product crystallized from the solution as white crystals, m.p. 196°–197° C.

INTERMEDIATE 8

3-[3,4-Dichlorophenyl)sulfonyl]pyrrolidine hydrochloride

A suspension of 32 g (0.08 mole) of 3-[(3,4-dichlorophenyl)sulfonyl]-2-pyrrolidinecarboxylic acid phenyl ester in 500 ml of 48% hydrobromic acid was refluxed for 16 hr and then poured over ice. The mixture was made basic with 50% sodium hydroxide and extracted with chloroform. The chloroform layer was extracted with dilute sodium hydroxide solution and dried over magnesium sulfate. The solvent was removed in vacuo to give a solid, the free base of the title compound. The solid was dissolved in methanol and an excess of ethereal hydrogen chloride added. The hydrochloride salt obtained was recrystallized from methyl alcohol-diethyl ether to give 21.4 g (84.8%) of white crystalline product, m.p. 209°–210° C.

Analysis: Calculated for $C_{10}H_{12}NO_2SCl_3$: C, 37.93; H, 3.82; N, 4.42; Found: C, 38.29; H, 3.86; N, 4.45

INTERMEDIATE 9

3-[(3,4-Dichlorophenyl)thio]pyrrolidine hydrochloride hemihydrate

A solution of 18.90 g (0.0561 mole) of 3-[(3,4-dichlorophenyl)thio]-1-(phenylmethyl)pyrrolidine (free base) and 11.0 g (0.070 mole) of phenyl chloroformate in 800 ml of methylene chloride was stirred at room temperature for 3 hr. The methylene chloride solution was extracted first with dilute sulfuric acid followed by dilute sodium hydroxide, dried and evaporated in vacuo to give an oil. The oil was suspended in 300 ml of 48% hydrobromic acid and the mixture refluxed overnight. The reaction mixture was poured over ice and the mixture made basic with sodium hydroxide. The basic mixture was extracted with methylene chloride and the methylene chloride layer separated and dried over magnesium sulfate and evaporated in vacuo to give an oil, the free base of the title compound. The hydrochloride salt was prepared in methanol with ethereal hydrogen chloride and recrystallized from methanol diethyl ether to give a white crystalline salt. On drying under high vacuum at 80° C. the solid melted. On cooling, the melt formed a gloss, the monohydrochloride, hemihydrate.

Analysis: Calculated for $C_{20}H_{26}N_2OS_2Cl_6$: C, 40.90; H, 4.46; N, 4.77; Found: C, 41.21; H, 4.32; N, 4.73

INTERMEDIATE 10

3-[(3-Chlorophenyl)thio]piperidine hydrobromide

A mixture of 25.2 g (0.175 mole) of m-chlorothiophenol, 48.26 g (0.118 mole) of 1-[(4-methylphenyl)sulfonyl]-3-piperidinol-4-methylphenylsulfonate ester and 56 g of sodium carbonate in 300 ml of dimethylformamide was heated at 100° C. for 22 hr. The mixture was cooled and quenched in excess 1M sodium hydroxide solution. The aqueous mixture was extracted with several portions of methylene chloride and the combined methylene chloride extracts were extracted with several portions of 1N sodium hydroxide solution and dried over magnesium sulfate. The solvent was removed in vacuo to give an oil which was shown by NMR, mass spectrum and TLC to be 3-[(3-chlorophenyl)thio]-1-[(4-methylphenyl)sulfonyl]piperidine. A mixture of the oil and excess phenol in 200 ml of 48% hydrobromic acid was refluxed for 1 hr and quenched in an ice-water mix. The mixture was made basic with sodium hydroxide and extracted with several portions of methylene chloride. The combined methylene chloride extracts were extracted with several portions of 1M sulfuric acid and the methylene chloride layer discarded. The combined acidic extracts were made basic with sodium hydroxide and the basic solution was extracted with several portions of methylene chloride. The aqueous layer was discarded. The combined methylene chloride extract was dried over magnesium sulfate and methylene chloride was removed in vacuo to give an oil, the free base of the title compound. The free base was reacted with hydrogen bromide using the solvent pair isopropanol-isopropyl ether for crystallization and recrystallization to obtain the hydrobromide salt, m.p. 117.5°-120° C.

Analysis: Calculated for $C_{11}H_{15}BrClNS$: C, 42.80; H, 4.90; N, 4.54; Found: C, 42.81; H, 4.96; N, 4.50

INTERMEDIATE 11

3-[(4-Chlorophenyl)thio]piperidine hydrochloride

A mixture of 54 g (0.375 mole) of p-chlorothiophenol, 51.4 g (0.126 mole) of 1-[(4-methylphenyl)sulfonyl]-3-piperidinol-4-methylphenylsulfonate ester and 35 g of sodium carbonate in 500 ml of dimethylformamide was heated at 100° C. for 18 hr. The mixture was cooled and quenched in excess 1M sodium hydroxide solution. The aqueous mixture was extracted with several portions of methylene chloride and the combined methylene chloride extracts were extracted with several portions of 1M sodium hydroxide solution and dried over magnesium sulfate. The solvent was removed in vacuo to give an oil which was shown by NMR, mass spectrum and TLC to be impure N-tosyl-3-(p-chlorothiophenoxy)piperidine. (See Preparation 13 for the pure compound). A mixture of this compound and excess phenol in 75 ml of 48% hydrobromic acid was refluxed for 1 hr and quenched in an ice-water mix. The mixture was made basic with sodium hydroxide and was extracted with several portions of methylene chloride. The aqueous layer was discarded. The combined methylene chloride extracts were dried over magnesium sulfate and the methylene chloride was removed in vacuo to give an oil, the free base of the title compound. The free base was reacted with hydrogen chloride using the solvent pair diethyl ether-methanol for crystallization and recrystallization to obtain the white crystalline hydrochloride salt, m.p. 159°-161° C.

Analysis: Calculated for $C_{11}H_{15}Cl_2NS$: C, 50.01; H, 5.72; N, 5.30; Found: C, 50.07; H, 5.78; N, 5.26

INTERMEDIATE 12

3-[(4-Chlorophenyl)sulfonyl]piperidine fumarate

A mixture of 24.18 g (0.06 mole) of 3-[(4-chlorophenyl)sulfonyl]-1-[(4-methylphenyl)sulfonyl]piperidine, 200 ml of 48% hydrobromic acid and 200 g (2.0 moles) of phenol was refluxed for 1.5 hr. The reaction mixture was cooled and poured into ice. The mixture was carefully made alkaline with 50% sodium hydroxide solution and extracted with diethyl ether. The ether layer was separated and held. The water layer was extracted with methylene chloride and separated, discarding the aqueous phase. The methylene chloride extract was evaporated on a rotary evaporator to give an oil which was combined with the ether layer. The new ether solution was back-extracted with 10% sodium hydroxide solution and the water layer discarded. The ether layer was next extracted with 1N sulfuric acid and the ether layer discarded. The acidic aqueous phase was made alkaline and extracted with methylene chloride. The methylene chloride layer was separated, dried and filtered, and the solvent was removed in vacuo to give a light yellow oil, the free base of the title compound. The free base was dissolved in methanol and an equimolar amount of fumaric acid in methanol was added. Addition of diethyl ether gave crystalline fumarate salt. The yield of white salt after drying over night at 100° C. in vacuo was 11.18 g (49.6%), m.p. 186°-187° C.

Analysis: Calculated for $C_{15}H_{18}ClNO_6S$: C, 47.94; H, 4.83; N, 3.73; Found: C, 47.73; H, 4.82; N, 3.67

INTERMEDIATE 13

3-Phenylsulfonyl)piperidine maleate

A mixture of 27.37 g (0.072 mole) of 1-[(4-methylphenyl)sulfonyl]-3-(phenylsulfonyl)piperidine and excess phenol in 1 liter of 48% hydrobromic acid was refluxed for 2.5 hr. The mixture was poured over ice and made basic with 50% sodium hydroxide solution. The basic solution was extracted with methylene chloride. The methylene chloride extract was dried over magnesium sulfate and evaporated in vacuo to give 13.64 g (83.3%) of a solid, the free base of the title compound. A portion was converted to the maleate salt crystallizing and recrystallizing using the solvent pair methanol-diethyl ether, m.p. 157° C.

Analysis: Calculated for $C_{15}H_{19}NO_6S$: C, 52.78; H, 5.61; N, 4.10; Found: C, 52.85; H, 5.64; N, 4.09

INTERMEDIATE 14

3-[(4-Chlorophenyl)sulfinyl]piperidine maleate

A mixture of 21.4 g (0.094 mole) of 3-[(4-chlorophenyl)thio]piperidine (free base) and 32.2 g (0.21 mole) of sodium perborate in 400 ml of dilute hydrochloric acid was stirred at room temperature overnight. The solution was made basic with 50% sodium hydroxide solution and extracted with methylene chloride. The methylene chloride extract was dried over magnesium sulfate and evaporated in vacuo to give an oil, the free base of the title compound. A portion of the oil was converted to the maleate salt, using the solvent pair methanol-diethyl ether for crystallizing and recrystallizing. White crystalline solid was obtained, m.p. 139°–140.5° C.

Analysis: Calculated for $C_{15}H_{18}NO_5$: C, 50.07; H, 5.04; N, 3.89; Found: C, 49.82; H, 5.11; N, 3.94

INTERMEDIATE 15

3-[(3-Chlorophenyl)sulfonyl]piperidine hydrochloride

A mixture of 13.79 g (0.033 mole) of 3-[(3-chlorophenyl)sulfonyl]-1-[(4-methylphenyl)sulfonyl]piperidine and excess phenol in 300 ml of 48% hydrobromic acid was refluxed for 1½ hr and then was poured over ice. The aqueous mixture was made basic with 50% sodium hydroxide and extracted with methylene chloride. The methylene chloride extract was dried over magnesium sulfate and the solvent was evaporated in vacuo to give an oil, the free base of the title compound. A solution of the oil in methanol was treated with excess ethereal hydrogen chloride, ether was added to give the hydrochloric acid salt which was recrystallized from methanol-ether to give 8.03 g (81.5%) white crystals, m.p. 179°–181° C.

Analysis: Calculated for $C_{11}H_{15}NO_2SCl_2$: C, 44.60; H, 5.10; N, 4.73; Found: C, 4470; H, 5.12; N, 4.81

INTERMEDIATE 16

3-[(4-Methylphenyl)sulfonyl]piperidine maleate

A solution of 41.1 g (0.105 mole) of 3-[(4-methylphenyl)sulfonyl]-1-[(4-methylphenyl)sulfonyl]piperidine and excess phenol in 500 ml of 48% hydrobromic acid was refluxed for 3 hr and then stirred at room temperature overnight. The mixture was made basic with 50% sodium hydroxide solution and extracted with methylene chloride. The aqueous layer was discarded. The methylene chloride layer was extracted with several portions of dilute sulfuric acid and the methylene chloride layer was discarded. The acidic extract was made basic with sodium hydroxide and the basic solution was extracted with methylene chloride. The aqueous layer was discarded. The methylene chloride layer was dried over magnesium sulfate and the solvent was evaporated in vacuo to give an oil, the free base of the title compound. The oil was dissolved in methanol and reacted with maleic acid in methanol using ether to precipitate the maleate salt and methanol-diethyl ether to recrystallize. A white solid, 17.09 g (45.8%), m.p. 157.5°–159° C. was obtained.

Analysis: Calculated for $C_{16}H_{21}NO_6S$: C, 54.07; H, 5.96; N, 3.94; Found: C, 54.02; H, 6.00; N, 3.97

INTERMEDIATE 17

3-[(4-Fluorophenyl)sulfonyl]piperidine maleate

A solution of 32.33 g (0.081 mole) of 3-[(4-fluorophenyl)sulfonyl]-1-[(4-methylphenyl)sulfonyl]piperidine and excess phenol in 400 ml of 48% hydrobromic acid was refluxed overnight. The reaction mixture was made basic with 50% sodium hydroxide and extracted with methylene chloride. The methylene chloride solution was dried over magnesium sulfate and the solvent was evaporated in vacuo to give an oil, the free base of the title compound. The free base was reacted with maleic acid using the solvent pair methanol-diethyl ether for crystallization and recrystallization to obtain the white maleate salt, m.p. 170°–170.5° C. in the amount of 21.02 g (72.1%).

Analysis: Calculated for $C_{15}H_{19}NO_6SF$: C, 49.99; H, 5.31; N, 3.89; Found: C, 50.28; H, 5.08; N, 3.90

INTERMEDIATE 18

3-[(4-Methoxyphenyl)sulfonyl]piperidine maleate

A mixture of 3-[(4-chlorophenyl)sulfonyl]piperidine (free base) and excess sodium methoxide in 300 ml of dimethylsulfoxide was heated at 90°–100° C. for 1.5 hr. The solvent was removed in vacuo, and the residue was partitioned between methylene chloride and water. The water layer was discarded. The methylene chloride layer was extracted with dilute sulfuric acid and the methylene chloride layer discarded. The acidic extract was made basic with 50% sodium hydroxide and the basic solution extracted with methylene chloride. The aqueous layer was discarded. The methylene chloride layer was dried over magnesium sulfate and the solvent was removed in vacuo to give an oil, the free base of the title compound. A portion of the free base was converted to the maleate salt using the solvent pair methanol-diethyl ether for crystallization and recrystallization. White crystalline product, m.p. 150°–151° C. was obtained.

Analysis: Calculated for $C_{16}H_{21}NO_7S$: C, 51.74; H, 5.70; N, 3.77; Found: C, 51.82; H, 5.69; N, 3.79

INTERMEDIATE 19

4-[(4-Chlorophenyl)thio]piperidine monohydrochloride ¼.hydrate

A suspension of 11.0 g (0.0288 mole) of 4-[(4-chlorophenyl)thio]-1-[(4-methylphenyl)sulfonyl]piperidine and 11.6 g (0.123 mole) of phenol in 80 ml of 48% hydrobromic acid was refluxed for 35 min and was then quenched in 500 ml of water. The aqueous mixture was made basic with 50% sodium hydroxide and extracted with several portions of methylene chloride. The combined methylene chloride extract was dried over magnesium sulfate and the solvent was evaporated to give an oil, the free base of the title compound. The free base was converted to the hydrochloric acid salt in methylene chloride-diethyl ether to give 6.07 g of white crystalline solid. Recrystallization from methylene chloride gave 5.20 g (68.4%) of the title product, m.p. 160°–162° C.

Analysis: Calculated for $C_{44}H_{62}Cl_8N_4S_4O$: C, 49.17; H, 5.81; N, 5.21; Found: C, 49.11; H, 5.63; N, 5.21

INTERMEDIATE 20

4-[(4-Chlorophenyl)sulfonyl]piperidine Monohydrochloride

A mixture of 10.14 g (0.0246 mole) of 4-[(4-chlorophenyl)sulfonyl]-1-[(4-methylphenyl)sulfonyl]piperidine and 40 ml of phenol in 120 ml of 48% hydrobromic acid was refluxed for one hr and quenched in 800 ml of water. The mixture was made basic with 50% sodium hydroxide and then extracted with methylene chloride. The methylene chloride extract was dried over magnesium sulfate and the volume was reduced to 200 ml in vacuo. Excess ethereal hydrogen chloride was added to give a white precipitate, the hydrochloride salt. Recrystallization of the salt from methanol-diethyl ether gave 3.80 g (52.0%) of a crystalline solid, m.p. 280°–281.5° C.

with decomposition. An additional 0.77 g (10.6%) of product was obtained from the filtrate.

Analysis: Calculated for $C_{11}H_{15}Cl_2NO_2S$: C, 44.60; H, 5.10; N, 4.73; Found: C, 44.38; H, 5.00; N, 4.74

INTERMEDIATE 21

4-[(4-Chlorophenyl)sulfinyl]piperidine, Monohydrochloride

A solution of 5.78 g (0.020 mole) of 4-[(p-chlorophenyl)thio]piperidine hydrochloride hydrate and 4.61 g (0.030 mole) of sodium perborate in 200 ml of dilute hydrochloride acid was stirred at room temperature overnight. The reaction mixture was quenched in dilute sodium hydroxide and the resulting basic solution was extracted with methylene chloride. The methylene chloride layer was dried over magnesium sulfate and the solvent was removed in vacuo to give a white solid, the free base of the title compound. The free base was reacted with ethereal hydrogen chloride and the salt was recrystallized from methanol-diethyl ether to give the product as a white crystalline solid, m.p. 220°–221° C.

Analysis: Calculated for $C_{11}H_{15}NOSCl_2$: C, 47.15; H, 5.40; N, 5.00; Found: C, 47.00; H, 5.36; N, 4.91

INTERMEDIATE 22

N,N-Dimethyl-2-[4-[(3-piperidinyl)sulfonyl]phenoxy]ethanamine dimaleate

A mixture of 3.2 g (0.133 mole) of sodium hydride and 13.49 g (0.152 mole) of 2-(dimethylamino)ethanol in dimethylsulfoxide was stirred at room temperature for 0.5 hr. A solution of 26.16 g (0.101 mole) of 3-[(4-chlorophenyl)sulfonyl]piperidine (free base) in dimethylsulfoxide was added and the mixture was heated at 100° C. for 2 hr. The solvent was removed in vacuo and the residue was partitioned between methylene chloride and dilute sodium hydroxide. The aqueous layer was discarded. The methylene chloride layer was extracted with dilute sulfuric acid and the methylene chloride layer was discarded. The aqueous layer was made basic with 50% sodium hydroxide and extracted with methylene chloride. The aqueous layer was discarded. The methylene chloride layer was dried over magnesium sulfate and the solvent was removed in vacuo to give an oil, the free base of the title compound. The free base was converted to the maleate salt, using the solvent pair methanol-diethyl ether for crystallizing and recrystallizing, a white crystalline solid, m.p. 125°–126.5° C.

Analysis: Calculated for $C_{23}H_{32}N_2O_{11}S$: C, 50.73; H, 5.92; N, 5.14; Found: C, 50.55; H, 5.92; N, 5.06

INTERMEDIATE 23

N,N-Diethyl-2-[4-[(3-piperidinyl)sulfonyl]phenoxy]ethanamine dimaleate

A mixture of 1.98 g (0.0825 mole) of sodium hydride and 11.7 g (0.1 mole) of 2-(N,N-diethylamino)ethanol in 400 ml of dimethylsulfoxide was stirred at room temperature for 0.5 hr. A solution of 14.87 g (0.0574 mole) of 3-[(4-chlorophenyl)sulfonyl]piperidine (free base) in 100 ml of dimethylsulfoxide was added and the mixture was stirred at 80°–100° C. for 1.5 hr. The solvent was removed in vacuo and the residue was partitioned between methylene chloride and dilute sulfuric acid. The methylene chloride layer was discarded. The aqueous extract was made basic with sodium hydroxide and extracted with methylene chloride. The aqueous layer was discarded. The methylene chloride layer was dried over magnesiumسulfate and solvent was removed in vacuo to give an oil, the free base of the title compound. The free base was converted to the maleate salt, using the solvent pair methanol-diethyl ether for crystallizing and recrystallizing. The white crystalline product was obtained in the amount of 27.88 g (84.9%), m.p. 139.5°–140.5° C.

Analysis: Calculated for $C_{25}H_{36}N_2O_{11}S$: C, 52.44; H, 6.34; N, 4.89; Found: C, 52.31; H, 6.34; N, 4.83.

INTERMEDIATE 24

3-[[4-(2-Methoxyethoxy)phenyl]sulfonyl]piperidine Hydrochloride

A mixture of 1.56 g (0.065 mole) of sodium hydride and 5.32 g (0.07 mole) of 2-methoxyethanol in 300 ml of dimethylsulfoxide was stirred at room temperature for 0.5 hr. A solution of 12.0 g (0.0463 mole) of 3-[(4-chlorophenyl)sulfonyl]piperidine (free base) in 100 ml of dimethyl sulfoxide was added and the mixture was stirred at 80°–100° C. for 1 hr. The solvent was removed in vacuo and the residue was partitioned between methylene chloride and water. The methylene chloride layer was dried over magnesium sulfate and the solvent was removed in vacuo to give an oil, the free base of the title compound. The free base was reacted with ethereal hydrogen chloride, crystallizing and recrystallizing using the solvent pair methanol-diethyl ether to give 10.12 g (65.2%) of the white crystalline hydrochloride salt, m.p. 206°–208° C.

Analysis: Calculated for $C_{14}H_{22}NO_4SCl$: C, 50.07; H, 6.60; N, 4.17; Found: C, 49.86; H, 6.64; N, 4.13

INTERMEDIATE 25

3-[(Phenylsulfonyl)methyl]piperidine hydrochloride

A mixture of 70 g (0.178 mole) of 1-[(4-methylphenyl)sulfonyl]-3-[(phenylsulfonyl)methyl]piperidine and 120 g (1.27 mole) of phenol in 400 ml of 48% hydrobromic acid was refluxed for 4 hr and then made basic with 50% sodium hydroxide. The mixture was extracted with methylene chloride and the aqueous layer discarded. The methylene chloride layer was extracted with dilute sulfuric acid and the methylene chloride layer discarded. The aqueous layer was made basic with sodium hydroxide and extracted with methylene chloride. The aqueous layer was discarded. The methylene chloride layer was dried over magnesium sulfate and the solvent was removed in vacuo to give an oil, the free base of the title compound. The free base was reacted with ethereal hydrogen chloride, crystallizing and recrystallizing using the solvent pair methanol-diethyl ether to give 31.12 g (63.5%) of the white crystalline hydrochloride salt, m.p. 225°–226.5° C.

Analysis: Calculated for $C_{14}H_{22}NO_4SCl$: C, 50.07; H, 6.60; N, 4.17; Found: C, 49.86; H, 6.64; N, 4.13.

INTERMEDIATE 26a TO s

Utilizing the procedure of Intermediate 15, the following are prepared by refluxing their corresponding precursors having a (4-methylphenyl)sulfonyl radical on the piperidine nitrogen (obtained by above-described and illustrated methods) with hydrobromic acid:

(a) 3-(1-naphthylsulfonyl)piperidine hydrochloride,
(b) 3-(2-naphthylsulfonyl)piperidine hydrochloride,
(c) 3-[(2,3-dihydro-1H-inden-4-yl)sulfonyl]piperidine hydrochloride,
(d) 3-[(2,3-dihydro-1H-inden-5-yl)sulfonyl]piperidine hydrochloride, (e) 3-(4-biphenylsulfonyl)piperidine hydrochloride,
(f) 3-[(4-fluorophenyl)sulfonyl]piperidine hydrochloride,
(g) 3-[(4-cyanophenyl)sulfonyl]piperidine hydrochloride,
(h) 3-[(4-nitrophenyl)sulfonyl]piperidine hydrochloride,
(i) 3-[(4-dimethylaminophenyl)sulfonyl]piperidine hydrochloride,
(j) 3-[4-[(N,N-dimethylamino)carbonyl]phenyl]sulfonyl]piperidine hydrochloride,
(k) N,N-diethyl-2-[4-[(3-piperidinyl)sulfonyl]phenylthio]ethanamine hydrochloride,
(l) N,N-diethyl-2-[4-[(3-piperidinyl)sulfonyl]phenylsulfonyl]ethanamine hydrochloride,
(m) N,N-diethyl-2-[4-(3-piperidinyl)sulfonyl]phenyl]ethanamine hydrochloride,
(n) 3-[[4-(methylthio)phenyl]sulfonyl]piperidine hydrochloride,
(o) 3-[[4-(methylsulfonyl)phenyl]sulfonyl]piperidine hydrochloride,
(p) 3-[[4-(phenylthio)phenyl]sulfonyl]piperidine hydrochloride,
(q) 3-[(4-trifluoromethylphenyl)sulfonyl]piperidine hydrochloride,
(r) 3-[(4-bromophenyl)sulfonyl]piperidine hydrochloride, and
(s) 3-[(4-iodophenyl)sulfonyl]piperidine hydrochloride.

INTERMEDIATE 27a AND b

Utilizing the procedure of Intermediate 21 and substituting the following for 4-[(p-chlorophenyl)thio]piperidine:
N,N-diethyl-2-[4-[(3-piperidinyl)sulfonyl]phenylthio]ethanamine, and
3-[4-(methylthiophenyl)sulfonyl]piperidine,
there are obtained:
(a) N,N-diethyl-2-[4-[(3-piperidinyl)sulfonyl]phenylsulfinyl]ethanamine hydrochloride, and
(b) 3-[4-(methylsulfinyl)phenyl)sulfonyl]piperidine hydrochloride.

INTERMEDIATE 28a-f

Utilizing the procedure of Intermediate 15, the following are prepared by refluxing their corresponding precursors having a (4-methylphenyl)sulfonyl radical on the piperidine nitrogen (obtained by above-described and illustrated methods) with hydrobromic acid:
(a) 3-[(2,3-dimethylphenyl)sulfonyl]piperidine hydrochloride,
(b) 3-[(2,4-dimethylphenyl)sulfonyl]piperidine hydrochloride,
(c) 3-[(2,3-trimethylphenyl)sulfonyl]piperidine hydrochloride,
(d) 3-[(2,4,5-trimethylphenyl)sulfonyl]piperidine hydrochloride,
(e) 3-[(4-tertiarybutylphenyl)sulfonyl]piperidine hydrochloride, and
(f) 3-[(2-methyl-4-ethylphenyl)sulfonyl]piperidine hydrochloride.

INTERMEDIATE 29a-i

By reacting the following with an appropriate alkali-metal alkoxide:
3-[(2,4-dichlorophenyl)sulfonyl]piperidine,
3-[(3,4-dichlorophenyl)sulfonyl]piperidine,
3-[(3,5-dichlorophenyl)sulfonyl]piperidine,
3-[(2,6-dichlorophenyl)sulfonyl]piperidine,
3-[(3,4,5-trichlorophenyl)sulfonyl]piperidine,
3-[(4-chlorophenyl)sulfonyl]piperidine, and
3-[(4-chloro-2-methylphenyl)sulfonyl]piperidine,
there are obtained:
(a) 3-[(2,4-dimethoxyphenyl)sulfonyl]piperidine,
(b) 3-[(2,4-diethoxyphenyl)sulfonyl]piperidine,
(c) 3-[(3-chloro-4-methoxyphenyl)sulfonyl]piperidine,
(d) 3-[(3-chloro-5-methoxyphenyl)sulfonyl]piperidine,
(e) 3-[(2,6-dimethoxyphenyl)sulfonyl]piperidine,
(f) 3-[(3-chloro-4,5-dimethoxyphenyl)sulfonyl]piperidine,
(g) 3-[(4-n-butoxyphenyl)sulfonyl]piperidine,
(h) 3-[(4-n-butoxyphenyl)sulfonyl]piperidine,
(i) 3-[(2-methyl-4-ethoxyphenyl)sulfonyl]piperidine.

INTERMEDIATE 30a-i

Utilizing the procedure of Intermediate 15, the following are prepared by refluxing their corresponding precursors having a (4-methylphenyl)sulfonyl radical on the piperidine nitrogen (obtained by above-described and illustrated methods) with hydrobromic acid:
(a) 3-[(2-chloro-6-nitrophenyl)sulfonyl]piperidine hydrochloride,
(b) 3-[(2-nitro-3-chlorophenyl)sulfonyl]piperidine hydrochloride,
(c) 3-[(3-chloro-4-nitrophenyl)sulfonyl]piperidine hydrochloride,
(d) 3-[(2-nitro-4-chlorophenyl)sulfonyl]piperidine hydrochloride,
(e) 3-[(3-chloro-5-nitrophenyl)sulfonyl]piperidine hydrochloride,
(f) 3-[(3-nitro-4-chlorophenyl)sulfonyl]piperidine hydrochloride,
(g) 3-[(2-nitro-5-chlorophenyl)sulfonyl]piperidine hydrochloride,
(h) 3-[(3-chloro-4-methylthiophenyl)sulfonyl]piperidine hydrochloride, and
(i) 3-[(3-chloro-4-phenylthiophenyl)sulfonyl]piperidine hydrochloride.

INTERMEDIATE 31a TO d

Utilizing the procedure of Intermediate 15, the following are prepared by refluxing their corresponding precursors having a (4-methylphenyl)sulfonyl radical on the pyridine nitrogen (obtained by above-described and illustrated methods) with hydrobromic acid:
(a) 3-[[(3-chlorophenyl)sulfonyl]methyl]piperidine hydrochloride,
(b) 3-[(1-naphthylsulfonyl)methyl]piperidine hydrochloride,
(c) 3-[[(2,3-dihydro-1H-inden-4-yl)sulfonyl]methyl]piperidine hydrochloride,
(d) 3-[2-(3-chlorophenyl)sulfonyl]ethyl]piperidine hydrochloride.

INTERMEDIATE 32

The following are reacted with lhenyl chloroformate as in Intermediate 3 followed by hydrolysis with a base such as sodium hydroxide:
1-benzyl-3-[(3,4-dimethoxyphenyl)thio]piperidine,
1-benzyl-3-[(3,4-dimethoxyphenyl)sulfonyl]piperidine,
1-benzyl-3-[(3,5-dimethoxyphenyl)sulfonyl]piperidine, and,
1-benzyl-3-[(3,4-trimethoxyphenyl)sulfonyl]piperidine,
to give the following:
(a) 3-[(3,4-dimethoxyphenyl)thio]piperidine,
(b) 3-[(3,4-dimethoxyphenyl)sulfonyl]piperidine,
(c) 3-[(3,5-dimethoxyphenyl)sulfonyl]piperidine, and (d) 3-[(3,4,5-trimethoxyphenyl)sulfonyl]piperidine.

INTERMEDIATE 33

2-[[(4-Chlorophenyl)sulfonyl]methyl]piperidine monohydrochloride

A mixture of 45.1 g (0.109 mole) of 2-[[(4-chlorophenyl)sulfonyl]methyl]-1-phenylsulfonylpiperidine and 200 ml of phenol in 200 ml of 48% hydrobromic acid was refluxed for 1 hr. The reaction mixture was quenched in water and 50% sodium hydroxide was added until the solution was basic (pH<10). The mixture was extracted with methylene chloride. The methylene chloride phase was separated, extracted with dilute aqueous sodium hydroxide followed by several portions of dilute sulfuric acid. The acidic phase was separated, basified with solid sodium carbonate and extracted with methylene chloride. This methylene chloride solution was dried over sodium sulfate and evaporated to remove solvent in vacuo to give an oil, the free base of the title compound. The free base was dissolved in methanol and converted to the hydrochloride salt with ethereal hydrogen chloride and the salt was recrystallized from methanol-diethyl ether to give 22.82 g (67.5%) white crystalline solid, m.p. 223.5°–224.5° C.

Analysis: Calculated for $C_{12}H_{17}NO_2SCl_2$: C, 46.46; H, 5.52; N, 4.52. Found: C, 46.40; H, 5.45; H, 4.55

INTERMEDIATE 34

4-[(4-Methoxyphenyl)sulfonyl]piperidine monohydrochloride

A solution of 1.12 g (0.0038 mole) of 4-[(4-chlorophenyl)sulfonyl]piperidine monohydrochloride and 0.0152 mole of sodium methoxide in 60 ml of dimethylsulfoxide was heated at 90° C. for 2 hrs. The reaction mixture was quenched in water and diluted mixture was extracted with methylene chloride. The methylene chloride phase was dried over sodium sulfate and the solvent was removed on the rotary evaporator. The residue (the free base of the title compound) was dissolved in methanol and the solution was treated with an excess of ethereal hydrogen chloride. The resulting hydrochloride salt was recrystallized from methanol-diethyl ether to give white crystalline solid, m.p. 275°–276° C.

Analysis: Calculated for $C_{12}H_{18}NO_3SCl$: C, 49.40; H, 6.27; N, 4.80; Found: C, 49.19; H, 6.12; N, 4.81

INTERMEDIATE 35

4-[(2,5-Dichlorophenyl)thio]piperidine monohydrochloride

A mixture of 200 g (2.13 mole) of phenol, 200 ml of 48% hydrobromic acid and 21.86 g (0.053 mole) of 4-[(2,5-dichlorophenyl)thio]-1-[(4-methylphenyl)sulfonyl]piperidine were heated at reflux for 1.5 hr. The reaction mixture was diluted to 2 liters volume with ice water and made alkaline with 50% sodium hydroxide. The aqueous layer was extracted with diethyl ether. The ether phase was extracted with 1N sulfuric acid. The resulting aqueous acidic phase was extracted with methylene chloride. The methylene chloride phase was dried, filtered and evaporated to remove solvent to give a brown oil, the free base of the title compound. The free base was converted to 9.36 g (59.1%) of a white crystalline hydrochlorid esalt as in Intermediate 33, m.p. 198°–200° C.

Analysis: Calculated for $C_{11}H_{14}Cl_3NS$: C, 44.24; H, 4.73; N, 4.69; Found: C, 44.34; H, 4.65; N, 4.67

INTERMEDIATE 36

4-[(4-methylphenyl)thio]piperidine monohydrochloride

A mixture of 100 ml of 48% hydrobromic acid, 23.50 g (0.25 mole) of phenol and 39.85 g (0.11 moles) of 4-[(4-methylphenyl)thio]-1-phenylsulfonylpiperidine were heated at reflux for 1.5 hr. The reaction mixture was cooled to room temperature, diluted to 1 liter volume with ice water and made alkaline with 50% sodium hydroxide. The alkaline solution was extracted with diethyl ether. The ether phase was extracted with 1N sulfuric acid. The resulting acidic phase was separated and made alkaline and extracted with methylene chloride. The methylene chloride layer was dried over sodium sulfate, filtered and evaporated to give a light yellow oil, the free base of the title compound. The free base was converted to 11.52 g (43%) of a white crystalline hydrochloride salt as in Intermediate 33, m.p. 169°–174° C.

Analysis: Calculated for $C_{12}H_{18}ClNS$: C, 59.12; H, 7.44; N, 5.74; Found: C, 58.78; H, 7.46; N, 5.72

INTERMEDIATE 37

4-(Phenylthio)-piperidine monohydrochloride

A mixture of 68.23 g (0.20 mole) of 1-[(4-methylphenyl)sulfonyl]-4-(phenylthio)piperidine, 43.3 g (0.46 mole) of phenol and 200 ml of 48% hydrobromic acid was heated at reflux for 1.5 hr. The reaction mixture was cooled to room temperature and diluted with water. The aqueous solution was made alkaline with 50% sodium hydroxide. The aqueous mixture was extracted with diethyl ether and the resulting ether layer was extracted with 1N sulfuric acid. The aqueous acidic layer was made alkaline and extracted with benzene. The benzene layer was dried over sodium sulfate, filtered and evaporated to give an oil, the free base of the title compound in 60% yield. The free base was converted to a white crystalline hydrochloride salt as in Intermediate 33, m.p. 159°–161° C.

Analysis: Calculated for $C_{11}H_{16}ClNS$: C, 57.50; H, 7.02; N, 6.10; Found: C, 57.44; H, 7.08; N, 6.13

INTERMEDIATE 38

4-[(2-Chlorophenyl)thio]piperidine monohydrochloride

A mixture of 88.76 g (0.23 mole) of 4-[(2-chlorophenyl)thio]-1-[(4-methylphenyl)sulfonyl]piperidine, 47.0 g (0.50 mole) of phenol and 200 ml of 48% hydrobromic acid was refluxed for 1.5 hr. The reaction mixture was cooled to room temperature and diluted with ice water. The mixture was made alkaline with 50% sodium hydroxide and extracted with diethyl ether. The ether phase was extracted with 1N sulfuric acid. The acidic layer was made alkaline and extracted with methylene chloride. The methylene chloride layer was dried over sodium sulfate, filtered and evaporated to give an oil, the free base of the title compound. The free base was converted to 4.30 g (36.5%) of a white crystalline hydrochloride salt, m.p. 202°–210° C.

Analysis: Calculated for $C_{11}H_{15}Cl_2NS$: C, 50.01; H, 5.72; N, 5.30; Found: C, 50.28; H, 5.73; N, 5.32

INTERMEDIATE 39

4-[(3-Chlorophenyl)thio]piperidine maleate [1:1]

A suspension of 8.66 g (0.0227 mole) of 4-[(3-chlorophenyl)thio]-1-[(4-methylphenyl)sulfonyl]piperidine and 40 ml of phenol in 75 ml of 48% hydrobromic acid was refluxed for 1.5 hr. The reaction mixture was quenched in water and basified with 50% sodium hydroxide. The solution was extracted with several portions of methylene chloride. The methylene chloride extract was dried over magnesium sulfate and evaporated to an oil, the free base of the title compound. The free base was dissolved in methanol, treated with maleic acid and diethyl ether was added to give 3.13 g (40%) of a white, crystalline maleate salt, m.p. 116.0°–116.5° C.

Analysis: Calculated for $C_{15}H_{18}ClNO_4S$: C, 52.40; H, 5.28; N, 4.07; Found: C, 52.37; H, 5.33; N, 4.12

INTERMEDIATE 40

4-[(3,4-Dichlorophenyl)thio]piperidine Monohydrobromide

A solution of 20.84 g (0.0502 mole) of 4-[(3,4-dichlorophenyl)thio]-1-[(4-methylphenyl)sulfonyl]-piperidine, 36.58 g (0.338 mole) of phenol and 200 ml of 48% hydrobromic acid was heated at reflux for 25 hr. The reaction mixture was cooled to room temperature and diluted with water. The aqueous phase was extracted with benzene. The resulting aqueous acidic phase was made alkaline with 10% aqueous sodium hydroxide and extracted with chloroform. The chloroform layer was dried over sodium sulfate, filtered and evaporated to give a residue, the free base of the title compound. The free base was converted to the hydrobromide salt. The salt was recrystallized from methylene chloride-methanol diethyl ether to give 3.6 g (4.4%) of white solid, m.p. 125°–128° C.

Analysis: Calculated for $C_{11}H_{14}BrCl_2NS$: C, 38.51; H, 4.11; N, 4.08; Found: C, 38.31; H, 4.08; N, 4.11

INTERMEDIATE 41

3-[(2-Chlorophenyl)thio]piperidine Hydrobromide

A solution of 51.13 g (0.125 mole) of 3-phenylsulfonic acid ester with 1-[(4-methylbenzene)sulfonyl]-3-piperidinol, 25.2 g (0.175 mole) of o-chlorothiophenol and 58 g of sodium carbonate in dimethylformamide was heated at 100° C. for 19 hr and then was quenched in 1 liter of dilute sodium hydroxide. The mixture was extracted with several portions of methylene chloride. The combined methylene chloride extract was washed with several portions of 1M sodium hydroxide, dried over magnesium sulfate and evaporated in vacuo to give an oil which was shown by NMR and mass spectroscopy to e N-tosyl-3-(o-chlorothiophenoxy)piperidine. A mixture of the oil and excess phenol in 200 ml of 48% hydrobromic acid was refluxed for 1.5 hr. The reaction mixture was quenched in ice water, made basic with sodium hydroxide and extracted with several portions of methylene chloride. The combined methylene chloride extract was dried over magnesium sulfate and evaporated in vacuo to give an oil, the free base of the title compound. The free base was converted to the hydrobromic acid salt which was recrystallized from isopropanol-acetonitrile-isopropyl ether, m.p. 152.5°–154.5° C.

Analysis: Calculated for $C_{11}H_{15}BrClNS$: C, 42.80; H, 4.90; N, 4.54; Found: C, 43.17; H, 4.98; N, 4.64

INTERMEDIATE 42

4-[(4-Fluorophenyl)thio]piperidine Monohydrochloride Hydrate [4:1]

A mixture of 37.74 g (0.103 mole) of 4-[(4-fluorophenyl)thio]-1-[(4-methylphenyl)sulfonyl]piperidine and 40 g of phenol in 250 ml of 48% hydrobromic acid was refluxed for 1.5 hr. The reaction mixture was quenched in 800 ml of water. The diluted aqueous mixture was extracted with three portions of benzene and the benzene extracts were discarded. The aqueous layer was made basic with 50% sodium hydroxide and extracted with several portions of methylene chloride. The combined methylene chloride extracts were dried over magnesium sulfate and evaporated in vacuo to give an oil, the free base of the title compound, which crystallized on standing. The free base was converted to 5.57 g (21%) of the white hydrochloride salt as in Intermediate 33, m.p. 166°–167° C.

Analysis: Calculated for $C_{11}H_{15}FNSCl.\frac{1}{4}H_2O$: C, 52.37; H, 6.19; N, 5.55; Found C, 52.49; H, 6.05; N, 5.55

INTERMEDIATE 43

2-[[(4-Chlorophenyl)thio]methyl]piperidine Monohydrobromide

A solution of 2-[[(4-chlorophenyl)thio]methyl]-1-[(4-methylphenyl)sulfonyl]piperidine and excess phenol in 48% hydrobromic acid was refluxed for 1.5 hr and then poured over ice. The mixture was made basic with 50% sodium hydroxide and extracted with several portions of methylene chloride. The combined methylene chloride extract was dried over magnesium sulfate and the volume reduced to about 100 ml. Excess hydrogen bromide was bubbled into the solution for 2 minutes. The solvent was removed in vacuo to give an oil which was crystallized from isopropanol-isopropyl ether to give the white hydrobromide salt, m.p. 121°–123° C.

Analysis: Calculated for $C_{12}H_{17}BrClNS$: C, 44.67; H, 5.31; N, 4.34; Found: C, 44.76; H, 5.42; N, 4.46

INTERMEDIATE 44

4-(Phenylsulfinyl)piperidine maleate [1:1]

A solution of 20.0 g (0.104 mole) of (4-phenylthio)-piperidine and excess sodium perborate in 400 ml of dilute hydrochloric acid was stirred at room temperature overnight. The solution was made basic with 50% sodium hydroxide and extracted with methylene chloride. The methylene chloride solution was dried over magnesium sulfate and evaporated to give an oil, the free base of the title compound. The free base was reacted with maleic acid and the maleate salt was recrystallized from methanol-diethyl ether to give a white solid, m.p. 187°–188° C.

Analysis: Calculated for $C_{15}H_{19}NO_5S$: C, 55.37; H, 5.89; N, 4.31; Found: C, 55.02; H, 5.81; N, 4.29

INTERMEDIATE 45

3-[(Phenylthio)methyl]piperidine monohydrochloride

A mixture of 8.92 g (0.0255 mole) of 1-[(4-methylphenyl)sulfonyl]-3-[(phenylthio)methyl]piperidine and 20 ml of phenol in 100 ml of 48% hydrobromic acid was refluxed for several hours. The mixture was poured over ice. The resulting aqueous solution was extracted with several portions of benzene, which extracts were discarded. The aqueous phase was made basic with 50% sodium hydroxide and extracted with several portions of methylene chloride. The combined methylene chloride extracts were dried over magnesium sulfate and evporated in vacuo to give an oil, the free base of the title compound. The free base was dissolved in methanol and treated with excess ethereal hydrogen chloride to give, after recrystallizing from methylene chloride-diethyl ether, 5.57 g (21%) of white hydrochloride salt, m.p. 166°–167° C.

Analysis: Calculated for $C_{12}H_{18}ClNS$: C, 59.12; H, 7.44; N, 5.75; Found: C, 58.82; H, 7.44; N, 5.65

INTERMEDIATE 46

4-[(Phenylmethyl)thio]piperidine maleate

1-[(4-Methylphenyl)sulfonyl]-4-[(phenylmethyl)thio]piperidine, phenol and 48% hydrobromic acid are refluxed together for about 2 hr. The reaction mixture is worked up as in Intermediate 39 to give the free base which is then converted to the maleate salt.

INTERMEDIATE 47

2-[[(4-Chlorophenyl)thio]methyl]piperidine maleate

2-[[(4-Chlorophenyl)thio]methyl]-1-[(4-methylphenyl)sulfonyl]piperidine, phenol and 48% hydrobromic acid are refluxed together for about 2 hr. The reaction mixture is worked up as in Intermediate 39 to give the free base which is then converted to the maleate salt.

INTERMEDIATE 48

4-[(Phenylmethyl)sulfonyl]piperidine maleate

4-[(Phenylmethyl)thio]piperidine is oxidized by heating with excess sodium perborate in acid solution. The solution is basified, extracted with methylene chloride and the methylene chloride evaporated to give the free base of the title compound. The free base is then reacted with maleic acid to obtain the meleate salt.

INTERMEDIATE 49

3-(Phenylthio)piperidine maleate

Preparation of ditosylated 3-piperidinol

A mixture of 99 g (0.719 mole) of 3-hydroxypiperidine hydrochloride and 310 g (1.62 mole) of tosyl chloride in 2 liters of pyridine was stirred overnight at 25° C. The reaction was quenched in water and the aqueous mixture was extracted with several portions of methylene chloride. The combined methylene chloride extract was extracted with several portions of 2M sulfuric acid followed by aqueous dilute sodium hydroxide and evaporated in vacuo to give an oil, 4-methylphenylsulfonic acid ester with 1-[(4-methylbenzene)sulfonyl-3-piperidinol.

Preparation of 3-phenylthio-1-[(4-methylphenyl)sulfonyl]piperidine

A mixture of the oil; i.e., the 1-[(4-methylphenyl)sulfonyl] 3 piperidinol-4-methylphenyl sulfonate ester, 110 g (1.0 mole) of thiophenol and excess sodium carbonate in 1.5 liter of dimethylformamide was stirred at 90° C. for 16 hr. The reaction was quenched in dilute sodium hydroxide and the mixture was extracted with methylene chloride. The methylene chloride extract was extracted with several portions of dilute sodium hydroxide, dried over magnesium sulfate and evaporated in vacuo to give an oil. $^1$H NMR ($CDCl_3$) showed this to be an 80/20 mixture of N-tosyl-3-(phenylthio)piperidine and N-tosyl-1,2,3,6-tetrahydropyridine, respectively.

Preparation of 3-(phenylthio)piperidine maleate

The above mixture was suspended in 600 ml of 48% hydrobromic acid and excess phenol. The suspension was refluxed for 1 hr and was cooled to room temperature. The reaction mixture was made basic with 50% aqueous sodium hydroxide and the basic solution was extracted with methylene chloride. The methylene chloride extract was extracted with 2M sulfuric acid. The acidic aqueous phase was made basic with 50% sodium hydroxide and the basic solution was extracted with methylene chloride. This last methylene chloride solution was dried over magnesium sulfate and the solvent was removed in vacuo to give the free base: 3-(phenylthio)piperidine as an oil. The free base was reacted with maleic acid and the maleate salt was recrystallized from methanol-diethyl ether as white crystals, m.p. 117°–119° C.

Analysis: Calculated for $C_{15}H_{19}NO_4S$: C, 58.23; H, 6.19; N, 4.53; Found: C, 58.22; H, 6.24; N, 4.47

INTERMEDIATE 50

4-(Phenylthio)piperidine hydrochloride

A solution of 1-(diphenylmethyl)-4-(phenylthio)piperidine and a one-half excess of phenyl chloroformate in methylene chloride is stirred at room temperature for about 3 hr. The diphenylmethane is filtered off and the product obtained as in Intermediate 9 after hydrolysis with hydrobromic acid isolation and conversion to the hydrochloride salt.

INTERMEDIATE 51

4-[(4-Chlorophenyl)thio]piperidine hydrochloride

Following the procedure of Intermediate 9, 4-[(4-chlorophenyl)thio]-1-(phenylmethyl)piperidine is reacted with phenyl chloroformate and the product is hydrolyzed with 48% hydrobromic acid to give the free base of the title compound which is then converted to the hydrochloride.

INTERMEDIATE 52

3-[4-(Cyanophenyl)sulfonyl]piperidine

3-[(4-chlorophenyl)-sulfonyl]piperidine is reacted with cupric cyanide to give the title compound.

INTERMEDIATE 53

3-[[(4-Aminocarbonyl)phenyl]sulfonyl]piperidine

3-[4-(Cyanophenyl)sulfonyl]piperidine is hydrolyzed with sulfuric acid to give the title compound.

INTERMEDIATE 54

3-[[4-[(N,N-diethylamino)carbonyl)]-phenyl]sulfonyl]-piperidine

3-[[(4-Aminocarbonyl)-phenyl]sulfonyl]piperidine and excess diethylamine are heated in a closed bomb overnight at 100° C.

INTERMEDIATE 55

4-(Phenylthio)homopiperidine Hydrochloride

Following the procedure of Intermediate 45 and substituting 1-[(4-methylphenyl)sulfonyl]-4-(phenylthio)-homopiperidine for 1-[(4-methylphenyl)sulfonyl]-3-[(phenylthio)methyl]piperidine, the title compound is obtained.

INTERMEDIATE 56

3-(Phenylthio)homopiperidine Hydrochloride

Following the procedure of Intermediate 45 and substituting 1-[(4-methylphenyl)sulfonyl]-3-(phenylthio)-homopiperidine for 1-[(4-methylphenyl)sulfonyl]-3-[(phenylthiomethyl]piperidine, the title compound is obtained.

INTERMEDIATE 57

4-(Phenylthio)homopiperidine

Following an analogous procedure to that of Sasatani, S. et al. described in Tetrahedron Letters, Vol. 24 (No. 43), pp 4711–4712 (1982), 4-phenylthiocyclohexanone oxime is reacted with diisobutyl aluminum hydride in methylene chloride to give the title compound.

INTERMEDIATE 58

4-(Phenylsulfonyl)homopiperidine

Following the procedure of Preparation 21, 1-[(4-methylphenyl)sulfonyl]-4-(phenylthio)homopiperidine is treated with an excess of metachloroperoxybenzoic acid in methylene chloride and the resulting 1-[(4-methylphenyl)sulfonyl]-4-(phenylsulfonyl)homopiperidine is isolated and reacted with 48% hydrobromic acid in phenol to give the title compound.

TABLE I

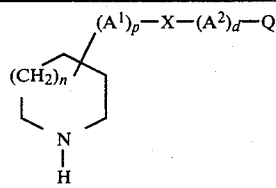

| Intermediate No. | n | Position of $-(A^1)_p-X-(A^2)_d-Q$ | $(A^1)_p$ | X | $(A^2)_d$ | Q | Salt |
|---|---|---|---|---|---|---|---|
| 1 | 0 | 3-pyrrolidinyl | — | —S— | — | 4-Cl—$C_6H_4$— | maleate |
| 2 | 0 | 3-pyrrolidinyl | — | —S(O)— | — | 4-Cl—$C_6H_4$— | maleate |
| 3 | 0 | 3-pyrrolidinyl | — | —S(O)$_2$— | — | 4-Cl—$C_6H_4$— | HCl |
| 4 | 0 | 3-pyrrolidinyl | — | —S(O)$_2$— | — | $C_6H_5$— | maleate |
| 5 | 0 | 3-pyrrolidinyl | — | —S(O)$_2$— | — | 4-OCH$_3$—$C_6H_4$— | HCl |
| 6 | 0 | 3-pyrrolidinyl | — | —S— | — | 4-CH$_3$—$C_6H_4$— | maleate |
| 7 | 0 | 3-pyrrolidinyl | — | —S(O)$_2$ | — | 4-CH$_3$—$C_6H_4$— | HCl |
| 8 | 0 | 3-pyrrolidinyl | — | —S(O)$_2$— | — | 3,4-Cl$_2$—$C_6H_3$— | HCl |
| 9 | 0 | 3-pyrrolidinyl | — | —S— | — | 3,4-Cl$_2$—$C_6H_3$— | HCl.½ H$_2$O |
| 10 | 1 | 3-piperidinyl | — | —S— | — | 3-Cl—$C_6H_4$— | HBr |
| 11 | 1 | 3-piperidinyl | — | —S— | — | 4-Cl—$C_6H_4$— | HCl |
| 12 | 1 | 3-piperidinyl | — | —S(O)$_2$— | — | 4-Cl—$C_6H_4$— | fumarate |
| 13 | 1 | 3-piperidinyl | — | —S(O)$_2$— | — | $C_6H_5$— | maleate |
| 14 | 1 | 3-piperidinyl | — | —S(O)— | — | 4-Cl—$C_6H_4$— | maleate |
| 15 | 1 | 3-piperidinyl | — | —S(O)$_2$— | — | 3-Cl—$C_6H_4$— | HCl |
| 16 | 1 | 3-piperidinyl | — | —S(O)$_2$— | — | 4-CH$_3$—$C_6H_4$ | maleate |
| 17 | 1 | 3-piperidinyl | — | —S(O)$_2$— | — | 4-F—$C_6H_4$— | maleate |
| 18 | 1 | 3-piperidinyl | — | —S(O)$_2$— | — | 4-OCH$_3$—$C_6H_4$— | maleate |
| 19 | 1 | 4-piperidinyl | — | —S— | — | 4-Cl—$C_6H_4$— | HCl.½ H$_2$O |
| 20 | 1 | 4-piperidinyl | — | —S(O)$_2$— | — | 4-Cl—$C_6H_4$— | HCl |
| 21 | 1 | 4-piperidinyl | — | —S(O)— | — | 4-Cl—$C_6H_4$— | HCl |
| 22 | 1 | 3-piperidinyl | — | —S(O)$_2$— | — | 4-[OCH$_2$CH$_2$N(CH$_3$)$_2$]—$C_6H_4$— | di-maleate |
| 23 | 1 | 3-piperidinyl | — | —S(O)$_2$— | — | 4-[OCH$_2$CH$_2$N(C$_2$H$_5$)$_2$]—$C_6H_4$— | di-maleate |
| 24 | 1 | 3-piperidinyl | — | —S(O)$_2$— | — | 4-(OCH$_2$CH$_2$OCH$_3$)—$C_6H_4$— | HCl |
| 25 | 1 | 3-piperidinyl | —CH$_2$— | —S(O)$_2$— | — | $C_6H_5$— | HCl |
| 26a | 1 | 3-piperidinyl | — | —S(O)$_2$— | — | 1-naphthyl | HCl |
| b | 1 | 3-piperidinyl | — | —S(O)$_2$— | — | 2-naphthyl | HCl |
| c | 1 | 3-piperidinyl | — | —S(O)$_2$— | — | 2,3-dihydro-1H—inden-4-yl | HCl |
| d | 1 | 3-piperidinyl | — | —S(O)$_2$— | — | 2,3-dihydro-1H—inden-5-yl | HCl |
| e | 1 | 3-piperidinyl | — | —S(O)$_2$— | — | 4-biphenyl | HCl |
| f | 1 | 3-piperidinyl | — | —S(O)$_2$— | — | 4-F—$C_6H_4$— | HCl |
| g | 1 | 3-piperidinyl | — | —S(O)$_2$— | — | 4-CN—$C_6H_4$— | HCl |
| h | 1 | 3-piperidinyl | — | —S(O)$_2$— | — | 4-NO$_2$—$C_6H_4$— | HCl |
| i | 1 | 3-piperidinyl | — | —S(O)$_2$— | — | 4-(CH$_3$)$_2$N—$C_6H_4$— | HCl |
| j | 1 | 3-piperidinyl | — | —S(O)$_2$— | — | 4-(CH$_3$)$_2$N—C(O)—$C_6H_4$— | HCl |
| k | 1 | 3-piperidinyl | — | —S(O)$_2$— | — | 4-[—S(CH$_2$)$_2$N(C$_2$H$_5$)$_2$]—$C_6H_4$— | HCl |
| l | 1 | 3-piperidinyl | — | —S(O)$_2$— | — | 4-[—S(O)$_2$(CH$_2$)$_2$—N(C$_2$H$_5$)$_2$]—$C_6H_4$ | HCl |
| m | 1 | 3-piperidinyl | — | —S(O)$_2$— | — | 4-[—(CH$_2$)$_2$N(C$_2$H$_5$)$_2$]—$C_6H_4$— | HCl |
| n | 1 | 3-piperidinyl | — | —S(O)$_2$— | — | 4-SCH$_3$—$C_6H_4$— | HCl |
| o | 1 | 3-piperidinyl | — | —S(O)$_2$— | — | 4-[—S(O)$_2$CH$_3$]—$C_6H_4$— | HCl |
| p | 1 | 3-piperidinyl | — | —S(O)$_2$— | — | 4-(—SC$_6$H$_5$)—$C_6H_4$— | HCl |
| q | 1 | 3-piperidinyl | — | —S(O)$_2$— | — | 4-CF$_3$—$C_6H_4$— | HCl |
| r | 1 | 3-piperidinyl | — | —S(O)$_2$— | — | 4-Br—$C_6H_4$— | HCl |
| s | 1 | 3-piperidinyl | — | —S(O)$_2$— | — | 4-I—$C_6H_4$— | HCl |
| 27a | 1 | 3-piperidinyl | — | —S(O)$_2$— | — | 4-[S(O) (CH$_2$)$_2$N(C$_2$H$_5$)$_2$—$C_6H_4$— | HCl |
| b | 1 | 3-piperidinyl | — | —S(O)$_2$— | — | 4-S(O)—CH$_3$—$C_6H_4$— | HCl |
| 28a | 1 | 3-piperidinyl | — | —S(O)$_2$— | — | 2,3-(CH$_3$)$_2$—$C_6H_3$— | HCl |
| b | 1 | 3-piperidinyl | — | —S(O)$_2$— | — | 2,4-(CH$_3$)$_2$—$C_6H_3$— | HCl |
| c | 1 | 3-piperidinyl | — | —S(O)$_2$— | — | 2,3,5-(CH$_3$)$_3$—$C_6H_2$— | HCl |
| d | 1 | 3-piperidinyl | — | —S(O)$_2$— | — | 2,4,6-(CH$_3$)$_3$—$C_6H_2$— | HCl |
| e | 1 | 3-piperidinyl | — | —S(O)$_2$— | — | 4-t-Bu—$C_6H_4$— | HCl |
| f | 1 | 3-piperidinyl | — | —S(O)$_2$— | — | 2-CH$_3$—4-C$_2$H$_5$—$C_6H_3$— | HCl |

TABLE I-continued $$(A^1)_p\text{—}X\text{—}(A^2)_d\text{—}Q$$

structure: piperidine ring with $(CH_2)_n$ and substituent $(A^1)_p$—X—$(A^2)_d$—Q, NH

| Intermediate No. | n | Position of —$(A^1)_p$—X—$(A^2)_d$—Q | $(A^1)_p$ | X | $(A^2)_d$ | Q | Salt |
|---|---|---|---|---|---|---|---|
| 29a | 1 | 3-piperidinyl | — | —S(O)$_2$— | — | 2,4-(OCH$_3$)—C$_6$H$_3$— | — |
| b | 1 | 3-piperidinyl | — | —S(O)$_2$— | — | 2,4-(OC$_2$H$_5$)$_2$—C$_6$H$_3$— | — |
| c | 1 | 3-piperidinyl | — | —S(O)$_2$— | — | 3-Cl—4-OCH$_3$—C$_6$H$_3$— | — |
| d | 1 | 3-piperidinyl | — | —S(O)$_2$— | — | 3-Cl—5-OCH$_3$—C$_6$H$_3$— | — |
| e | 1 | 3-piperidinyl | — | —S(O)$_2$— | — | 2,6-(OCH$_3$)$_2$—C$_6$H$_3$— | — |
| f | 1 | 3-piperidinyl | — | —S(O)$_2$— | — | 3-Cl—4,5-(OCH$_3$)$_2$—C$_6$H$_2$— | — |
| g | 1 | 3-piperidinyl | — | —S(O)$_2$— | — | 4-(n-butoxy)-C$_6$H$_4$ | — |
| h | 1 | 3-piperidinyl | — | —S(O)$_2$— | — | 2-CH$_3$—4-(OCH$_3$)—C$_6$H$_3$— | — |
| i | 1 | 3-piperidinyl | — | —S(O)$_2$— | — | 2-CH$_3$—4-(OC$_2$H$_5$)—C$_6$H$_5$ | — |
| 30a | 1 | 3-piperidinyl | — | —S(O)$_2$ | — | 2-Cl—6-NO$_2$—C$_6$H$_3$— | HCl |
| b | 1 | 3-piperidinyl | — | —S(O)$_2$— | — | 2-NO$_2$—3Cl—C$_6$H$_3$— | HCl |
| c | 1 | 3-piperidinyl | — | —S(O)$_2$— | — | 3-Cl—4-NO$_2$—C$_6$H$_3$— | HCl |
| d | 1 | 3-piperidinyl | — | —S(O)$_2$— | — | 2-NO$_2$—4-Cl—C$_6$H$_3$— | HCl |
| e | 1 | 3-piperidinyl | — | —S(O)$_2$— | — | 3-Cl—5-NO$_2$—C$_6$H$_3$— | HCl |
| f | 1 | 3-piperidinyl | — | —S(O)$_2$— | — | 3-NO$_2$—4-Cl—C$_6$H$_3$— | HCl |
| g | 1 | 3-piperidinyl | — | —S(O)$_2$— | — | 2-NO$_2$—5-Cl—C$_6$H$_3$— | HCl |
| h | 1 | 3-piperidinyl | — | —S(O)$_2$— | — | 3-Cl—4-SCH$_3$—C$_6$H$_3$ | HCl |
| i | 1 | 3-piperidinyl | — | —S(O)$_2$— | — | 3-Cl—4-(SC$_6$H$_5$)—C$_6$H$_3$— | HCl |
| 31a | 1 | 3-piperidinyl | —CH$_2$— | —S(O)$_2$— | — | 3-Cl—C$_6$H$_4$— | HCl |
| b | 1 | 3-piperidinyl | —CH$_2$— | —S(O)$_2$— | — | 1-naphthyl | HCl |
| c | 1 | 3-piperidinyl | —CH$_2$— | —S(O)$_2$— | — | 2,3-dihydro-1H—inden-4-yl | HCl |
| d | 1 | 3-piperidinyl | —(CH$_2$)$_2$— | —S(O)$_2$— | — | -3-Cl—C$_6$H$_4$— | HCl |
| 32a | 1 | 3-piperidinyl | — | —S— | — | 3,4-(OCH$_3$)$_2$—C$_6$H$_3$— | — |
| b | 1 | 3-piperidinyl | — | —S(O)$_2$— | — | 3,4-(OCH$_3$)$_2$—C$_6$H$_3$— | — |
| c | 1 | 3-piperidinyl | — | —S(O)$_2$— | — | 3,5-(OCH$_3$)$_2$—C$_6$H$_3$— | — |
| d | 1 | 3-piperidinyl | — | —S(O)$_2$— | — | 3,4,5-(OCH$_3$)$_3$—C$_6$H$_3$— | — |
| 33 | 1 | 2-piperidinyl | —CH$_2$— | —S(O)$_2$— | — | 4-Cl—C$_6$H$_4$— | HCl |
| 34 | 1 | 4-piperidinyl | — | —S(O)$_2$— | — | 4-OCH$_3$—C$_6$H$_4$— | HCl |
| 35 | 1 | 4-piperidinyl | — | —S— | — | 2,5-Cl$_2$—C$_6$H$_3$— | HCl |
| 36 | 1 | 4-piperidinyl | — | —S— | — | 4-CH$_3$—C$_6$H$_4$— | HCl |
| 37 | 1 | 4-piperidinyl | — | —S— | — | C$_6$H$_5$— | HCl |
| 38 | 1 | 4-piperidinyl | — | —S— | — | 2-Cl—C$_6$H$_4$— | HCl |
| 39 | 1 | 4-piperidinyl | — | —S— | — | 3-Cl—C$_6$H$_4$— | maleate |
| 40 | 1 | 4-piperidinyl | — | —S— | — | 3,4-Cl$_2$—C$_6$H$_3$— | HBr |
| 41 | 1 | 3-piperidinyl | — | —S— | — | 2-Cl—C$_6$H$_4$— | HBr |
| 42 | 1 | 4-piperidinyl | — | —S— | — | 4-F—C$_6$H$_4$— | HCl.½ H$_2$O |
| 43 | 1 | 2-piperidinyl | —CH$_2$— | —S— | — | 4-Cl—C$_6$H$_4$— | HBr |
| 44 | 1 | 4-piperidinyl | — | —S(O)— | — | C$_6$H$_5$— | maleate |
| 45 | 1 | 3-piperidinyl | —CH$_2$— | —S— | — | C$_6$H$_5$ | HCl |
| 46 | 1 | 4-piperidinyl | — | —S— | —CH$_2$— | C$_6$H$_5$— | maleate |
| 47 | 1 | 2-piperidinyl | —CH$_2$— | —S— | — | 4-Cl—C$_6$H$_4$—, | maleate |
| 48 | 1 | 4-piperidinyl | — | —S(O)$_2$— | —CH$_2$— | C$_6$H$_5$ | maleate |
| 49 | 1 | 3-piperidinyl | — | —S— | — | C$_6$H$_5$ | maleate |
| 50 | 1 | 4-piperidinyl | — | —S— | — | C$_6$H$_5$— | HCl |
| 51 | 1 | 4-piperidinyl | — | —S— | — | 4-Cl—C$_6$H$_4$— | HCl |
| 52 | 1 | 3-piperidinyl | — | —S(O)$_2$— | — | 4-CN—C$_6$H$_4$— | — |
| 53 | 1 | 3-piperidinyl | — | —S(O)$_2$— | — | 4-C(O)NH$_2$—C$_6$H$_4$— | — |
| 54 | 1 | 3-piperidinyl | — | —S(O)$_2$— | — | 4-C(O)N(C$_2$H$_5$)$_2$—C$_6$H$_4$— | — |
| 55 | 2 | 4-homopiperidinyl | — | —S— | — | C$_6$H$_5$— | HCl |
| 56 | 2 | 3-homopiperidinyl | — | —S— | — | C$_6$H$_5$— | HCl |
| 57 | 2 | 4-homopiperidinyl | — | —S— | — | C$_6$H$_5$— | — |
| 58 | 2 | 4-homopiperidinyl | — | —SO$_2$— | — | C$_6$H$_5$— | — |

The following Examples 1–70 serve to illustrate the the preparation of the novel compounds of Formula I, useful composition in treating arrhythmias in the method of this invention. The scope of the invention as it pertains to the Formula I compounds is not, however, limited thereto. Structures are illustrated in Table 2.

EXAMPLE 1

3-[4-(Chlorophenyl)thio]-N-[2-(diethylamino)ethyl]-1-pyrrolidinecarboxamide Citrate [1:1]

A solution of 5.51 g (0.034 mole) of 1,1'-carbonyldiimidazole and 3.91 g (0.033 mole) of N,N-diethylaminoethylamine in 100 ml of tetrahydrofuran was stirred at room temperature for 1.5 hr. A solution of 6.1 g (0.0286 mole) of 3-[(4-chlorophenyl)thio]pyrrolidine (free base) in 100 ml of tetrahydrofuran was added and the solution was refluxed for 19 hr. The solvent was removed in vacuo, and the resulting oil was dissolved in methylene chloride and the solution was extracted with water. The methylene chloride phase was evaporated to give an oil. The oil was dissolved in diethyl ether and the solution was extracted with several portions of water. The ether layer was dried over magnesium sulfate and the solvent was removed in vacuo to give an oil, the free base of the title compound. The free base was converted to the citrate and the salt was recrystallized from methanol-diethyl ether to give 13.65 g (87.1%) of white crystalline solid, m.p. 140°–142° C.

Analysis: Calculated for $C_{23}H_{34}N_3O_8SCl$: C, 50.41; H, 6.25; N, 7.67; Found: C, 50.20; H, 6.25; N, 7.60

EXAMPLE 2

3-[(4-Chlorophenyl)thio]-N-[2-(dimethylamino)ethyl]-1-pyrrolidinecarboxamide

A solution of 5.20 g (0.032 mole) of 1,1'-carbonyldiimidazole and 2.73 g (0.031 mole) of N,N-dimethylaminoethylamine in 200 ml of tetrahydrofuran was stirred at room temperature for 50 min. A solution of 5.63 g (0.0264 mole) of 3-[(4-chlorophenyl)thio]pyrrolidine (free base) in tetrahydrofuran was added and the solution was refluxed for about 66 hr. The solvent was removed in vacuo and the resulting oil was dissolved in methylene chloride. The methylene chloride solution was extracted with several portions of water and was dried over magnesium sulfate. The solvent was removed in vacuo and the resulting solid was recrystallized from methylene chloride-diethyl ether-hexane to give 6.03 g (69.7%) of white crystals, m.p. 97°–98.5° C.

Analysis: Calculated for $C_{15}H_{22}N_3OSCl$: C, 54.95; H, 6.76; N, 12.82; Found: C, 54.94; H, 6.76; N, 12.97

EXAMPLE 3

3-[(4-Chlorophenyl)thio]-N-[2-(dimethylamino)ethyl]-1-pyrrolidinecarboxamide Oxalate [1:1]

The free base of the title compound as prepared in Example 2 was reacted with oxalic acid in methyl alcohol, the salt was precipitated with diethyl ether and recrystallized from methanol-diethyl ether as white crystals in yield of 69.8%, m.p. 122°–124° C.

Analysis: Calculated for $C_{17}H_{24}N_3O_5SCl$: C, 48.86; H, 5.79 N, 10.06; Found: C, 48.77; H, 5.82; N, 9.99

EXAMPLE 4

3-[(4-Chlorophenyl)sulfinyl]-N-[2-(diethylamino)ethyl]-1-pyrrolidinecarboxamide

A solution of 4.37 g (0.027 mole) of 1,1'-carbonyldiimidazole and 2.96 g (0.0255 mole) of N,N-diethylaminoethylamine in 200 ml of tetrahydrofuran was stirred at room temperature for 45 min. A solution of 4.78 g (0.0209 mole) of 3-[(4-chlorophenyl)sulfinyl]pyrrolidine (free base) in tetrahydrofuran was added and the solution was refluxed for 16 hr. The solvent was removed in vacuo and the resulting oil was dissolved in methylene chloride. The methylene chloride solution was extracted with water and was dried over magnesium sulfate. The solvent was removed in vacuo. The solid residue was recrystallized from a mixture of methylene chloride, ether and hexane to give 3.45 g (44.4%) of white crystals, m.p. 127.5°–130° C.

Analysis: Calculated for $C_{17}H_{26}N_3O_2SCl$: C, 54.90; H, 7.05; N, 11.50; Found: C, 55.00; H, 7.00; N, 11.43

EXAMPLE 5

3-[(4-Chlorophenyl)sulfonyl]-N-[2-(diethylamino)ethyl]-1-pyrrolidinecarboxamide

A solution of 4.93 g (0.0304 mole) of 1,1'-carbonyldiimidazole and 3.36 g (0.029 mole) of N,N-diethylaminoethylamine in 200 ml of tetrahydrofuran was stirred for 40 min at room temperature. A solution of 5.78 g (0.0236 mole) of 3-[(4-chlorophenyl)sulfonyl]pyrrolidine (free base) in tetrahydrofuran was added and the solution was refluxed overnight. The solvent was removed in vacuo and the resulting oil was dissolved in methylene chloride. The solution was extracted with several portions of water and was dried over magnesium sulfate. The solvent was removed in vacuo to give an oil residue. The residue was crystallized from a mixture of methanol, ether and hexane to give 4.28 g (46.7%) of white crystals, m.p. 86°–87.5° C.

Analysis: Calculated for $C_{17}H_{26}N_3O_3SCl$: C, 52.64; H, 6.76; N, 10.83; Found: C, 52.73; H, 6.77; N, 11.07

EXAMPLE 6

3-[(4-Chlorophenyl)sulfonyl]-N-[2-(dimethylamino)ethyl]-1-pyrrolidinecarboxamide A solution of 5.00 g (0.0309 mole) of 1,1'-carbonyldiimidazole and 2.56 g (0.029 mole) of N,N-dimethylaminoethylamine in 200 ml of tetrahydrofuran was stirred at room temperature for about 1 hr. A solution of 5.99 g (0.0244 mole) of 3-[(4-chlorophenyl)sulfonyl]pyrrolidine (free base) in tetrahydrofuran was added and the solution was refluxed for 16 hr. The solvent was removed in vacuo and the resulting oil was dissolved in a mixture of 200 ml of diethyl ether and 20 ml of methylene chloride. The solution was extracted with one 150 ml portion of water. The ether phase was discarded. On standing at room temperature, the aqueous extract yielded a white precipitate. The precipitate was recrystallized from methylene chloride-diethyl ether to give 4.51 g (51.36%) of white crystals, m.p. 131°–132.5° C.

Analysis: Calculated for $C_{15}H_{22}N_3O_3SCl$: C, 50.06; H, 6.16; N, 11.68; Found: C, 50.05; H, 6.17; N, 11.87

EXAMPLE 7

3-(Phenylsulfonyl)-N-[2-(diethylamino)ethyl]-1-pyrrolidinecarboxamide Oxalate [1:1]

A mixture of 3.08 g (0.026 mole) of N,N-diethylaminoethylamine and 4.56 g (0.0281 mole) of 1,1'-carbonyldiimidazole in 400 ml of tetrahydrofuran was stirred at room temperature for 1 hr. A solution of 4.79 g (0.0227 mole) of 3-(phenylsulfonyl)pyrrolidine (free base) in 100 ml of tetrahydrofuran was added and the mixture was refluxed for 16 hr. The solvent was removed in vacuo and the residual oil was partitioned between methylene chloride and water. The methylene chloride phase was dried over magnesium sulfate and the solvent was removed in vacuo to give the free base of the title compound as residue. The free base was converted to the oxalate salt and the salt was recrystallized from methanol-diethyl ether to give 6.04 g (60.1%) of white crystals, m.p. 111°–115° C. with decomposition.

Analysis: Calculated for $C_{19}H_{29}N_3O_7S$: C, 51.45; H, 6.59; N, 9.47; Found: C, 51.23; H, 6.59; N, 9.61

EXAMPLE 8

N-[2-(Diethylamino)ethyl]-3-[(4-methylphenyl)thio]-1-pyrrolidinecarboxamide Oxalate [1:1]

Following the procedure of Example 7, N,N-diethylaminoethylamine and 1,1'-carbonyldiimidazole and 3-[(4-methylphenyl)thio]pyrrolidine were reacted to give the free base of the title compound which was converted to the white crystalline oxalate salt in 48.5% yield, m.p. 82°–86° C.

Analysis Calculated for $C_{20}H_{31}N_3O_5S$: C, 56.45; H, 7.34; N, 9.87; Found: C, 56.08; H, 7.29; N, 9.80

EXAMPLE 9

N-[2-(Diethylamino)ethyl]-3-[(4-methylphenyl)sulfonyl]-1-pyrrolidinecarboxamide Fumarate [2:3]

Following the procedure of Example 7, N,N-diethylaminoethylamine and 1,1'-carbonyldiimidazole and 3-[(4-methylphenyl)sulfonyl]pyrrolidine were reacted to give the free base of the title compound which was converted to the above fumarate salt in 19% yield, m.p. 122°–123° C.

Analysis: Calculated for $C_{24}H_{35}N_3O_9S$: C, 53.22; H, 6.51; N, 7.76; Found: C, 53.23; H, 6.63; N, 7.86

EXAMPLE 10

N-[3-(Diethylamino)propyl]-3-(phenylsulfonyl)-1-pyrrolidinecarboxamide Monohydrate A solution of 4.95 g (0.38 mole) of 3-diethylaminopropylamine and 6.50 g (0.040 mole) of 1,1'-carbonyldiimidazole in 400 ml of tetrahydrofuran was stirred at room temperature for 1 hr. A solution of 7.08 g (0.0336 mole) of 3-(phenylsulfonyl)pyrrolidine (free base) in 100 ml of tetrahydrofuran was added and the mixture was refluxed overnight. The tetrahydrofuran was removed in vacuo and the residue was partitioned between methylene chloride and water. The methylene chloride phase was dried over magnesium sulfate and the solvent was removed in vacuo to give the product as an oil.

Analysis: Calculated for $C_{18}H_{31}N_3O_4S$: C, 56.08; H, 8.11; N, 10.90; Found: C, 55.56; H, 7.98; N, 11.32

EXAMPLE 11

3-[(3,4-Dichlorophenyl)sulfonyl]-N-[2-(dimethylamino)ethyl]-1-pyrrolidinecarboxamide Hemihydrate Following the procedure of Example 7, N,N-dimethylaminoethylamine and 1,1'-carbonyldiimidazole and 3-[3,4-dichlorophenyl)sulfonyl]pyrrolidine was reacted and the solid obtained was recrystallized from a mixture of methylene chloride, diethyl ether and hexane to give the white crystalline hemihydrate in 49.6% yield, m.p. 145°–146° C.

Analysis: Calculated for $C_{30}H_{44}N_6O_7S_2Cl_4$: C, 44.67; H, 5.50; N, 10.42; Found: C, 44.97; H, 5.43; N, 10.46

EXAMPLE 12

3-[(3,4-Dichlorophenyl)sulfonyl]-N-[2-(diethylamino)ethyl]-1-pyrrolidinecarboxamide Hemihydrate Following the procedure of Example 7, N,N-diethylaminoethylamine and 1,1'-carbonyldiimidazole and 3-[3,4-dichlorophenyl)sulfonyl]pyrrolidine were reacted and the oil obtained was crystallized from methylene chloride-diethyl ether to give the white crystalline hemihydrate in 61.6% yield, m.p. 101°–103° C.

Analysis: Calculated for $C_{34}H_{52}N_6O_7S_2Cl_4$: C, 47.33; H, 6.08; N, 9.74; Found: C, 47.48; H, 5.85; N, 9.52

EXAMPLE 13

3-[(3,4-Dichlorophenyl)thio]-N-[2-(diethylamino)ethyl]-1-pyrrolidinecarboxamide Oxalate [1:1] Hemihydrate A solution of 2.43 g (0.015 mole) of 1,1'-carbonyldiimidazole and 1.63 g (0.014 mole) of N,N-diethylaminoethylamine in 400 ml of tetrahydrofuran was stirred at room temperature for 1 hr. A solution of 2.9 g (0.0117 mole) of 3-[3,4-dichlorophenyl)thio]pyrrolidine (free base) in tetrahydrofuran was added and the solution was refluxed for 16 hr. The solvent was removed in vacuo and the residue was dissolved in a mixture of diethyl ether and 30 ml of methylene chloride. The solution was extracted with three portions of water and was dried over magnesium sulfate. The solvent was removed in vacuo to give an oil, the free base of the title compound. The free base was converted to the oxalate salt and was recrystallized from acetonitrile-diethyl ether to give 1.95 g (34.1%) of white crystals, m.p. 77°–80° C., the oxalate hemihydrate.

Analysis: Calculated for $C_{38}H_{56}N_6O_{11}S_2Cl_4$: C, 46.63; H, 5.77 N, 8.59; Found: C, 46.82; H, 5.56; N, 8.32

EXAMPLE 14

3-[(4-Chlorophenyl)sulfonyl]-N-[2-(dimethylamino)ethyl]-1-piperidinecarboxamide Monohydrochloride To a solution of 5.2 g (0.032 mole) of 1,1'-carbonyldiimidazole in 200 ml of tetrahydrofuran was added a solution of 2.73 g (0.031 mole) of N,N-dimethylaminoethylamine in tetrahydrofuran. The solution was stirred at room temperature for 1 hr. A solution of 7.18 g (0.0227 mole) of 3-[(4-chlorophenyl)sulfonyl]piperidine in tetrahydrofuran was added and the solution was refluxed for 5 hr and then stirred at room temperature for 16 hr. The volume of the solution was reduced to about 100 ml in vacuo and this solution was quenched in excess water. The mixture was extracted with methylene chloride. The methylene chloride phase was dried over magnesium sulfate and the volume reduced to about 150 ml in vacuo. Diethyl ether was added and the solution was placed in the freezer overnight. White crystalline solid, 7.55 g (62.9%), the free base of the title compound was collected, m.p. 129°–131° C. The free base was dissolved in methanol and reacted with ethereal hydrogen chloride and the salt precipitated with diethyl ether and recrystallized from methanol diethyl ether to give 7.58 g of white crystalline monohydrochloride, m.p. 218.5°–219° C.

Analysis: Calculated for $C_{16}H_{25}N_3O_3SCl$: C, 46.83; H, 6.14; N, 10.24; Found: C, 46.92; H, 6.16; N, 10.30

EXAMPLE 15

3-[(4-Chlorophenyl)thio]-N-[2-(dimethylamino)ethyl]-1-piperidinecarboxamide Monohydrochloride A solution of 5.70 g (0.0352 mole) of 1,1'-carbonyldiimidazole and 2.91 g (0.033 mole) of N,N-dimethylaminoethylamine in 200 ml of tetrahydrofuran was stirred at room temperature for 1.5 hr. A solution of 7.02 g (0.031 mole) of 3-[(4-chlorophenyl)thio]piperidine in 50 ml of tetrahydrofuran was added and the solution was refluxed for 10 hr. The volume of the reaction solution was reduced to about 50 ml in vacuo. The solution was quenched in water and the aqueous mixture was extracted with methylene chloride. The methylene chloride phase was dried over magnesium sulfate and the solvent was removed in vacuo to give an oil, the free base of the title compound. The free base was converted to the hydrochloride salt and recrystallized as in Example 14 to give 8.48 g (72.3%) of white crystals, m.p. 175°–176.5° C.

Analysis: Calculated for $C_{16}H_{25}N_3OSCl_2$: C, 50.79; H, 6.66; N, 11.11; Found: C, 50.97; H, 6.75; N, 11.11

EXAMPLE 16

3-[(3-Chlorophenyl)sulfonyl]-N-[2-(dimethylamino)ethyl]-1-piperidinecarboxamide Monohydrochloride A solution of 3.57 g (0.022 mole) of 1,1'-carbonyldiimidazole and 1.78 g (0.020 mole) of N,N-dimethylaminoethylamine in 200 ml of tetrahydrofuran was stirred at room temperature for 1 hr. A solution of 4.63 g (0.0179 mole) of 3-[(3-chlorophenyl)sulfonyl]piperidine (free base) in 100 ml of tetrahydrofuran was added and the mixture was refluxed for 22 hr. The solvent was removed in vacuo to give an oil. The oil was dissolved in methylene chloride and the solution was extracted with 6 portions of water, the water washes being discarded. The methylene chloride phase was dried over magnesium sulfate and the solvent was removed in vacuo to give an oil, the free base of the title compound. The free base was converted to the hydrochloride salt as in Example 14 to give 3.39 g (46.2%) of white crystals, m.p. 181°–183° C. with decomposition.

Analysis: Calculated for $C_{16}H_{25}N_3C_3SCl_2$: C, 46.83; H, 6.14; N, 10.24; Found: C, 46.82; H, 6.13; N, 10.36

EXAMPLE 17

3-[(3-Chlorophenyl)thio]-N-[(dimethylamino)ethyl]-1-piperidinecarboxamide Monohydrobromide Following the procedure of Example 16, 1,1'-carbonyldiimidazole and N,N-dimethylaminoethylamine and 3-[(3-chlorophenyl)thio]piperidine were reacted to give the free base of the title compound. The free base was reacted with hydrobromic acid and the salt was recrystallized from acetonitrile-diethyl ether to give crystalline solid in 22.7% yield, m.p. 91°–96° C.

Analysis: Calculated for $C_{16}H_{25}N_3OSClBr$: C, 45.45; H, 5.96; N, 9.94; Found: C, 45.76; H, 6.06; N, 10.05

EXAMPLE 18

3-[(4-Chlorophenyl)sulfinyl]-N-[2-(dimethylamino)ethyl]-1-piperidinecarboxamide Fumarate [2:3]

Following the procedure of Example 16, 1,1'-carbonyldiimidazole and N,N-dimethylaminoethylamine and 3-[(4-chlorophenyl)sulfinyl piperidine (free base) were reacted to give the free base of the title compound, isolated as an oil. The free base was reacted with fumaric acid in methanol and the salt precipitated with ether and was recrystallized from methanol-diethyl ether as white crystals in 18.5% yield, m.p. 146°–149° C. (with decomposition).

Analysis: Calculated for $C_{20}H_{30}N_3O_8SCl$: C, 49.67; H. 5.68; N, 7.90; Found: C, 49.15; H, 5.66; N, 7.90

EXAMPLE 19

3-[(4-Chlorophenyl)sulfonyl]-N-[2-(diethylamino)ethyl]-1-piperidine Carboxamide

Following the procedure of Example 16, 1,1'-carbonyldiimidazole and N,N-diethylaminoethylamine, and 3-[(4-chlorophenyl)sulfonyl]piperidine were reacted to give the title compound which was recrystallized from methylene chloride-diethyl ether as white crystals in 70.5% yield, m.p. 141°–142° C.

Analysis: Calculated for $C_{17}H_{28}N_3O_3SCl$: C, 53.79; H, 7.02; N, 10.45; Found: C, 53.85; H, 7.05; N, 10.54

EXAMPLE 20

N-[2-(Diethylamino)ethyl]-3-(phenylsulfonyl)-1-piperidinecarboxamide Oxalate [1:1]

Following the procedure of Example 16, 1,1'-carbonyldiimidazole and N,N-diethylaminoethylamine and 3-(phenylsulfonyl)piperidine were reacted to give the free base of the title compound as an oil which crystallized from diethyl ether as a white crystalline solid in 58% yield. The free base was reacted with oxalic acid and the oxalate salt was recrystallized from methanol-diethyl ether to give white crystals in 51.0% yield, m.p. 145°–146° C. (with decomposition).

Analysis: Calculated for $C_{20}H_{31}N_3O_7S$: C, 52.50; H, 6.83; N, 9.18; Found: C, 52.55; H, 6.85; N, 9.11

EXAMPLE 21

N-[2-(Dimethylamino)ethyl]-3-(phenylsulfonyl)-1-piperidinecarboxamide, Oxalate [1:1]

Following the procedure of Example 16, 1,1'-carbonyldiimidazole and N,N-dimethylaminoethylamine and 3-(phenylsulfonyl)piperidine were reacted to give the free base of the title compound as an oil. The free base was reacted with oxalic acid and the oxalate salt was recrystallized from methanol-diethyl ether as white crystals in 81.3% yield, m.p. 177°–178° C.

Analysis: Calculated for $C_{18}H_{27}N_3O_7S$: C, 50.34; H, 6.34; N, 9.78; Found: C, 50.06; H, 6.29; N, 9.76

EXAMPLE 22

N-[2-(Diethylamino)ethyl]-3-(phenylsulfonyl)-1-piperidinecarbothioamide Maleate [1:1]

A solution of 2.35 g (0.0104 mole) of 3-(phenylsulfonyl)piperidine (free base), 1.38 g (0.012 mole) of thiophosgene and excess triethylamine in methylene chloride was stirred at room temperature for 1 hr. The solution was extracted with water and the methylene chloride phase was dried over magnesium sulfate and the solvent was removed in vacuo to give a solid residue. The residue was dissolved in tetrahydrofuran, an excess of N,N-diethylaminoethylamine was added and the mixture was refluxed for 12 hr. The solvent was removed in vacuo. The residue was dissolved in methylene chloride and the solution was extracted with water. The methylene chloride phase was dried over magnesium sulfate and the solvent was removed in vacuo to give the free base of the title compound. The free base was reacted with maleic acid in methanol and precipitated with diethyl ether. The maleate salt was recrystallized from the same solvent to give 1.73 g (24.8%) white crystals, m.p. 122°–124° C.

Analysis: Calculated for $C_{22}H_{33}N_3O_6S_2$: C, 52.89; H, 6.66; N, 8.41; Found: C, 52.79; H, 6.71; N, 8.25

EXAMPLE 23

N-[2-(Diethylamino)ethyl]-3-[(4-methylphenyl)sulfonyl]-1-piperidinecarboxamide

Following the procedure of Example 16, 1,1'-carbonyldiimidazole, N,N-diethylaminoethylamine and 3-[(4-methylphenyl)sulfonyl]piperidine were reacted to give the title compound which crystallized from diethyl ether as white crystals in 57.9% yield, m.p. 115.5°–117.5° C.

Analysis: Calculated for $C_{19}H_{31}N_3O_3S$: C, 59.81; H, 8.19; N, 11.01; Found: C, 59.49; H, 8.11; N, 10.93

EXAMPLE 24

N-[2-(Diethylamino)ethyl]-3-[(4-fluorophenyl)sulfonyl]-1-piperidinecarboxamide

Following the procedure of Example 16, 1,1'-carbonyldiimidazole and N,N-diethylaminoethylamine and 3-[(4-fluorophenyl)sulfonyl]piperidine were reacted to give the title compound which was recrystallized from methylene chloride-hexane as white crystals in 58.6% yield, m.p. 137°–138° C.

Analysis: Calculated for $C_{18}H_{28}N_3O_3SF$: C, 56.08; H, 7.32; N, 10.90; Found: C, 55.94; H, 7.32; N, 10.88

EXAMPLE 25

N-[3-(Diethylamino)propyl]-3-(phenylsulfonyl)-1-piperidinecarboxamide

Following the procedure of Example 16, 3-diethylaminopropylamine and 1,1'-carbonyldiimidazole and 3-(phenylsulfonyl)piperidine were reacted to give the title compound which was recrystallized from diethyl ether-hexane as white crystals in 58.5% yield, m.p. 56°–58.5° C.

Analysis: Calculated for $C_{19}H_{31}N_3O_3S$: C, 59.81; H, 8.19; N, 11.01; Found: C, 59.64; H, 8.19; N, 11.04

EXAMPLE 26

N-[2-(Diethylamino)ethyl]-3-[(4-methoxyphenyl)sulfonyl]-1-piperidinecarboxamide

Following the procedure of Example 16, N,N-diethylaminoethylamine and 1,1'-carbonyldiimidazole and 3-[(4-methoxyphenyl)sulfonyl]piperidine were reacted to give the title compound which was crystallized from diethyl etherhexane as white crystals in 69.2% yield, m.p. 118°–121° C.

Analysis: Calculated for $C_{19}H_{31}N_3O_4S$: C, 57.41; H, 7.86; N, 10.57; Found: C, 57.20; H, 7.83; N, 10.63

EXAMPLE 27

N-[2-[bis(1-Methylethyl)amino]ethyl]-3-(phenylsulfonyl)-1-piperidinecarboxamide

Following the procedure of Example 16, diisopropylaminoethylamine and 1,1'-carbonyldiimidazole and 3-(phenylsulfonyl)piperidine were reacted to give the title compound which was crystallized from diethyl ether-hexane as white solid in 59.8% yield, m.p. 82.5°–84° C.

Analysis: Calculated for $C_{20}H_{33}N_3O_3S$: C, 60.73; H, 8.41; N, 10.82; Found: C, 60.71; H, 8.54; N, 10.80

EXAMPLE 28

4-[(4-Chlorophenyl)thio]-N-[2-(dimethylamino)ethyl]-1-piperidinecarboxamide Maleate [1:1]

Following the procedure of Example 16, 1,1'-carbonyldiimidazole and N,N-dimethylaminoethylamine and 4-[(4-chlorophenyl)thio]piperidine were reacted to give the free base of the title compound as white crystals, m.p. 90.5°–91.5° C. The free base was reacted with maleic acid and the maleate salt was recrystallized from methanoldiethyl ether to give white crystals, m.p. 124.5°–126° C.

Analysis: Calculated for $C_{20}H_{28}N_3O_5SCl$: C, 52.45; H, 6.16; N, 9.18; Found: C, 52.43; H, 6.16; N, 9.17

EXAMPLE 29

4-[4-(Chlorophenyl)sulfonyl]-N-[2-(dimethylamino)ethyl]-1-piperidinecarboxamide Fumarate [1:1]

Following the procedure of Example 16, 1,1'-carbonyldiimidazole and N,N-dimethylaminoethylamine and 4-[(4-chlorophenyl)sulfonyl]piperidine were reacted to give the free base of the title compound. The free base was reacted with fumaric acid and the fumarate salt was recrystallized from methanol-diethyl ether to give white crystals in 80.4% yield, m.p. 181°–182° C. (with decomposition).

Analysis: Calculated for $C_{20}H_{28}N_3O_7SCl$: C, 49.03; H, 5.76; N, 8.58; Found: C, 48.97; H, 5.81; N, 8.54

EXAMPLE 30

4-[(4-Chlorophenyl)sulfinyl]-N-[2-(dimethylamino)ethyl]-1-piperidinecarboxamide Fumarate Following the procedure of Example 16, 1,1'-carbonyldiimidazole and N,N-dimethylaminoethylamine and 4-[(4-chlorophenyl)sulfinyl]piperidine were reacted to give the free base of the title compound. The free base was reacted with fumaric acid and the fumarate salt was recrystallized from methanol diethyl ether to give white crystals in 23.7% yield, m.p. 135°–138° C.

Analysis: Calculated for $C_{20}H_{28}N_3O_6SCl$: C, 50.68; H, 5.96; N, 8.87; Found: C, 50.32; H, 5.91; N, 8.86

EXAMPLE 31

N-[2-(Diethylamino)ethyl]-3-[[4-[2-(dimethylamino)ethoxy]phenyl]sulfonyl]-1-piperidinecarboxamide Following the procedure of Example 16, N,N-diethyl aminoethylamine and 1,1'-carbonyldiimidazole and N,N-dimethyl-2-[4-[(3-piperidinyl)sulfonyl]phenoxy]ethanamine were reacted to give the title compound which was crystallized from diethyl ether-hexane as white crystals in 33.1% yield, m.p. 79°–80° C.

Analysis: Calculated for $C_{22}H_{38}N_4O_4S$: C, 58.12; H, 8.43; N, 12.32; Found: C, 58.34; H, 8.52; N, 12.58

EXAMPLE 32

N-[2-(Diethylamino)ethyl]-3-[[4-(2-methoxyethoxy)phenyl]sulfonyl]-1-piperidinecarboxamide Following the procedure of Example 16, N,N-diethylaminoethylamine and 1,1'-carbonyldiimidazole and 3-[[4-(2-methoxyethoxy)phenyl]sulfonyl]piperidine were reacted to give the title compound which was crystallized from methylene chloride-diethyl ether as white crystals in 67.8% yield, m.p. 98°–99° C.

Analysis: Calculated for $C_{21}H_{35}N_3O_5S$: C, 57.12; H, 7.99; N, 9.52; Found: C, 57.13; H, 8.03; N, 9.51

EXAMPLE 33

3-[[4-[2-(Diethylamino)ethoxy]phenyl]sulfonyl]-N-[2-(diethylamino)ethyl]-1-piperidinecarboxamide Following the procedure of Example 16, N,N-diethylaminoethylamine and 1,1'-carbonyldiimidazole and N,N-diethyl-2-[4-[(3-piperidinyl)sulfonyl]phenoxy]ethanamine were reacted to give the title compound which was crystallized from diethyl ether hexane to give 1.77 g (19.6%) of white crystals, m.p. 66°–67.5° C.

Analysis: Calculated for $C_{24}H_{42}N_4O_4S$: C, 59.72; H, 8.77; N, 11.61; Found: C, 59.64; H, 8.83; N, 11.56

EXAMPLE 34

N-[2-(Dimethylamino)ethyl]-3-[(phenylsulfonyl)methyl]-1-piperidinecarboxamide Oxalate [1:1]

Following the procedure of Example 16, N,N-dimethylaminoethylamine and 1,1'-carbonyldiimidazole and 3-[(phenylsulfonyl)methyl]piperidine were reacted to give the free base of the title compound. The free base was reacted with oxalic acid and the salt was recrystallized from methanol-diethyl ether to give 8.47 g (78.7%) of white crystals, m.p. 170.171° C. (with decomposition).

Analysis: Calculated for $C_{19}H_{29}N_3O_7S$: C, 51.45; H, 6.59; N, 9.47; Found: C, 51.22; H, 6.57; N, 9.51

EXAMPLE 35

N-[2-(Diethylamino)ethyl]-3-[(phenylsulfonyl)methyl]-1-piperidinecarboxamide Oxalate [1:1]

Following the procedure of Example 16, N,N-dimethylaminoethylamine and 1,1'-carbonyldiimidazole and 3-[(phenylsulfonyl)methyl]piperidine were reacted to give the free base of the title compound. The free base was reacted with oxalic acid and the salt was recrystallized from methanol-diethyl ether to give 7.07 g (50.4%) of white crystals, m.p. 107°-108.5° C. (with decomposition).

Analysis: Calculated for $C_{21}H_{33}N_3O_7S$: C, 53.49; H, 7.05; N, 8.91; Found: C, 53.17; H, 7.02; N, 9.03

EXAMPLE 36 a-d

When in the procedure of Example 22 phosgene is substituted for thiophosgene and the following are substituted for diethylaminoethylamine:
ethylenediamine,
sym-N,N'-dimethylethylenediamine,
N,N-diethyl-N'-methylethylenediamine, and
N,N-diethyl-N'-isopropylethylenediamine,
there are obtained
(a) 3-(phenylsulfonyl)-N-(2-aminoethyl)-1-piperidinecarboxamide, maleate,
(b) 3-(phenylsulfonyl)-N-methyl-N-[2-(methylamino)ethyl]-1-pyrrolidine carboxamide maleate,
(c) 3-(phenylsulfonyl)-N-(methyl)-N-[2-(diethylamino)ethyl]-1-pyrrolidinecarboxamide maleate, and
(d) 3-(phenylsulfonyl)-N-(1-methylethyl)-N-[2-(diethylamino)ethyl]-1-pyrrolidinecarboxamide maleate.

EXAMPLE 37 a-u

Following the procedure of Example 16 and substituting an equal molar amount of the following for 3-[(3-chlorophenyl)sulfonyl]piperidine:
3-(1-naphthylsulfonyl)piperidine,
3-(2-naphthylsulfonyl)piperdine,
3-(4-indanylsulfonyl)piperidine,
3-(5-indanylsulfonyl)piperidine,
3-(4-biphenylsulfonyl)piperidine,
3-[(4-fluorophenyl)sulfonyl]piperidine,
3-[(4-cyanophenyl)sulfonyl]piperidine,
3-[(4-nitrophenyl)sulfonyl]piperidine,
3-[(4-dimethylaminophenyl)sulfonyl]piperidine,
3-[[4-[(N,N-dimethylamino)carbonyl]phenyl]sulfonyl]piperidine,
N,N-diethyl-2-[4-[(3-piperidinyl)sulfonyl]phenylthio]ethanamine,
N,N-diethyl-2-[4-[(3-piperidinyl)sulfonyl]phenylsulfinyl]ethanamine,
N,N-diethyl-2-[4-[(3-piperidinyl)sulfonyl]phenylsulfonyl]ethanamine,
N,N-diethyl-2-[4-[(3-piperidinyl)sulfonyl]phenylethanamine,
3-[4-(methylthiophenyl)sulfonyl]piperidine,
3-[[4-(methylsulfinyl)phenyl]sulfonyl]piperidine,
3-[[4-(methylsulfonyl)phenyl]sulfonyl]piperidine,
3-[[4-(phenylthio)phenyl]sulfonyl]piperidine,
3-[(4-trifluoromethylphenyl)sulfonyl]piperidine,
3-[(4-bromophenyl)sulfonyl]piperidine, and
3-[(4-iodophenyl)sulfonyl]piperidine,
there are obtained:
(a) N-[2-(diethylamino)ethyl]-3-(1-naphthylsulfonyl)-1-piperidinecarboxamide hydrochloride,
(b) N-[2-(dimethylamino)ethyl]-3-(2-naphthylsulfonyl)-1-piperidinecarboxamide hydrochloride,
(c) N-[2-(dimethylamino)ethyl]-3-[(2,3-dihydro-1H-inden-4-yl)sulfonyl]-1-piperidinecarboxamide hydrochloride,
(d) N-[2-(dimethylamino)ethyl]-3-[2,3-dihydro-1H-inden-5-yl)sulfonyl]-1-piperidinecarboxamide hydrochloride,
(e) 3-(4-biphenyl)sulfonyl-N-[2-(dimethylamino)ethyl]-1-piperidinecarboxamide hydrochloride,
(f) 3-[(4-fluorophenyl)sulfonyl]-N-[2-(dimethylamino)ethyl]-1-piperidinecarboxamide hydrochloride,
(g) 3-[(4-cyanophenyl)sulfonyl]-N-[2-(dimethylamino)ethyl]-1-piperidinecarboxamide hydrochloride,
(h) N-[2-(dimethylamino)ethyl]-3-[(4-nitrophenyl)sulfonyl]-1-piperidinecarboxamide hydrochloride,
(i) N-[2-(dimethylamino)ethyl]-3-[(4-dimethylaminophenyl)sulfonyl]-1-piperidinecarboxamide hydrochloride,
(j) N-[2-(dimethylamino)ethyl]-3-[(4-dimethylaminocarbonylphenyl)sulfonyl]-1-piperidinecarboxamide hydrochloride,
(k) N-[2-(dimethylamino)ethyl]-3-[[4-[2-(diethylamino)ethyl thio]phenyl]sulfonyl]-1-piperidinecarboxamide hydrochloride,
(l) N-[2-(dimethylamino)ethyl]-3-[[4-[2-(diethylamino)ethyl sulfinyl]phenyl]sulfonyl]-1-piperidinecarboxamide hydrochloride,
(m) N-[2-(dimethylamino)ethyl]-3-[[4-[2-(diethylamino)ethyl sulfonyl]phenyl]sulfonyl]-1-piperidinecarboxamide hydrochloride,
(n) N-[2-(diethylamino)ethyl]-3-[[4-[2-(dimethylamino)ethyl]phenyl]sulfonyl]-1-piperidinecarboxamide hydrochloride,
(o) N-[2-(dimethylamino)ethyl]-3-[(4-methylthiophenyl)sulfonyl]-1-piperidinecarboxamide hydrochloride,
(p) N-[2-(dimethylamino)ethyl]-3-[(4-methylsulfinylphenyl)sulfonyl]-1-piperidinecarboxamide hydrochloride,
(q) N-[2-(dimethylamino)ethyl]-3-[(4-methylsulfonylphenyl)sulfonyl]-1-piperidinecarboxamide hydrochloride,
(r) N-[2-(dimethylamino)ethyl]-3-[(4-phenylthiophenyl)sulfonyl]-1-piperidinecarboxamide hydrochloride,
(s) N-[2-(dimethylamino)ethyl]-3-[(4-trifluoromethylphenyl)sulfonyl]-1-piperidinecarboxamide,
(t) 3-[(4-bromophenyl)sulfonyl]-N-[2-(dimethylamino)ethyl]-1-piperidinecarboxamide, and
(u) N-[2-(dimethylamino)ethyl]-3-[(4-iodophenyl)sulfonyl]-1-piperidinecarboxamide.

EXAMPLE 38 a–e

Following the procedure of Example 16 and substituting an equal molar amount of the following for N,N-dimethylaminoethylamine:
2-(1-pyrrolidinyl)ethylamine,
2-(1-piperidinyl)ethylamine,
2-(4-morpholinyl)ethylamine,
2-(4-methylpiperazin-1-yl)ethylamine,
2-(4-phenylpiperazin-1-yl)ethylamine,
there are obtained:
(a) 3-[(3-chlorophenyl)sulfonyl]-N-[2-(1-pyrrolidinyl)ethyl]-1-piperidinecarboxamide hydrochloride,
(b) 3-[(3-chlorophenyl)sulfonyl]-N-[2-(1-piperidinyl)ethyl]-1-piperidinecarboxamide hydrochloride,
(c) 3-[(3-chlorophenyl)sulfonyl]-N-[2-(4-morpholinyl)ethyl]-1-piperidinecarboxamide hydrochloride,
(d) 3-[(3-chlorophenyl)sulfonyl]-N-[2-(4-methylpiperazin-1-yl)ethyl]-1-piperidinecarboxamide hydrochloride,
(e) 3-[(3-chlorophenyl)sulfonyl]-N-[2-(4-phenylpiperazin-1-yl)ethyl]-1-piperidincarboxamide hydrochloride,

EXAMPLE 39 a–d

Following the procedure of Example 16 and substituting an equal molar amount of the following for N,N-dimethylaminoethylamine:
N-methyl,N-phenylethylenediamine,
N-cyclohexyl,N-methylethylenediamine,
N-methyl,N-benzylethylenediamine,
N-methyl,N-phenethylethylenediamine,
there are obtained:
(a) 3-[(3-chlorophenyl)sulfonyl]-N-[2-(N-methyl,N-phenyl)ethyl]-1-piperidinecarboxamide hydrochloride,
(b) 3-[(3-chlorophenyl)sulfonyl]-N-[2-(N-cyclohexyl,N-methyl)ethyl]-1-piperidinecarboxamide hydrochloride,
(c) 3-[(3-chlorophenyl)sulfonyl]-N-[2-[(N-benzyl, N-methyl)amino]ethyl]-1-piperidinecarboxamide hydrochloride,
(d) 3-[(3-chlorophenyl)sulfonyl]-N-[2-[(N-phenethyl, N-methyl)amino]ethyl]-1-piperidinecarboxamide hydrochloride.

EXAMPLE 40 a–o

Following the procedure of Example 16 and substituting equal molar amounts of the following for 3-[(3-chlorophenyl)sulfonyl]piperidine:
3-[(2,3-dimethylphenyl)sulfonyl]piperidine,
3-[(2,4-dimethylphenyl)sulfonyl]piperidine,
3-[(2,3,5-trimethylphenyl)sulfonyl]piperidine,
3-[(2,4,6-trimethylphenyl)sulfonyl]piperidine,
3-[(4-tertiarybutylphenyl)sulfonyl]piperidine,
3-[(2-methyl-4-ethylphenyl)sulfonyl]piperidine,
3-[(2,4-dimethoxyphenyl)sulfonyl]piperidine,
3-[(2,4-diethoxyphenyl)sulfonyl]piperidine,
3-[(3-chloro-4-methoxyphenyl)sulfonyl]piperidine,
3-[(3-chloro-5-methoxyphenyl)sulfonyl]piperidine,
3-[(2,6-dimethoxyphenyl)sulfonyl]piperidine,
3-[(3-chloro-4,5-dimethoxyphenyl)sulfonyl]piperidine,
3-[(4-n-butoxyphenyl)sulfonyl]piperidine,
3-[(2-methyl-4-methoxyphenyl)sulfonyl]piperidine, and
3-[(2-methyl-4-ethoxyphenyl)sulfonyl]piperidine,
there are obtained:
(a) N-[dimethylamino)ethyl]-3-[(2,3-dimethylphenyl)sulfonyl]-1-piperidinecarboxamide hydrochloride,
(b) N-[2-(dimethylamino)ethyl]-3-[2,4-dimethylphenyl)sulfonyl]-1-piperidinecarboxamide hydrochloride,
(c) N-[2-(dimethylamino)ethyl]-3-[2,3,5-trimethylphenyl)sulfonyl]-1-piperidinecarboxamide hydrochloride,
(d) N-[2-(dimethylamino)ethyl]-3-[2,4,6-trimethylphenyl)sulfonyl]-1-piperidinecarboxamide hydrochloride,
(e) N-[2-(dimethylamino)ethyl]-3-[4-tertiarybutylphenyl)sulfonyl]-1-piperidinecarboxamide hydrochloride,
(f) N-[2-(dimethylamino)ethyl]-3-[2-methyl-4-ethylphenyl)sulfonyl]-1-piperidinecarboxamide hydrochloride,
(g) N-[2-(dimethylamino)ethyl]-3-[2,4-dimethoxyphenyl)sulfonyl]-1-piperidinecarboxamide hydrochloride,
(h) N-[2-(dimethylamino)ethyl]-3-[(2,4-diethoxyphenyl)sulfonyl]-1-piperidinecarboxamide hydrochloride,
(i) N-(2-(dimethylamino)ethyl]-3-[(3-chloro-4-methoxyphenyl)sulfonyl]-1-piperidinecarboxamide hydrochloride,
(j) N-[2-(dimethylamino)ethyl]-3-[(3-chloro-5-methoxyphenyl)sulfonyl]-1-piperidinecarboxamide hydrochloride,
(k) N-[2-(dimethylamino)ethyl]-3-[(2,6-dimethoxyphenyl)sulfonyl]-1-piperidinecarboxamide hydrochloride,
(l) N-[2-(dimethylamino)ethyl]-3-[(3-chloro-4,5-dimethoxyphenyl)sulfonyl]-1-piperidinecarboxamide hydrochloride,
(m) N-[2-(dimethylamino)ethyl]-3-[(4-butoxyphenyl)sulfonyl]-1-piperidinecarboxamide hydrochloride,
(n) N-[2-(dimethylamino)ethyl]-3-[(2-methyl-4-methoxyphenyl)sulfonyl]-1-piperidinecarboxamide hydrochloride, and
(o) N-[2-(dimethylamino)ethyl]-3-[(2-methyl-4-ethoxyphenyl)sulfonyl]-1-piperidinecarboxamide hydrochloride.

EXAMPLE 41 a–i

Following the procedure of Example 16 and substituting equal molar amounts of the following for 3-[(3-chlorophenyl)sulfonyl]piperidine:
3-[(2-chloro-6-nitrophenyl)sulfonyl]piperidine,
3-[(2-nitro-3-chlorophenyl)sulfonyl]piperidine,
3-[(3-chloro-4-nitrophenyl)sulfonyl]piperidine,
3-[(2-nitro-4-chlorophenyl)sulfonyl]piperidine,
3-[(3-chloro-5-nitrophenyl)sulfonyl]piperidine,
3-[(3-nitro-4-chlorophenyl)sulfonyl]piperidine,
3-[(2-nitro-5-chlorophenyl)sulfonyl]piperidine,
3-[(3-chloro-4-methylthiophenyl)sulfonyl]piperidine, and
3-[(3-chloro-4-phenylthiophenyl)sulfonyl]piperidine,
there are obtained:
(a) 3-[(2-chloro-6-nitrophenyl)sulfonyl]-N-[2-(dimethylamino)ethyl]-1-piperidinecarboxamide hydrochloride,
(b) N-[2-(dimethylamino)ethyl]-3-[(2-nitro-3-chlorophenyl)sulfonyl]-1-piperidinecarboxamide hydrochloride,
(c) 3-[(3-chloro-4-nitrophenyl)sulfonyl]-N-[2-(dimethylamino)ethyl]-1-piperidinecarboxamide hydrochloride,
(d) N-[2-(dimethylamino)ethyl]-3-[(2-nitro-4-chlorophenyl)sulfonyl]-1-piperidinecarboxamide hydrochloride, (e) 3-[(3-chloro-5-nitrophenyl)sulfonyl]-N-[2-(dimethylamino)ethyl]-1-piperidinecarboxamide hydrochloride,
(f) N-[2-(dimethylamino)ethyl]-3-[(3-nitro-4-chlorophenyl)sulfonyl]-1-piperidinecarboxamide hydrochloride,
(g) N-[2-(dimethylamino)ethyl]-3-[(2-nitro-5-chlorophenyl)sulfonyl]-1-piperidinecarboxamide hydrochloride,
(h) 3-[(3-chloro-4-methylthiophenyl)sulfonyl]-N-[2-(dimethylamino)ethyl]-1-piperidinecarboxamide hydrochloride, and
(i) 3-[(3-chloro-4-phenylthiophenyl)sulfonyl]-N-[2-(dimethylamino)ethyl]-1-piperidinecarboxamide hydrochloride.

EXAMPLE 42 a–d

Following the procedure of Example 16, the reaction product of 1,1'-carbonyldiimidazole and N,N-dimethylaminoethylamine is reacted with each of the following:
3-[[(3-chlorophenyl)sulfonyl]methyl]piperidine,
3-[(1-naphthylsulfonyl)methyl]piperidine,
3-[[(2,3-dihydro-1H-inden-4-yl)sulfonyl]methyl]piperidine,
3-[2-[(3-chlorophenyl)sulfonyl]ethyl]piperidine.
to give the following as hydrochloride salts:
(a) 3-[[(3-chlorophenyl)sulfonyl]methyl]-N-[2-(dimethylamino)ethyl]-1-piperidinecarboxamide hydrochloride,
(b) N-[2-(dimethylamino)ethyl]-3-[(1-naphthylsulfonyl)methyl]-1-piperidinecarboxamide hydrochloride,
(c) 3-[[(2,3-dihydro-1H-inden-4-yl)sulfonyl]methyl]-N-[2-(dimethylamino)ethyl-1-piperidinecarboxamide hydrochloride, and
(d) 3-[2-[(3-chlorophenyl)sulfonyl]ethyl]-N-[2-(dimethylamino)ethyl]-1-piperidinecarboxamide hydrochloride.

EXAMPLE 43 a–c

Following the procedure of Example 16, the reaction product of 1,1'-carbonyldiimidazole and dimethylaminoethylamine is reacted with each of the following:
3-[[(4-chlorophenylmethyl)sulfonyl]methyl]piperidine,
3-[[(1-naphthylmethyl)sulfonyl]methyl]piperidine,
3-[[4-biphenylmethyl)sulfonyl]methyl]piperidine,
(a) N-[2-(dimethylamino)ethyl]-3-[[(4-chlorophenylmethyl)sulfonyl]methyl]-1-piperidinecarboxamide hydrochloride,
(b) N-[2-(dimethylamino)ethyl]-3-[[(1-naphthylmethyl)sulfonyl]methyl]-1-piperidinecarboxamide hydrochloride,
(c) N-[2-(dimethylamino)ethyl]-3-[[(4-biphenylmethyl)sulfonyl]methyl]-1-piperidinecarboxamide hydrochloride.

EXAMPLE 44

2-[[(4-Chlorophenyl)sulfonyl]methyl]-N-[2-(dimethylamino)ethyl]-1-piperidinecarboxamide Following the procedure of Example 16, but substituting 2-[[(4-chlorophenyl)sulfonyl]methyl]piperidine (free base of Intermediate 33) for 3-[(3-chlorophenyl)sulfonyl]piperidine, the title compound is prepared.

EXAMPLE 45 a–c

Following the procedure of Example 16, the reaction product of 1,1'-carbonyldiimidazole and N,N-dimethylaminoethylamine is reacted with each of the following:
3-[[(3-chlorophenyl)methyl]sulfonyl]piperidine,
3-[[(1-naphthyl)methyl]sulfonyl]piperidine,
3-[[(2,3-dihydro-1H-inden-4-yl)methyl]sulfonyl]piperidine,
to give the following:
(a) 3-[[(3-chlorophenyl)methyl]sulfonyl]-N-[2-(dimethylamino)ethyl]-1-piperidinecarboxamide hydrochloride,
(b) N-[2-(dimethylamino)ethyl]-3-[[(1-naphthyl)methyl]sulfonyl]-1-piperidinecarboxamide hydrochloride, and
(c) N-[2-(dimethylamino)ethyl]-3-[[(2,3-dihydro-1H-inden-4-yl)methyl]sulfonyl]piperidine hydrochloride,

EXAMPLE 46 a–e

Following the procedure of Example 16, 1,1'-thiocarbonyldiimidazole and N,N-dimethylaminoethylamine are reacted followed by separate reaction of that product with each of the following:
3-[(3-chlorophenyl)sulfonyl]piperidine,
3-(phenylsulfonyl)pyrrolidine,
3-[(4-methylphenyl)sulfonyl]pyrrolidine,
3-(phenylsulfonyl)piperidine, and
3-[(4-methylphenyl)sulfonyl]piperidine,
there are obtained:
(a) 3-[(3-chlorophenyl)sulfonyl]-N-[2-(dimethylamino)ethyl]-1-piperidinecarbothiamide hydrochloride,
(b) N-[2-(dimethylamino)ethyl]-3-(phenylsulfonyl)-1-pyrrolidinecarbothiamide hydrochloride,
(c) N-[2-(dimethylamino)ethyl]-3-[(4-methylphenyl)sulfonyl]-1-pyrrolidinecarbothiamide hydrochloride,
(d) N-[2-(dimethylamino)ethyl]-3-(phenylsulfonyl)-1-piperidinecarbothiamide hydrochloride, and
(e) N-[2-(dimethylamino)ethyl]-3-[(4-methylphenyl)sulfonyl]-1-piperidinecarbothiamide hydrochloride.

EXAMPLE 47

N-[2-(Diethylamino)ethyl]-4-[(4-methoxyphenyl)sulfonyl]-1-piperidinecarboxamide

Following the procedure of Example 16, N,N-diethylaminoethylamine and 1,1'-carbonyldiimidazole and 4-[(4-methoxyphenyl)sulfonyl]piperidine are reacted to give the title compound.

EXAMPLE 48

4-[(2,5-Dichlorophenyl)thio]-N-[2-(diethylamino)ethyl]-1-piperidinecarboxamide

Following the procedure of Example 16, N,N-diethylaminoethylamine and 1,1'-carbonyldiimidazole and 4-[(2,5-dichlorophenyl)thio]piperidine are reacted to give the title compound.

EXAMPLE 49

N-[2-(Diethylamino)ethyl]-4-[(4-methylphenyl)thio]-1-piperidinecarboxamide

Following the procedure of Example 16, N,N-diethylaminoethylamine and 1,1'-carbonyldiimidazole and 4-[(4-methylphenyl)thio]piperidine are reacted to give the title compound.

EXAMPLE 50

N-[2-(Diethylamino)ethyl]-4-(phenylthio)-1-piperidinecarboxamide

Following the procedure of Example 16, N,N-diethylaminoethylamine and 1,1'-carbonyldiimidazole and 4-(phenylthio)piperidine are reacted to give the title compound.

EXAMPLE 51

4-[(2-Chlorophenyl)thio]-N-[2-(diethylamino)ethyl]-1-piperidinecarboxamide

Following the procedure of Example 16, N,N-diethylaminoethylamine and 1,1'-carbonyldiimidazole and 4-[(2-chlorophenyl)thio]piperidine are reacted to give the title compound.

EXAMPLE 52

4-[(3-Chlorophenyl)thio]-N-[1-(diethylamino)ethyl]-1-piperidinecarboxamide

Following the procedure of Example 16, N,N-diethylaminoethylamine and 1,1'-carbonyldiimidazole and 4-[(3-chlorophenyl)thio]piperidine were reacted to give the title compound.

EXAMPLE 53

4-[(3-4-Dichlorophenyl)thio]-N-[2-(diethylamino)ethyl]-1-piperidinecarboxamide

Following the procedure of Example 16, N,N-diethylaminoethylamine and 1,1'-carbonyldiimidazole and 4-[(3,4-dichlorophenyl)thio]piperidine are reacted to give the title compound.

EXAMPLE 54

3-[(2-Chlorophenyl)thio]-N-[2-(diethylamino)ethyl]-1-piperidinecarboxamide

Following the procedure of Example 16, N,N-diethylaminoethylamine and 1,1'-carbonyldiimidazole and 3-[(2 chlorophenyl)thio]piperidine were reacted to give the title compound.

EXAMPLE 55

4-[(4-Fluorophenyl)thio]-N-[2-(diethylamino)ethyl]-1-piperidinecarboxamide

Following the procedure of Example 16, N,N-diethylaminoethylamine and 1,1'-carbonyldiimidazole and 4-[(4-fluorophenyl)thio]piperidine are reacted to give the title compound.

EXAMPLE 56

2-[[(4-Chlorophenyl)thio]methyl]-N-[2-(diethylamino)ethyl]-1-piperidinecarboxamide Following the procedure of Example 16, N,N-diethylaminoethylamine and 1,1'-carbonyldiimidazole and 2-[[(4-chlorophenyl)thio]methyl]piperidine are reacted to give the title compound.

EXAMPLE 57

N-[2-(Diethylamino)ethyl]-4-(phenylsulfinyl)-1-piperidinecarboxamide

Following the procedure of Example 16, N,N-diethylaminoethylamine and 1,1'-carbonyldiimidazole and 4-(phenylsulfinyl)piperidine are reacted to give the title compound.

EXAMPLE 58

N-[2-(Diethylamino)ethyl]-3-[(phenylthio)methyl]-1-piperidinecarboxamide

Following the procedure of Example 16, N,N-diethylaminoethylamine and 1,1'-carbonyldiimidazole and 3-[(phenylthio)methyl]piperidine are reacted to give the title compound.

EXAMPLE 59

N-[2-(Diethylamino)ethyl]-4-[(phenylmethyl)thio]-1-piperidinecarboxamide

Following the procedure of Example 16, N,N-diethylaminoethylamine and 1,1'-carbonyldiimidazole and 4-[(phenylmethyl)thio]piperidine are reacted to give the title compound.

EXAMPLE 60

N-[2-(Diethylamino)ethyl]-4-[(1-phenylmethyl)sulfonyl]-1-piperidinecarboxamide

Following the procedure of Example 16, N,N-diethylaminoethylamine and 1,1'-carbonyldiimidazole and 4-[(phenylmethyl)sulfonyl]piperidine are reacted to give the title compound.

EXAMPLE 61

N-[2-(Diethylamino)ethyl]-3-(phenylthio)-1-piperidinecarboxamide

Following the procedure of Example 16, N,N-diethylaminoethylamine and 1,1'-carbonyldiimidazole and 3-(phenylthio)piperidine are reacted to give the title compound.

EXAMPLE 62 a–d

Following the procedure of Example 16 and substituting the following for 3-[(3-chlorophenyl)sulfonyl]piperidine:
3-[(3,4-dimethoxyphenyl)thio]piperidine,
3-[(3,4-dimethoxyphenyl)sulfonyl]piperidine,
3-[(3,5-dimethoxyphenyl)sulfonyl]piperidine, and
3-[(3,4,5-trimethoxyphenyl)sulfonyl]piperidine,
there are obtained:
(a) N-[2-(dimethylamino)ethyl]-3-[(3,4-dimethoxyphenyl)thio]-1-piperidinecarboxamide,
(b) N-[2-(dimethylamino)ethyl]-3-[(3,4-dimethoxyphenyl)sulfonyl]-1-piperidinecarboxamide,
(c) N-[2-(dimethylamino)ethyl]-3-[(3,5-dimethoxyphenyl)sulfonyl]piperidine, and
(d) N-[2-(dimethylamino)ethyl]-3-[(3,4,5-trimethoxyphenyl)sulfonyl]piperidine.

EXAMPLE 63 a–e

Following the procedure of Example 16 and substituting an equal molar amount of the following for N,N-dimethylaminoethylamine:
1-(2-aminoethyl)-2,6-dimethyl-piperidine,
1-(2-aminoethyl)-4-hydroxy-4-phenyl-piperidine,
1-(2-aminoethyl)-4-cyano-4-phenyl-piperidine,
1-(2-aminoethyl)-4-phenyl-1,2,3,6-tetrahydropyridino and,
1-(2-aminoethyl)-4-phenylmethyl)piperidine,
there are obtained:
(a) 3-[(3-chlorophenyl)sulfonyl]-N-[2-(2,6-dimethyl-piperidine-1-yl)ethyl]-1-piperidinecarboxamide,
(b) 3-[(3-chlorophenyl)sulfonyl]-N-[2-(4-hydroxy-4-phenyl-piperidine-1-yl)ethyl]piperidinecarboxamide.

(c) 3-[(3-chlorophenyl)sulfonyl]-N-[2-(4-cyano-4-phenyl-piperidine-1-yl)ethyl]piperidinecarboxamide,
(d) 3-[(3-chlorophenyl)sulfonyl]-N-[2-(4-phenyl-1,2,3,6-tetrahydropyridin-1-yl)ethyl]piperidinecarboxamide, and
(e) 3-[(3-chlorophenyl)sulfonyl]-N-[2-(4-phenylmethyl-piperidine-1-yl)ethyl]piperidinecarboxamide.

EXAMPLE 64

3-[[4-(Aminocarbonyl)-phenyl]sulfonyl]-N-[2-(diethylamino)ethyl]-1-piperidinecarboxamide Following the procedure of Example 16, N,N-diethylaminoethylamine and 1,1'-carbonyldiimidazol and 3-[[(4-aminocarbonyl)-phenyl]sulfonyl]-piperidine are reacted to give the title compound.

EXAMPLE 65

N-[2-(Diethylamino)ethyl]-3-[[4-(dimethylaminocarbonyl)phenyl]sulfonyl]-1-piperidinecarboxamide Following the procedure of Example 16, N,N-diethylaminoethylamine and 1,1'-carbonyldiimidazole and 3-[[(4-dimethylaminocarbonyl)-phenyl]sulfonyl]piperidine are reacted to give the title compound.

EXAMPLE 66

N-[2-(Ethylamino)ethyl]-3-(phenylsulfonyl)-1-piperidinecarboxamide

The title compound is prepared by reacting 3-(phenylsulfonyl)piperidine with phosgene and reacting the resulting 3-(phenylsulfonyl)piperidine-1-carbonylchloride with N-ethylethylenediamine.

EXAMPLE 67

N-[2-(Ethylamino)ethyl]-3-(phenylsulfonyl)-1-pyrrolidinecarboxamide

The title compound is prepared by reacting 3-(phenylsulfonyl)piperidine with phosgene and reacting the resulting 3-(phenylsulfonyl)pyrrolidine with N-ethylethylenediamine.

EXAMPLE 68

N-[2-(Diethylamino)ethyl]-4-(phenylthio)-1-homopiperidinecarboxamide Oxalate

Following the procedure of Example 16, 1,1'-carbonyldiimidazole, N,N-diethylaminoethylamine and 4-(phenylthio)homopiperidine and oxalic acid are reacted to give the title compound.

EXAMPLE 69

N-[2-(Diethylamino)ethyl]-3-(phenylthio)-1-homopiperidinecarboxamide Oxalate

Following the procedure of Example 16, 1,1'-carbonyldiimidazole, N,N-diethylaminoethylamine and 3-(phenylthio)homopiperidine and oxalic acid are reacted to give the title compound.

EXAMPLE 70

N-[2-(Diethylamino)ethyl]-4-(phenylsulfonyl)-1-homopiperidinecarboxamide Fumarate Following the procedure of Example 16, 1,1'-carbonyldiimidazole and N,N-diethylaminoethylamine and 4-(phenylsulfonyl)homopiperidine are reacted to give the free base of the title compound. The free base is then reacted with fumaric acid and the fumarate salt is recrystallized from methanol-diethyl ether.

EXAMPLE 71

The following are prepared by oxidizing compounds of Examples 68 and 69 with sodium perborate at room temperature:
(a) N-[2-(diethylamino)ethyl]-4-phenylsulfinyl)-1-homopiperidinecarboxamide, and
(b) N-[2-(diethylamino)ethyl]-3-phenylsulfinyl)-1-homopiperidinecarboxamide.

EXAMPLE 72

N-[2-(Diethylamino)ethyl]-3-phenylsulfonyl)-1-homopiperidinecarboxamide fumarate The title compound is prepared as in Example 70 by substituting 3-(phenylsulfonyl)homopiperidine for 4-(phenylsulfonyl)homopiperidine.

TABLE 2

$$-(A^1)_p-X-(A^2)_d-Q$$

Structure: piperidine/pyrrolidine ring with $(CH_2)_n$ and substituent $-(A^1)_p-X-(A^2)_d-Q$, with $Y=C-N-A-NR^1R^2$ attached to ring N, where R is on the N.

| Ex. No. | n | Position of $-(A^1)_p-X-(A^2)_d-Q$ | $(A^1)_p$ | X | $(A^2)_d$ | Q | Y | R | A | $-NR^1R^2$ | Salt |
|---|---|---|---|---|---|---|---|---|---|---|---|
| 1 | 0 | 3-pyrrolidinyl | — | —S— | — | 4-Cl—C$_6$H$_4$— | O | H | —(CH$_2$)$_2$— | —N(C$_2$H$_5$)$_2$ | citrate |
| 2 | 0 | " | — | —S— | — | 4-Cl—C$_6$H$_4$— | O | H | —(CH$_2$)$_2$— | —N(CH$_3$)$_2$ | — |
| 3 | 0 | " | — | —S— | — | 4-Cl—C$_6$H$_4$— | O | H | —(CH$_2$)$_2$— | —N(CH$_3$)$_2$ | oxalate |
| 4 | 0 | " | — | —S(O)— | — | 4-Cl—C$_6$H$_4$— | O | H | —(CH$_2$)$_2$— | —N(C$_2$H$_5$)$_2$ | — |
| 5 | 0 | " | — | —S(O)$_2$— | — | 4-Cl—C$_6$H$_4$— | O | H | —(CH$_2$)$_2$— | —N(CH$_3$)$_2$ | — |
| 6 | 0 | " | — | —S(O)$_2$— | — | 4-Cl—C$_6$H$_4$— | O | H | —(CH$_2$)$_2$— | —N(C$_2$H$_5$)$_2$ | oxalate |
| 7 | 0 | " | — | —S— | — | C$_6$H$_5$ | O | H | —(CH$_2$)$_2$— | —N(CH$_3$)$_2$ | oxalate |
| 8 | 0 | " | — | —S(O)$_2$— | — | 4-CH$_3$—C$_6$H$_4$— | O | H | —(CH$_2$)$_2$— | —N(C$_2$H$_5$)$_2$ | 1.5 fumarate monohydrate |
| 9 | 0 | " | — | —S(O)$_2$— | — | 4-CH$_3$—C$_6$H$_4$— | O | H | —(CH$_2$)$_2$— | —N(CH$_2$H$_5$)$_2$ | hemihydrate |
| 10 | 0 | " | — | —S(O)$_2$— | — | C$_6$H$_5$ | O | H | —(CH$_2$)$_3$— | —N(C$_2$H$_5$)$_2$ | hemihydrate |
| 11 | 0 | " | — | —S(O)$_2$— | — | 3,4-Cl$_2$—C$_6$H$_3$— | O | H | —(CH$_2$)$_2$— | —N(CH$_3$)$_2$ | oxalate.½ H$_2$O |
| 12 | 0 | " | — | —S(O)$_2$— | — | 3,4-Cl$_2$—C$_6$H$_3$— | O | H | —(CH$_2$)$_2$— | —N(C$_2$H$_5$)$_2$ | HCl |
| 13 | 0 | " | — | —S— | — | 4-Cl—C$_6$H$_4$— | O | H | —(CH$_2$)$_2$— | —N(CH$_3$)$_2$ | HCl |
| 14 | 1 | 3-piperidinyl | — | —S— | — | 4-Cl—C$_6$H$_4$— | O | H | —(CH$_2$)$_2$— | —N(C$_2$H$_5$)$_2$ | HCl |
| 15 | 1 | " | — | —S— | — | 3-Cl—C$_6$H$_4$— | O | H | —(CH$_2$)$_2$— | —N(CH$_3$)$_2$ | HBr |
| 16 | 1 | " | — | —S(O)$_2$— | — | 3-Cl—C$_6$H$_4$— | O | H | —(CH$_2$)$_2$— | —N(C$_2$H$_5$)$_2$ | 1.5 fumarate |
| 17 | 1 | " | — | —S— | — | 4-Cl—C$_6$H$_4$— | O | H | —(CH$_2$)$_2$— | —N(CH$_3$)$_2$ | oxalate |
| 18 | 1 | " | — | —S(O)— | — | 4-Cl—C$_6$H$_4$ | O | H | —(CH$_2$)$_2$— | —N(C$_2$H$_5$)$_2$ | oxalate |
| 19 | 1 | " | — | —S(O)$_2$— | — | C$_6$H$_5$ | O | H | —(CH$_2$)$_2$— | —N(CH$_3$)$_2$ | maleate |
| 20 | 1 | " | — | —S— | — | C$_6$H$_5$ | O | H | —(CH$_2$)$_2$— | —N(C$_2$H$_5$)$_2$ | — |
| 21 | 1 | " | — | —S(O)— | — | C$_6$H$_5$ | O | H | —(CH$_2$)$_2$— | —N(CH$_3$)$_2$ | — |
| 22 | 1 | " | — | —S(O)$_2$— | — | 4-CH$_3$—C$_6$H$_4$— | O | H | —(CH$_2$)$_2$— | —N(C$_2$H$_5$)$_2$ | — |
| 23 | 1 | " | — | —S(O)$_2$— | — | 4-F—C$_6$H$_4$— | O | H | —(CH$_2$)$_2$— | —N(CH$_3$)$_2$ | — |
| 24 | 1 | " | — | —S(O)$_2$— | — | C$_6$H$_5$ | S | H | —(CH$_2$)$_2$— | —N(C$_2$H$_5$)$_2$ | — |
| 25 | 1 | " | — | —S(O)$_2$— | — | 4-OCH$_3$—C$_6$H$_4$— | O | H | —(CH$_2$)$_2$— | —N(CH$_3$)$_2$ | — |
| 26 | 1 | " | — | —S(O)$_2$— | — | C$_6$H$_5$ | O | H | —(CH$_2$)$_3$— | —N(C$_2$H$_5$)$_2$ | — |
| 27 | 1 | " | — | —S(O)$_2$— | — | 4-Cl—C$_6$H$_4$— | O | H | —(CH$_2$)$_2$— | —N[—CH(CH$_3$)$_2$]$_2$ | — |
| 28 | 1 | 4-piperidinyl | — | —S— | — | 4-Cl—C$_6$H$_4$— | O | H | —(CH$_2$)$_2$— | —N(CH$_3$)$_2$ | maleate |
| 29 | 1 | " | — | —S(O)— | — | 4-Cl—C$_6$H$_4$— | O | H | —(CH$_2$)$_2$— | —N(CH$_3$)$_2$ | fumarate |
| 30 | 1 | 3-piperidinyl | — | —S(O)$_2$— | — | 4-Cl—C$_6$H$_4$— | O | H | —(CH$_2$)$_2$— | —N(C$_2$H$_5$)$_2$ | fumarate |
| 31 | 1 | " | — | —S(O)$_2$— | — | 4-[O(CH$_2$)$_2$N(CH$_3$)$_2$]—C$_6$H$_4$— | O | H | —(CH$_2$)$_2$— | —N(CH$_3$)$_2$ | — |
| 32 | 1 | " | — | —S(O)$_2$— | — | 4-[O(CH$_2$)$_2$OCH$_3$]—C$_6$H$_4$— | O | H | —(CH$_2$)$_2$— | —N(C$_2$H$_5$)$_2$ | — |
| 33 | 1 | " | — | —S(O)$_2$— | — | 4-[O(CH$_2$)$_2$N(C$_2$H$_5$)$_2$]—C$_6$H$_4$— | O | H | —(CH$_2$)$_2$— | —N(CH$_3$)$_2$ | — |
| 34 | 1 | " | —CH$_2$— | —S(O)$_2$— | — | C$_6$H$_5$ | O | H | —(CH$_2$)$_2$— | —N(CH$_3$)$_2$ | oxalate |
| 35 | 1 | " | —CH$_2$— | —S(O)— | — | C$_6$H$_5$ | O | H | —(CH$_2$)$_2$— | —N(C$_2$H$_5$)$_2$ | oxalate |
| 36a | 1 | " | — | —S(O)$_2$— | — | C$_6$H$_5$ | O | —CH$_3$ | —(CH$_2$)$_2$— | —N(CH$_3$)$_2$ | maleate |
| b | 1 | " | — | —S(O)— | — | C$_6$H$_5$ | O | —CH$_3$ | —(CH$_2$)$_2$— | —NH$_2$ | maleate |
| c | 1 | " | — | —S(O)$_2$— | — | C$_6$H$_5$ | O | —CH(CH$_3$)$_2$ | —(CH$_2$)$_2$— | —NHCH$_3$ | maleate |
| d | 1 | " | — | —S(O)$_2$— | — | C$_6$H$_5$ | O | H | —(CH$_2$)$_2$— | —N(C$_2$H$_5$)$_2$ | maleate |
| 37a | 1 | " | — | —S(O)$_2$— | — | 1-naphthyl | O | H | —(CH$_2$)$_2$— | —N(CH$_3$)$_2$ | HCl |

TABLE 2-continued $$Y=C-N-A-NR^1R^2$$ with structure having $(CH_2)_n$ and $(A^1)_p-X-(A^2)_d-Q$ on piperidine ring, R on N-C.

| Ex. No. | n | Position of $-(A^1)_p-X-(A^2)_d-Q$ | $(A^1)_p$ | X | $(A^2)_d$ | Q | Y | R | A | $-NR^1R^2$ | Salt |
|---|---|---|---|---|---|---|---|---|---|---|---|
| b | 1 | " | — | $-S(O)_2-$ | — | 2-naphthyl | O | H | $-(CH_2)_2-$ | $-N(CH_3)_2$ | HCl |
| c | 1 | " | — | $-S(O)_2-$ | — | 2,3-dihydro-1H—inden-4-yl | O | H | $-(CH_2)_2-$ | $-N(CH_3)_2$ | HCl |
| d | 1 | " | — | $-S(O)_2-$ | — | 2,3-dihydro-1H—inden-5-yl | O | H | $-(CH_2)_2-$ | $-N(CH_3)_2$ | HCl |
| e | 1 | " | — | $-S(O)_2-$ | — | 4-biphenyl | O | H | $-(CH_2)_2-$ | $-N(CH_3)_2$ | HCl |
| f | 1 | " | — | $-S(O)_2-$ | — | $4\text{-F}-C_6H_4-$ | O | H | $-(CH_2)_2-$ | $-N(CH_3)_2$ | HCl |
| g | 1 | " | — | $-S(O)_2-$ | — | $4\text{-CN}-C_6H_4-$ | O | H | $-(CH_2)_2-$ | $-N(CH_3)_2$ | HCl |
| h | 1 | " | — | $-S(O)_2-$ | — | $4\text{-NO}_2-C_6H_4-$ | O | H | $-(CH_2)_2-$ | $-N(CH_3)_2$ | HCl |
| i | 1 | " | — | $-S(O)_2-$ | — | $4-[N(CH_3)_2]-C_6H_4-$ | O | H | $-(CH_2)_2-$ | $-N(CH_3)_2$ | HCl |
| j | 1 | " | — | $-S(O)_2-$ | — | $4-[-C(O)N(CH_3)_2]C_6H_4-$ | O | H | $-(CH_2)_2-$ | $-N(CH_3)_2$ | HCl |
| k | 1 | " | — | $-S(O)_2-$ | — | $4-[S(CH_2)_2N(C_2H_5)_2]-C_6H_4-$ | O | H | $-(CH_2)_2-$ | $-N(CH_3)_2$ | HCl |
| l | 1 | " | — | $-S(O)_2-$ | — | $4-[S(O)-(CH_2)_2N(C_2H_5)_2]C_6H_4-$ | O | H | $-(CH_2)_2-$ | $-N(CH_3)_2$ | HCl |
| m | 1 | 3 piperidinyl | — | $-S(O)_2-$ | — | $4-[S(O)_2-(CH_2)_2N(C_2H_5)_2]C_6H_4-$ | O | H | $-(CH_2)_2-$ | $-N(CH_3)_2$ | HCl |
| n | 1 | " | — | $-S(O)_2-$ | — | $4-[(CH_2)_2N(C_2H_5)_2]-C_6H_4-$ | O | H | $-(CH_2)_2-$ | $-N(CH_3)_2$ | HCl |
| o | 1 | " | — | $-S(O)_2-$ | — | $4-(SCH_3)-C_6H_4-$ | O | H | $-(CH_2)_2-$ | $-N(CH_3)_2$ | HCl |
| p | 1 | " | — | $-S(O)_2-$ | — | $4-[-S(O)CH_3]-C_6H_4-$ | O | H | $-(CH_2)_2-$ | $-N(CH_3)_2$ | HCl |
| q | 1 | " | — | $-S(O)_2-$ | — | $4-[-S(O)_2-CH_3]-C_6H_4$ | O | H | $-(CH_2)_2-$ | $-N(CH_3)_2$ | HCl |
| r | 1 | " | — | $-S(O)_2-$ | — | $4-[SC_6H_5]-C_6H_4$ | O | H | $-(CH_2)_2-$ | $-N(CH_3)_2$ | HCl |
| s | 1 | " | — | $-S(O)_2-$ | — | $4\text{-CF}_3-C_6H_4-$ | O | H | $-(CH_2)_2-$ | $-N(CH_3)_2$ | HCl |
| t | 1 | " | — | $-S(O)_2-$ | — | $4\text{-Br}-C_6H_4-$ | O | H | $-(CH_2)_2-$ | $-N(CH_3)_2$ | HCl |
| u | 1 | " | — | $-S(O)_2-$ | — | $4\text{-I}-C_6H_4-$ | O | H | $-(CH_2)_2-$ | $-N(CH_3)_2$ | HCl |
| 38a | 1 | " | — | $-S(O)_2-$ | — | $3\text{-Cl}-C_6H_4-$ | O | H | $-(CH_2)_2-$ | $-N(CH_3)_2$ | HCl |
| b | 1 | " | — | $-S(O)_2-$ | — | $3\text{-Cl}-C_6H_4-$ | O | H | $-(CH_2)_2-$ | 1-pyrrolidinyl | HCl |
| c | 1 | " | — | $-S(O)_2-$ | — | $3\text{-Cl}-C_6H_4-$ | O | H | $-(CH_2)_2-$ | 1-piperidinyl | HCl |
| d | 1 | " | — | $-S(O)_2-$ | — | $3\text{-Cl}-C_6H_4-$ | O | H | $-(CH_2)_2-$ | 4-morpholinyl | HCl |
| e | 1 | " | — | $-S(O)_2-$ | — | $3\text{-Cl}-C_6H_4-$ | O | H | $-(CH_2)_2-$ | $4\text{-CH}_3$—piperazin-1-yl | HCl |
| 39a | 1 | " | — | $-S(O)_2-$ | — | $3\text{-Cl}-C_6H_4-$ | O | H | $-(CH_2)_2-$ | $4\text{-C}_6H_5$—piperazin-1-yl | HCl |
| b | 1 | " | — | $-S(O)_2-$ | — | $3\text{-Cl}-C_6H_4-$ | O | H | $-(CH_2)_2-$ | $-N(C_6H_5)(CH_3)$ | HCl |
| c | 1 | " | — | $-S(O)_2-$ | — | $3\text{-Cl}-C_6H_4-$ | O | H | $-(CH_2)_2-$ | $-N(C_6H_{11})(CH_3)$ | HCl |
| d | 1 | " | — | $-S(O)_2-$ | — | $3\text{-Cl}-C_6H_4-$ | O | H | $-(CH_2)_2-$ | $-N(-CH_2C_6H_5)(CH_3)$ | HCl |
| 40a | 1 | " | — | $-S(O)_2-$ | — | $2,3(CH_3)_2-C_6H_3-$ | O | H | $-(CH_2)_2-$ | $-N(-CH_2CH_2C_6H_5)(CH_3)$ | HCl |
| b | 1 | " | — | $-S(O)_2-$ | — | $2,4(CH_3)_2-C_6H_3-$ | O | H | $-(CH_2)_2-$ | $-N(CH_3)_2$ | HCl |
| c | 1 | " | — | $-S(O)_2-$ | — | $2,3,5(CH_3)_3-C_6H_2-$ | O | H | $-(CH_2)_2-$ | $-N(CH_3)_2$ | HCl |
| d | 1 | " | — | $-S(O)_2-$ | — | $2,4,6(CH_3)_3-C_6H_2-$ | O | H | $-(CH_2)_2-$ | $-N(CH_3)_2$ | HCl |
| e | 1 | " | — | $-S(O)_2-$ | — | $4\text{-t-butyl-}C_6H_4-$ | O | H | $-(CH_2)_2-$ | $-N(CH_3)_2$ | HCl |
| f | 1 | " | — | $-S(O)_2-$ | — | $2\text{-CH}_3-4\text{-C}_2H_5-C_6H_3$ | O | H | $-(CH_2)_2-$ | $-N(CH_3)_2$ | HCl |
| g | 1 | 3-piperidinyl | — | $-S(O)_2-$ | — | $2,4(OCH_3)_2-C_6H_3$ | O | H | $-(CH_2)_2-$ | $-N(CH_3)_2$ | HCl |
| h | 1 | " | — | $-S(O)_2-$ | — | $2,4(OC_2H_5)_2-C_6H_3-$ | O | H | $-(CH_2)_2-$ | $-N(CH_3)_2$ | HCl |
| i | 1 | " | — | $-S(O)_2-$ | — | $3\text{-Cl}-4\text{-(OCH}_3)-C_6H$ | O | H | $-(CH_2)_2-$ | $-N(CH_3)_2$ | HCl |
| j | 1 | " | — | $-S(O)_2-$ | — | $3\text{-Cl}-5\text{-(OCH}_3)-C_6H_3$ | O | H | $-(CH_2)_2-$ | $-N(CH_3)_2$ | HCl |
| k | 1 | " | — | $-S(O)_2-$ | — | $2,6(OCH_3)_2-C_6H_3-$ | O | H | $-(CH_2)_2-$ | $-N(CH_3)_2$ | HCl |

TABLE 2-continued $$Y=C-N-A-NR^1R^2$$
$$\phantom{Y=C-N-}R$$

with (CH$_2$)$_n$ and piperidine ring bearing $(A^1)_p$—X—$(A^2)_d$—Q

| Ex. No. | n | Position of —(A$^1$)$_p$—X—(A$^2$)$_d$—Q | (A$^1$)$_p$ | X | (A$^2$)$_d$ | Q | Y | R | A | —NR$^1$R$^2$ | Salt |
|---|---|---|---|---|---|---|---|---|---|---|---|
| 1 | 1 | " | — | —S(O)$_2$— | — | 3-Cl—4,5(OCH$_3$)$_2$—C$_6$H$_2$— | O | H | —(CH$_2$)$_2$— | —N(CH$_3$)$_2$ | HCl |
| m | 1 | " | — | —S(O)$_2$— | — | 4(OC$_4$H$_9$)—C$_6$H$_4$— | O | H | —(CH$_2$)$_2$— | —N(CH$_3$)$_2$ | HCl |
| n | 1 | " | — | —S(O)$_2$— | — | 3-CH$_3$—4(OCH$_3$)C$_6$H$_3$— | O | H | —(CH$_2$)$_2$— | —N(CH$_3$)$_2$ | HCl |
| o | 1 | " | — | —S(O)$_2$— | — | 3-CH$_3$—4(OC$_2$H$_5$)—C$_6$H$_3$ | O | H | —(CH$_2$)$_2$— | —N(CH$_3$)$_2$ | HCl |
| 41a | 1 | " | — | —S(O)$_2$— | — | 2-Cl—6-NO$_2$—C$_6$H$_3$— | O | H | —(CH$_2$)$_2$— | —N(CH$_3$)$_2$ | HCl |
| b | 1 | " | — | —S(O)$_2$— | — | 3-Cl—4-NO$_2$—C$_6$H$_3$— | O | H | —(CH$_2$)$_2$— | —N(CH$_3$)$_2$ | HCl |
| c | 1 | " | — | —S(O)$_2$— | — | 2-NO$_2$—4-Cl—C$_6$H$_3$— | O | H | —(CH$_2$)$_2$— | —N(CH$_3$)$_2$ | HCl |
| d | 1 | " | — | —S(O)$_2$— | — | 3-Cl—5-NO$_2$—C$_6$H$_3$— | O | H | —(CH$_2$)$_2$— | —N(CH$_3$)$_2$ | HCl |
| e | 1 | " | — | —S(O)$_2$— | — | 3-NO$_2$—4-Cl—C$_6$H$_3$— | O | H | —(CH$_2$)$_2$— | —N(CH$_3$)$_2$ | HCl |
| f | 1 | " | — | —S(O)$_2$— | — | 2-NO$_2$—5-Cl—C$_6$H$_3$— | O | H | —(CH$_2$)$_2$— | —N(CH$_3$)$_2$ | HCl |
| g | 1 | " | — | —S(O)$_2$— | — | 3-Cl—4-SCH$_3$—C$_6$H$_3$ | O | H | —(CH$_2$)$_2$— | —N(CH$_3$)$_2$ | HCl |
| h | 1 | " | — | —S(O)$_2$— | — | 3-Cl—4-SC$_6$H$_5$—C$_6$H$_3$ | O | H | —(CH$_2$)$_2$— | —N(CH$_3$)$_2$ | HCl |
| i | 1 | " | — | —S(O)$_2$— | — | 3-Cl—C$_6$H$_4$ | O | H | —(CH$_2$)$_2$— | —N(CH$_3$)$_2$ | HCl |
| 42a | 1 | " | —CH$_2$— | —S(O)$_2$— | — | 1-naphthyl | O | H | —(CH$_2$)$_2$— | —N(CH$_3$)$_2$ | HCl |
| b | 1 | " | —CH$_2$— | —S(O)$_2$— | — | 4-indanyl | O | H | —(CH$_2$)$_2$— | —N(CH$_3$)$_2$ | HCl |
| c | 1 | " | —CH$_2$— | —S(O)$_2$— | — | 3-Cl—C$_6$H$_4$— | O | H | —(CH$_2$)$_2$— | —N(CH$_3$)$_2$ | HCl |
| d | 1 | " | —CH$_2$— | —S(O)$_2$— | —CH$_2$— | 3-Cl—C$_6$H$_4$— | O | H | —(CH$_2$)$_2$— | —N(CH$_3$)$_2$ | HCl |
| 43a | 1 | " | —CH$_2$— | —S(O)$_2$— | —CH$_2$— | 1-naphthyl | O | H | —(CH$_2$)$_2$— | —N(CH$_3$)$_2$ | HCl |
| b | 1 | " | —CH$_2$— | —S(O)$_2$— | —CH$_2$— | 4-biphenyl | O | H | —(CH$_2$)$_2$— | —N(CH$_3$)$_2$ | HCl |
| c | 1 | " | —CH$_2$— | —S(O)$_2$— | — | 4-Cl—C$_6$H$_4$— | O | H | —(CH$_2$)$_2$— | —N(CH$_3$)$_2$ | HCl |
| 44 | 1 | 2-piperidinyl | —CH$_2$— | —S(O)$_2$— | — | 3-Cl—C$_6$H$_4$— | O | H | —(CH$_2$)$_2$— | —N(CH$_3$)$_2$ | — |
| 45a | 1 | 3-piperidinyl | —CH$_2$— | —S(O)$_2$— | —CH$_2$— | 1-naphthyl | O | H | —(CH$_2$)$_2$— | —N(CH$_3$)$_2$ | — |
| b | 1 | " | — | —S(O)$_2$— | —CH$_2$— | 2,3-dihydro-1H—inden-4-yl | O | H | —(CH$_2$)$_2$— | —N(CH$_3$)$_2$ | HCl |
| c | 1 | 3-pyrrolidinyl | — | —S(O)$_2$— | — | 3-Cl—C$_6$H$_4$— | O | H | —(CH$_2$)$_2$— | —N(CH$_3$)$_2$ | HCl |
| 46a | 0 | 3-piperidinyl | — | —S(O)$_2$— | — | C$_6$H$_5$— | S | H | —(CH$_2$)$_2$— | —N(CH$_3$)$_2$ | HCl |
| b | 0 | " | — | —S(O)$_2$— | — | 4-CH$_3$—C$_6$H$_4$— | S | H | —(CH$_2$)$_2$— | —N(CH$_3$)$_2$ | HCl |
| c | 1 | 3-piperidinyl | — | —S(O)$_2$— | — | C$_6$H$_5$— | S | H | —(CH$_2$)$_2$— | —N(CH$_3$)$_2$ | HCl |
| d | 1 | " | — | —S(O)$_2$— | — | 4-CH$_3$—C$_6$H$_4$— | S | H | —(CH$_2$)$_2$— | —N(CH$_3$)$_2$ | HCl |
| e | 1 | 4-piperidinyl | — | —S(O)$_2$— | — | 4-OCH$_3$—C$_6$H$_4$— | O | H | —(CH$_2$)$_2$— | —N(CH$_3$)$_2$ | HCl |
| 47 | 1 | " | — | —S— | — | 2,5-Cl$_2$—C$_6$H$_3$— | O | H | —(CH$_2$)$_2$— | —N(C$_2$H$_5$)$_2$ | — |
| 48 | 1 | " | — | —S— | — | 4-Cl—C$_6$H$_4$— | O | H | —(CH$_2$)$_2$— | —N(C$_2$H$_5$)$_2$ | — |
| 49 | 1 | " | — | —S— | — | C$_6$H$_5$ | O | H | —(CH$_2$)$_2$— | —N(C$_2$H$_5$)$_2$ | — |
| 50 | 1 | " | — | —S— | — | 2-Cl—C$_6$H$_4$— | O | H | —(CH$_2$)$_2$— | —N(C$_2$H$_5$)$_2$ | — |
| 51 | 1 | " | — | —S— | — | 3-Cl—C$_6$H$_4$— | O | H | —(CH$_2$)$_2$— | —N(C$_2$H$_5$)$_2$ | — |
| 52 | 1 | " | — | —S— | — | 3,4-Cl$_2$—C$_6$H$_4$— | O | H | —(CH$_2$)$_2$— | —N(C$_2$H$_5$)$_2$ | — |
| 53 | 1 | " | — | —S— | — | 2-Cl—C$_6$H$_4$— | O | H | —(CH$_2$)$_2$— | —N(C$_2$H$_5$)$_2$ | — |
| 54 | 1 | 3-piperidinyl | — | —S— | — | 4-F—C$_6$H$_4$— | O | H | —(CH$_2$)$_2$— | —N(C$_2$H$_5$)$_2$ | — |
| 55 | 1 | 4-piperidinyl | —CH$_2$— | —S— | — | 4-Cl—C$_6$H$_4$— | O | H | —(CH$_2$)$_2$— | —N(C$_2$H$_5$)$_2$ | — |
| 56 | 1 | 2-piperidinyl | — | —S— | — | C$_6$H$_5$ | O | H | —(CH$_2$)$_2$— | —N(C$_2$H$_5$)$_2$ | — |
| 57 | 1 | 4-piperidinyl | — | —S(O)— | — | C$_6$H$_5$ | O | H | —(CH$_2$)$_2$— | —N(C$_2$H$_5$)$_2$ | — |

TABLE 2-continued $$Y=C-N-A-NR^1R^2$$ with piperidine ring bearing $(A^1)_p-X-(A^2)_d-Q$ substituent

| Ex. No. | n | Position of $-(A^1)_p-X-(A^2)_d-Q$ | $(A^1)_p$ | X | $(A^2)_d$ | Q | Y | R | A | $-NR^1R^2$ | Salt |
|---|---|---|---|---|---|---|---|---|---|---|---|
| 58 | 1 | 3-piperidinyl | —CH$_2$— | —S— | — | C$_6$H$_5$— | O | H | —(CH$_2$)$_2$— | —N(C$_2$H$_5$)$_2$ | — |
| 59 | 1 | 4-piperidinyl | — | —S— | —CH$_2$— | C$_6$H$_5$— | O | H | —(CH$_2$)$_2$— | —N(C$_2$H$_5$)$_2$ | — |
| 60 | 1 | " | — | —S(O)$_2$— | —CH$_2$— | C$_6$H$_5$— | O | H | —(CH$_2$)$_2$— | —N(C$_2$H$_5$)$_2$ | — |
| 61 | 1 | 3-piperidinyl | — | —S— | — | C$_6$H$_5$— | O | H | —(CH$_2$)$_2$— | —N(C$_2$H$_5$)$_2$ | — |
| 62a | 1 | " | — | —S(O)$_2$— | — | 3,4-(OCH$_3$)$_2$—C$_6$H$_3$ | O | H | —(CH$_2$)$_2$— | —N(CH$_3$)$_2$ | — |
| b | 1 | " | — | —S(O)$_2$— | — | 3,4-(OCH$_3$)$_2$—C$_6$H$_3$ | O | H | —(CH$_3$)$_2$ | —(CH$_2$)$_2$— | —N(CH$_3$)$_2$ | — |
| c | 1 | " | — | —S(O)$_2$— | — | 3,5-(OCH$_3$)$_2$—C$_6$H$_3$ | O | H | —(CH$_2$)$_2$— | —N(CH$_3$)$_2$ | — |
| d | 1 | " | — | —S(O)$_2$— | — | 3,4,5-(OCH$_3$)$_3$—C$_6$H$_2$ | O | H | —(CH$_2$)$_2$— | —N(CH$_3$)$_2$ | — |
| 63a | 1 | " | — | —S(O)$_2$— | — | 3-Cl—C$_6$H$_4$— | O | H | —(CH$_2$)$_2$— | 2,6-(CH$_3$)$_2$—piperidin-1-yl | — |
| b | 1 | " | — | —S(O)$_2$— | — | 3-Cl—C$_6$H$_4$— | O | H | —(CH$_2$)$_2$— | 4-OH—4-C$_6$H$_5$—piperidin-1-yl | — |
| c | 1 | " | — | —S(O)$_2$— | — | 3-Cl—C$_6$H$_4$— | O | H | —(CH$_2$)$_2$— | 4-CN—4-C$_6$H$_5$—piperidin-1-yl | — |
| d | 1 | " | — | —S(O)$_2$— | — | 3-Cl—C$_6$H$_4$— | O | H | —(CH$_2$)$_2$— | 4-C$_6$H$_5$—1,2,3,6-tetrahydro-pyridin-1-yl | — |
| e | 1 | " | — | —S(O)$_2$— | — | 3-Cl—C$_6$H$_4$— | O | H | —(CH$_2$)$_2$— | 4-C$_6$H$_5$—CH$_2$—piperidin-1-yl | — |
| 64 | 1 | " | — | —S(O)$_2$— | — | 4-[C(O)NH$_2$]—C$_6$H$_4$— | O | H | —(CH$_2$)$_2$— | —N(CH$_3$)$_2$ | — |
| 65 | 1 | " | — | —S(O)$_2$— | — | 4-[C(O)N(CH$_3$)$_2$]—C$_6$H$_4$— | O | H | —(CH$_2$)$_2$— | —N(CH$_3$)$_2$ | — |
| 66 | 1 | " | — | —S(O)$_2$— | — | C$_6$H$_5$— | O | H | —(CH$_2$)$_2$— | —NHC$_2$H$_5$ | — |
| 67 | 0 | 3-pyrrolidinyl | — | —S(O)$_2$— | — | C$_6$H$_5$— | O | H | —(CH$_2$)$_2$— | —N(C$_2$H$_5$)$_2$ | — |
| 68 | 2 | 4-homopiperidinyl | — | —S— | — | C$_6$H$_5$— | O | H | —(CH$_2$)$_2$— | —N(C$_2$H$_5$)$_2$ | oxalate |
| 69 | 2 | 3-homopiperidinyl | — | —S— | — | C$_6$H$_5$— | O | H | —(CH$_2$)$_2$— | —N(C$_2$H$_5$)$_2$ | oxalate |
| 70 | 2 | 4-homopiperidinyl | — | —S(O)$_2$— | — | C$_6$H$_5$— | O | H | —(CH$_2$)$_2$— | —N(C$_2$H$_5$)$_2$ | fumarate |
| 71a | 2 | " | — | —S(O)— | — | C$_6$H$_5$— | O | H | —(CH$_2$)$_2$— | —N(C$_2$H$_5$)$_2$ | — |
| 71b | 2 | " | — | —S(O)— | — | C$_6$H$_5$— | O | H | —(CH$_2$)$_2$— | —N(C$_2$H$_5$)$_2$ | — |
| 72 | 2 | 3-homopiperidinyl | — | —S(O)$_2$— | — | C$_6$H$_5$— | O | H | —(CH$_2$)$_2$— | —N(C$_2$H$_5$)$_2$ | fumarate |

PHARMACOLOGY

The action of compounds of this invention in correcting cardiac arrhythmias or preventing cardiac arrhythmias is demonstrated by the following procedures:

Ouabain Induced Arrhythmias

Correction of existing cardiac arrhythmias of ventricular origin is carried out on (1) adult mongrel dogs which are under barbiturate anesthesia during the test. A Grass Model 7 polygraph was used for recording femoral arterial blood pressure (Statham P23AC transducer) and the electrocardiogram (Grass 7P4 preamplifier). Ouabain was given intravenously in an initial dose of 40 μg/kg and in a second dose of 20 μg/kg 30 minutes after the first dose and in subsequent doses of 10 μg/kg which were repeated at 15 min. intervals as required for producing cardiac arrhythmias that persisted for at least 15 minutes. When the arrhythmias were established, the test compounds were administered by infusion (Harvard Model 942 Infusion Pump) into a femoral vein at a rate of 1 mg/kg/min. Concentration of compound was adjusted according to the weight of the dog to allow a volume infusion of 1 ml/min. The compound was considered to be active as antiarrhythmic agent if reversion to to sinus rhythm occurred which was maintained for at least 30 min.

Coronary Artery Ligation Induced Arrhythmias

Adult mongrel dogs which are in the conscious state were used for the test and cardiac arrhythmias were induced by prior (22–24 hr) surgical preparation in which blood flow through a coronary artery was occluded by use of a constrictor device as reported by Smith et al, 1973. A Grass Model 79 polygraph was used for recording the electrocardiogram (Grass 7P4 preamplifier).

The test compound was administered by infusion (Harvard Model 942 Infusion Pump) into a saphenous vein to one group of dogs at a rate of 0.5 mg/kg/min. Concentration of compound was adjusted according to the weight of the dog to allow a volume of infusion of 0.5 ml/min. The test compound was administered orally by gavage to another group of dogs at dose levels of 10 through 40 mg/kg. The test compound was prepared in distilled water to give a total volume of 20 ml. Following the administration of the test compound, the heart rate, number of ectopic cardiac beats per min, and the percent ectopic beats (ectopic beats/HR X100) were recorded at 15 min. intervals. The compound was considered active if it abolished the ectopic ventricular frequency and caused a return to normal sinus rhythm within 2 hours of administration.

Data obtained for one preferred compound; namely, N-[2-(diethylamino)ethyl]-3-(phenylsulfonyl)-1-piperidine carboxamide as represented by its oxalate salt of Example 20 are shown in Table 1. The other compounds of this invention show qualitatively similar effects in one or more types of arrhythmias as represented by the foregoing tests. In general the compounds of this invention exhibit less CNS side effects than quinidine or lidocaine. The sulfones being superior in this respect at the same time exhibiting excellent antiarrhythmic activity.

TABLE 3

Effect of Compound of Example 20: N—[2-(diethylamino)ethyl]-3-(phenylsulfonyl)-1-piperidinecarboxamide oxalate on Cardiac Arrhythmias in Dogs

| Arrhythmia Model | Correcting Dose Range mg/kg I.V. |
| --- | --- |
| Ouabain-Induced[1] | 3–7 |
| Coronary Artery Ligation Induced[2] | 4–12 |

[1]Cardiac arrhythmias produced by method of Lucchessi and Hardman, 1961, J. Pharmacol. Exp. Therap. 132, 372-381.
[2]Cardiac arrhythmias produced by modification of method of Harris, 1950, Circulation 1, 1318, as reported by Smith et al, 1973, Pharmacologist 15, 192.

Pharmaceutical Compositions and Administration

The invention further provides pharmaceutical compositions for administration to a living animal body comprising, as active ingredients, at least one of the compounds according to the invention in association with a pharmaceutical carrier or excipient. The compounds are thus presented in a therapeutic composition suitable for oral, rectal, parenteral or intracardial administration. Thus, for example, compositions for oral administration are preferably solids and can take the form of capsules, tablets or coated tablets containing carriers conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid; e.g., water, or a parenterally acceptable oil; e.g., arachis oil, contained in ampoules.

In compositions for rectal administration the carrier can comprise a suppository base; e.g., cocoa butter, or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be obtained consistent with the dosage form employed. The exact individual dosages, as well as daily dosages, will, of course, be determined according to standard medical principles under the direction of a physician or veterinarian. Generally, the pharmacology on animals suggests the the oral dosage effective to correct arrhythmias will be about 3 times that of the intravenous dosage. The animal data also suggest dosage requirements will be about half that of quinidine for the more active compounds.

Based on the animal data, allowing for variation in species and severity of cardiac arrhythmia unit dosages containing an amount of compound equivalent to about 1 to about 100 mg/kg of body weight, are contemplated. Based on all of the above considerations, a choice in a range of unit oral dosages for humans of about 10 to about 1000 mg is contemplated, preferably about 10 to 600 mg for a more active compound such as Example 20. Daily dosages of about 30 to 2400 mg are contemplated for humans and obviously several unit dosage forms may e administered at about the same time. However, the scope of the invention is not to be limited by these contemplations due to the uncertainty in transpositions discussed above.

Examples of unit dosage compositions are as follows:

| Capsules | |
|---|---|
| Ingredients | Per Cap. |
| 1. Active ingredient | 10.0 mg. |
| 2. Lactose | 146.0 mg. |
| 3. Magnesium Stearate | 4.0 mg. |

Procedure
1. Blend 1, 2 and 3.
2. Mill this blend and blend again.
3. This milled blend is then filled into #1 hard gelatin capsules.

| Ingredients | Mg./Tab. |
|---|---|
| Tablets (10 mg) | |
| 1. Active ingredient | 10.0 mg. |
| 2. Corn starch | 20.0 mg. |
| 3. Kelacid | 20.0 mg. |
| 4. Keltose | 20.0 mg. |
| 5. Magnesium stearate | 1.3 mg. |
| Tablets (50 mg) | |
| 1. Active ingredient | 50.0 mg. |
| 2. Milo starch | 20.0 mg. |
| 3. Corn starch | 38.0 mg. |
| 4. Lactose | 90.0 mg. |
| 5. Calcium stearate | 2.0 mg. |
| | 200.0 mg. |

Procedure
1. Blend 1, 2, 3 and 4.
2. Add sufficient water portionwise to the blend from step #1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | |
|---|---|
| Ingredients | Per ml. |
| 1. Active ingredient | 1.0 mg. |
| 2. pH 4.0 Buffer solution | q.s. to 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | |
|---|---|
| Ingredients | Per ml. |
| 1. Active ingredients | 5.0 mg. |

| Intramuscular Injection | |
|---|---|
| Ingredients | Per ml. |
| 2. Isotonic Buffer solution 4.0 | q.s. to 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Suppositories | |
|---|---|
| Ingredients | Per Supp. |
| 1. Active ingredient | 10.0 mg. |
| 2. Polyethylene Glycol 1000 | 1350.0 mg. |
| 3. Polyethylene Glycol 4000 | 450.0 mg. |

Procedure
1. Melt 2 and 3 together and stir until uniform.
2. Dissolve #1 in the molten mass from step 1 and stir until uniform.
3. Pour the molten mass from step 2 into suppository molds and chill.
4. Remove the suppositories from molds and wrap.

Therapeutic compositions having cardiac arrhythmia inhibiting activity in dosage unit form, comprising a pharmaceutical carrier and a cardiac arrhythmia inhibiting amount of a compound of Formula I or a pharmaceutically acceptable acid addition salt thereof are therefore an embodiment of this invention.

Various modifications and equivalents will be apparent to one skilled in the art and may be made in the compounds, method, and compositions of the present invention without departing from the spirit or scope thereof, and it is therefore to be understood that the invention is to be limited only by the scope of the appended claims.

What is claimed is:

1. A compound selected from the group having the formula:

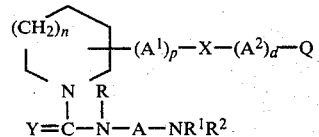

wherein;
n is selected from zero, one or two;
Y is selected from oxygen or sulfur;
A, $A^1$ and $A^2$ are selected from straight or branched-chain alkalenes having 1 to 8 carbon atoms and p and d are selected from zero or one with the proviso that when the $—(A^1)_p—X—(A^2)_d—Q$ radical is in the 2-position, p is at at least one;
X is selected from $—S—$, $—S(O)—$ or $—S(O)_2—$;
R, $R^1$ and $R^2$ are selected from hydrogen, loweralkyl (1-8 carbons), phenyl, cycloalkyl (1-9 carbons) or phenylalkyl (7-14 carbons) and may be the same or different and $R^1$ and $R^2$ taken together with the adjacent nitrogen atom may form a heterocyclic residue selected from the group consisting of (a) 1-pyrrolidino,
(b) 1-piperidino,
(c) 4-morpholino,
(d) 1-piperazino,
(e) a heterocycle of (a) to (d) substituted by a methyl, ethyl, phenyl or phenylloweralkyl,
(f) 2,6-(loweralkyl)$_2$-piperidino,
(g) 4-hydroxy-4-phenylpiperidino,
(h) 4-cyano-4-phenylpiperidino, or,
(i) 4-phenyl-1,2,3,6-tetrahydropyridino, Q is selected from the group consisting of:
(1) 1 or 2-naphthyl,
(2) 2,3-dihydro-1H-inden-4-yl or 2,3-dihydro-1H-inden-5-yl,
(3) biphenyl,
(4) phenyl,

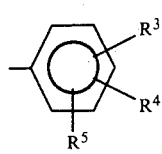

(5)

wherein $R^3$ is selected from fluorine, chlorine, bromine, iodine, loweralkyl (1-8 carbons), loweralkoxy (1-8 carbons), trifluoromethyl, hydroxy, cyano or nitro, $R^4$ is selected from hydrogen, fluorine, chlorine, bromine, iodine, methyl, ethyl, isopropyl, methoxy, ethoxy and nitro and $R^5$ is selected from hydrogen, methyl, ethyl, methoxy, ethoxy, methylthio and phenylthio,

(6)

wherein $R^6$ is selected from $-NR^7R^8$, $-C(O)NR^7R^8$, $-(CH_2)_bNR^7R^8$, $-B-(CH_2)_bNR^7R^8$ or $-B-(CH_2)_bOR^7$ wherein B is selected from $-O-$, $-S-$, $-S(O)-$ or $-S(O)_2-$, b is 2 or 3 and $R^7$ and $R^8$ are selected from hydrogen, loweralkyl (1-8 carbons), and may be the same or different,

(7)

wherein $R^9$ is selected from $-SR^{10}$, $-S(O)R^{10}$ and $-S(O_2)R^{10}$ wherein $R^{10}$ is selected from loweralkyl (1-8 carbons) and phenyl with the proviso that X must be $-S(O)_2-$, or,

(8)

wherein $A^3$ is selected from straight or branched-chain alkalenes (2-8 carbons) and G is selected from loweralkoxy (1-8 carbons) or $-NR^{11}R^{12}$ wherein $R^{11}$ and $R^{12}$ are selected from hydrogen, loweralkyl (1 to 8 carbons), phenyl and phenyl-loweralkyl (7-14 carbons) and may be the same or different, and the pharmaceutically acceptable acid addition salts and hydrates thereof.

2. The compound of claim 1 which is 3-[4-(chlorophenyl)thio]-N-[2-(diethylamino)ethyl]-1-pyrrolidinecarboxamide or a pharmaceutically acceptable acid addition salt or hydrate thereof.

3. The compound of claim 1 which is 3-[(4-chlorophenyl)thio]-N-[2-(dimethylamino)ethyl]-1-pyrrolidinecarboxamide or a pharmaceutically acceptable acid addition salt or hydrate thereof.

4. The compound of claim 1 which is 3-[(4-chlorophenyl)thio]-N-[2-(dimethylamino)ethyl]-1-pyrrolidinecarboxamide or a pharmaceutically acceptable acid addition salts or hydrates thereof.

5. The compound of claim 1 which is 3-[(4-chlorophenyl)sulfinyl]-N-[2-(diethylamino)ethyl]-1-pyrrolidinecarboxamide or a pharmaceutically acceptable acid addition salt or hydrate thereof.

6. The compound of claim 1 which is 3-[(4-chlorophenyl)sulfonyl]-N-[2-(diethylamino)ethyl]-1-pyrrolidinecarboxamide or a pharmaceutically acceptable acid addition salt or hydrate thereof.

7. The compound of claim 1 which is 3-[(4-chlorophenyl)sulfonyl]-N-[2-(dimethylamino)ethyl]-1-pyrrolidinecarboxamide or a pharmaceutically acceptable acid addition salt or hydrate thereof.

8. The compound of claim 1 which is 3-(phenylsulfonyl)-N-[2-(diethylamino)ethyl]-1-pyrrolidinecarboxamide or a pharmaceutically acceptable acid addition salt or hydrate thereof.

9. The compound of claim 1 which is N-[2-(diethylamino)ethyl]-3-[(4-methylphenyl)thio]-1-pyrrolidinecarboxamide or a pharmaceutically acceptable acid addition salt or hydrate thereof.

10. The compound of claim 1 which is N-[2-(diethylamino)ethyl]-3-[(4-methylphenyl)sulfonyl]-1-pyrrolidinecarboxamide or a pharmaceutically acceptable acid addition salt or hydrate thereof.

11. The compound of claim 1 which is N-[3-(diethylamino)propyl]-3-(phenylsulfonyl)-1-pyrrolidinecarboxamide or a pharmaceutically acceptable acid addition salt or hydrate thereof.

12. The compound of claim 1 which is 3-[(3,4-dichlorophenyl)sulfonyl]-N-(2-(dimethylamino)ethyl]-1-pyrrolidinecarboxamide or a pharmaceutically acceptable acid addition salt or hydrate thereof.

13. The compound of claim 1 which is 3-[(3,4-dichlorophenyl)sulfonyl]-N-[2-(diethylamino)ethyl]-1-pyrrolidinecarboxamide or a pharmaceutically acceptable acid addition salt or hydrate thereof.

14. The compound of claim 1 which is 3-[(3,4-dichlorophenyl)thio]-N-[2-(diethylamino)ethyl]-1-pyrrolidinecarboxamide or a pharmaceutically acceptable acid addition salt or hydrate thereof.

15. The compound of claim 1 which is 3-[(4-chlorophenyl)sulfonyl]-N-[2-(dimethylamino)ethyl]-1-piperidinecarboxamide or a pharmaceutically acceptable acid addition salt or hydrate thereof.

16. The compound of claim 1 which is 3-[(4-chlorophenyl)thio]-N-[2-(dimethylamino)ethyl]-1-piperidinecarboxamide or a pharmaceutically acceptable acid addition salt or hydrate thereof.

17. The compound of claim 1 which is 3-[(3-chlorophenyl)sulfonyl]-N-[2-(dimethylamino)ethyl]-1-piperidinecarboxamide or a pharmaceutically acceptable acid addition salt or hydrate thereof.

18. The compound of claim 1 which is 3-[(3-chlorophenyl)thio]-N-[2-(dimethylamino)ethyl]-1- piperidinecarboxamide or a pharmaceutically acceptable acid addition salt or hydrate thereof.

19. The compound of claim 1 which is 3-[(4-chlorophenyl)sulfinyl]-N-[2-(dimethylamino)ethyl]-1-piperidinecarboxamide or a pharmaceutically acceptable acid addition salt or hydrate thereof.

20. The compound of claim 1 which is 3-[(4-chlorophenyl)sulfonyl]-N-[2-(diethylamino)ethyl]-1-piperidinecarboxamide or a pharmaceutically acceptable acid addition salt or hydrate thereof.

21. The compound of claim 1 which is N-[2-(diethylamino)ethyl]-3-(phenylsulfonyl)-1-piperidinecarboxamide or a pharmaceutically acceptable acid addition salt or hydrate thereof.

22. The compound of claim 1 which is N-[2-(dimethylamino)ethyl]-3-(phenylsulfonyl)-1-piperidinecarboxamide or a pharmaceutically acceptable acid addition salt or hydrate thereof.

23. The compound of claim 1 which is N-[2-(diethylamino)ethyl]-3-(phenylsulfonyl)-1-piperidinecarbothioamide or a pharmaceutically acceptable acid addition salt or hydrate thereof.

24. The compound of claim 1 which is N-[2-(diethylamino)ethyl]-3-[(4-methylphenyl)sulfonyl]-1-piperidinecarboxamide or a pharmaceutically acceptable acid addition salt or hydrate thereof.

25. The compound of claim 1 which is N-[2-(diethylamino)ethyl]-3-[(4-fluorophenyl)sulfonyl]-1-piperidinecarboxamide or a pharmaceutically acceptable acid addition salt or hydrate thereof.

26. The compound of claim 1 which is N-[3-(diethylamino)propyl]-3-(phenylsulfonyl)-1-piperidinecarboxamide or a pharmaceutically acceptable acid addition salt or hydrate thereof.

27. The compound of claim 1 which is N-[2-(diethylamino)ethyl]-3-[(4-methoxyphenyl)sulfonyl]-1-piperidinecarboxamide or a pharmaceutically acceptable acid addition salt or hydrate thereof.

28. The compound of claim 1 which is N-[2-[bis(1-methylethyl)amino]ethyl]-3-(phenylsulfonyl)-1-piperidinecarboxamide or a pharmaceutically acceptable acid addition salt or hydrate thereof.

29. The compound of claim 1 which is 4-[(4-chlorophenyl)thio]-N-[2-(dimethylamino)ethyl]-1-piperidinecarboxamide or a pharmaceutically acceptable acid addition salt or hydrate thereof.

30. The compound of claim 1 which is 4-[4-(chlorophenyl)sulfonyl]-N-[2-(dimethylamino)ethyl]-1-piperidinecarboxamide or a pharmaceutically acceptable acid addition salt or hydrate thereof.

31. The compound of claim 1 which is 4-[(4-chlorophenyl)sulfinyl]-N-[2-(dimethylamino)ethyl]-1-piperidinecarboxamide or a pharmaceutically acceptable acid addition salt or hydrate thereof.

32. The compound of claim 1 which is N-[2-(diethylamino)ethyl]-3-[[4-[2-(dimethylamino)ethoxy]phenyl]sulfony]-1-piperidinecarboxamide or a pharmaceutically acceptable acid addition salt thereof.

33. The compound of claim 1 which is N-[2-(diethylamino)ethyl]-3-[[4-(2-methoxyethoxy]phenyl]sulfonyl]-1-piperidinecarboxamide or a pharmaceutically acceptable acid addition salt or hydrate thereof.

34. The compound of claim 1 which is 3-[[4-[2-(diethylamino)ethoxy]phenyl]sulfonyl]-N-[2-(diethylamino)ethyl]-1-piperidinecarboxamide or a pharmaceutically acceptable acid addition salt or hydrate thereof.

35. The compound of claim 1 which is N-[2-(dimethylamino)ethyl]-3-[(phenylsulfonyl)methyl]-1-piperidinecarboxamide or a pharmaceutically acceptable acid addition salt or hydrate thereof.

36. The compound of claim 1 which is N-[2-(diethylamino)ethyl]-3-[(phenylsulfonyl)methyl]-1-piperidinecarboxamide or a pharmaceutically acceptable acid addition salt or hydrate thereof.

37. A method for treating cardiac arrhythmia in an animal which comprises administering to said animal an effective amount of a compound having the formula:

$$\begin{array}{c} (CH_2)_n \\ \diagup \quad \diagdown \\ \quad \quad \quad -(A^1)_p-X-(A^2)_d-Q \\ \diagdown \quad \diagup \\ N \quad R \\ | \quad | \\ Y=C-N-A-NR^1R^2 \end{array}$$

wherein;
n is selected from zero, one or two;
Y is selected from oxygen or sulfur;
A, $A^1$ and $A^2$ are selected from straight or branched-chain alkalenes having 1 to 8 carbon atoms and p and d are selected from zero or one with the proviso that when the $-(A^1)_p-X-(A^2)_d-Q$ radical is in the 2-position, p is at least one;
X is selected from $-S-$, $-S(O)-$, or $-S(O)_2-$;
R, $R^1$ and $R^2$ are selected from hydrogen, loweralkyl (1-8 carbons), phenyl, cycloalkyl (1-9 carbons) or phenylalkyl (7-14 carbons) and may be the same or different and $R^1$ and $R^2$ taken together with the adjacent nitrogen atom may form a heterocyclic residue selected from the group consisting of
(a) 1-pyrrolidino,
(b) 1-piperidino,
(c) 4-morpholino,
(d) 1-piperazino,
(e) a heterocycle of (a) to (d) substituted by a methyl, ethyl, phenyl or phenylloweralkyl,
(f) 2,6-(loweralkyl)$_2$-piperidino,
(g) 4-hydroxy-4-phenylpiperidino,
(h) 4-cyano-4-phenylpiperidino, or,
(i) 4-phenyl-1,2,3,6-tetrahydropyridino,
Q is selected from
(1) 1 or 2-naphthyl,
(2) 2,3-dihydro-1H-inden-4-yl or 2,3-dihydro-1H-inden-5-yl,
(3) biphenyl,
(4) phenyl, (5)

$$\underset{R^5}{\underset{|}{\bigcirc}}\!\!\diagdown\!\!\begin{array}{c}R^3\\ \\R^4\end{array}$$

wherein $R^3$ is selected from fluorine, chlorine, bromine, iodine, loweralkyl (1-8 carbons), loweralkoxy (1-8 carbons), trifluoromethyl, hydroxy, cyano or nitro, $R^4$ is selected from hydrogen, fluorine, chlorine, bromine, iodine, methyl, ethyl, isopropyl, methoxy, ethoxy and nitro and $R^5$ is selected from hydrogen, methyl, ethyl, methoxy, ethoxy, methylthio and phenylthio,

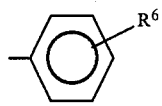
(6)

wherein $R^6$ is selected from —$NR^7R^8$, —C(O)$NR^7R^8$, —(CH$_2$)$_b$$NR^7R^8$, —B—(CH$_2$)$_b$$NR^7R^8$ or —B—(CH$_2$)$_b$$OR^7$ wherein B is selected from —O—, —S—, —S(O)— or —S(O)$_2$—, b is 2 or 3 and $R^7$ and $R^8$ are selected from hydrogen, loweralkyl (1–8 carbons), and may be the same or different,

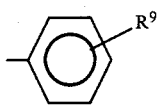
(7)

wherein $R^9$ is selected from —$SR^{10}$, —S(O)$R^{10}$ and —S(O$_2$)$R^{10}$ wherein $R^{10}$ is selected from loweralkyl (1–8 carbons) and phenyl with the proviso that X must be —S(O)$_2$—, or,

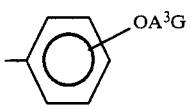
(8)

wherein $A^3$ is selected from straight or branched-chain alkalenes (2–8 carbons) and G is selected from hydrogen, loweralkoxy (1–8 carbons) or —$NR^{11}R^{12}$ wherein $R^{11}$ and $R^{12}$ are selected from loweralkoxy (1–8 carbons), phenyl and phenyl-loweralkyl (7–14 carbons) and may be the same or different, and the pharmaceutically acceptable acid addition salts and hydrates thereof.

38. A therapeutic composition for the treatment of cardiac arrhythmias comprising (a) an effective amount of a compound selected from the group having the formula:

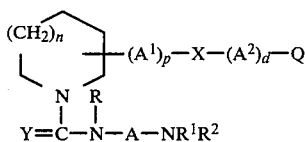

wherein;
n is selected from zero, one or two;
Y is selected from oxygen or sulfur,
A, $A^1$ and $A^2$ are selected from straight or branched-chain alkalenes having 1 to 8 carbon atoms and p and d are selected from zero or one with the proviso that when the —(A$^1$)$_p$—X—(A$^2$)$_d$—Q radical is in the 2-position, p is at least one;
X is selected from —S—, —S(O)— or —S(O)$_2$—, R, $R^1$ and $R^2$ are selected from hydrogen, loweralkyl (1–8 carbons), phenyl, cycloalkyl (1–9 carbons) or phenylalkyl (7–14 carbons) and may be the same or different and $R^1$ and $R^2$ taken together with the adjacent nitrogen atom may form a heterocyclic residue selected from the group consisting of
(a) 1-pyrrolidino,
(b) 1-piperidino,
(c) 4-morpholino,
(d) 1-piperazino,
(e) a heterocyclic of (a) to (d) substituted by a methyl, ethyl, phenyl or phenylloweralkyl,
(f) 2,6-(loweralkyl)$_2$-piperidino,
(g) 4-hydroxy-4-phenylpiperidino,
(h) cyano-4-phenylpiperidino, or,
(i) 4-phenyl-1,2,3,6-tetrahydropyridino,
Q is selected from
(1) 1 or 2 naphthyl,
(2) 2,3-dihydro-1H-inden-4-yl or 2,3-dihydro-1H-inden-5-yl,
(3) biphenyl,
(4) phenyl,

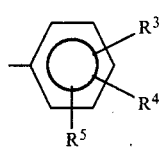
(5)

wherein $R^3$ is selected from fluorine, chlorine, bromine, iodine, loweralkyl (1–8 carbons), loweralkoxy (1–8 carbons), trifluoromethyl, hydroxy, cyano or nitro, $R^4$ is selected from hydrogen, fluorine, chlorine, bromine, iodine, methyl, ethyl, isopropyl, methoxy, ethoxy and nitro and $R^5$ is selected from hydrogen, methyl, ethyl, methoxy, ethoxy, methylthio and phenylthio,

(6)

wherein $R^6$ is selected from —$NR^7R^8$, —C(O)$NR^7R^8$, —(CH$_2$)$_b$$NR^7R^8$, —B—(CH$_2$)$_b$$NR^7R^8$ or —B—(CH$_2$)$_b$$OR^7$ wherein B is selected from —O—, —S—, —S(O)— or —S(O)$_2$—, b is 2 or 3 and $R^7$ and $R^8$ are selected from hydrogen, loweralkyl (1–8 carbons) and may be the same or different,

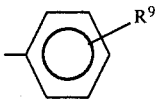
(7)

wherein $R^9$ is selected from —$SR^{10}$, —S(O)$R^{10}$, and —S(O$_2$)$R^{10}$ wherein $R^{10}$ is selected from loweralkyl (1–8 carbons) and phenyl with the proviso that X must be —S(O)$_2$—, or,

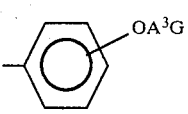
(8)

wherein $A^3$ is selected from straight or branched-chain alkalenes (2–8 carbons) and G is selected from loweralkoxy (1–8 carbons) or —$NR^{11}R^{12}$ wherein $R^{11}$ and $R^{12}$ are selected from hydrogen, loweralkyl (1–8 carbons), phenyl and phenyl-loweralkyl (7–14 carbons) and may be the same or different, and the pharmaceutically acceptable acid addition salts and hydrates thereof, and
(b) a pharmaceutically acceptable carrier therefor.

* * * * *